United States Patent
MacLachlan et al.

(10) Patent No.: US 12,186,475 B1
(45) Date of Patent: Jan. 7, 2025

(54) MEDICAL WASTE COLLECTION SYSTEMS, MANIFOLDS, AND RELATED METHODS

(71) Applicant: Stryker Corporation, Kalamazoo, MI (US)

(72) Inventors: Brian MacLachlan, Norton Shores, MI (US); Grant Westphal, Delton, MI (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/368,297

(22) Filed: Sep. 14, 2023

Related U.S. Application Data

(63) Continuation of application No. 18/103,942, filed on Jan. 31, 2023, now Pat. No. 11,786,647.

(60) Provisional application No. 63/305,267, filed on Jan. 31, 2022.

(51) Int. Cl.
| | |
|---|---|
| *G08B 21/00* | (2006.01) |
| *A61B 90/98* | (2016.01) |
| *A61M 1/00* | (2006.01) |
| *G06K 19/07* | (2006.01) |
| *G16H 40/63* | (2018.01) |

(52) U.S. Cl.
CPC ............... *A61M 1/74* (2021.05); *A61B 90/98* (2016.02); *A61M 1/802* (2021.05); *G06K 19/07* (2013.01); *G16H 40/63* (2018.01); *A61J 2205/60* (2013.01)

(58) Field of Classification Search
CPC ......... A61M 1/74; A61M 1/802; A61B 90/98; G06K 19/07; G16H 40/63; A61J 2205/60
USPC .................................. 340/572, 10; 604/317
See application file for complete search history.

(56) References Cited

U.S. PATENT DOCUMENTS

| | | | |
|---|---|---|---|
| 3,808,634 | A | 5/1974 | Szabo |
| 4,802,198 | A | 1/1989 | Guenther et al. |
| 4,807,837 | A | 2/1989 | Gawlik et al. |
| 4,905,944 | A | 3/1990 | Jost et al. |
| 5,540,901 | A | 7/1996 | Riley |
| 5,563,589 | A | 10/1996 | Blaimont et al. |
| 5,941,182 | A | 8/1999 | Greene |
| 5,974,500 | A | 10/1999 | Maletsky et al. |
| 6,100,804 | A | 8/2000 | Brady et al. |
| 6,318,636 | B1 | 11/2001 | Reynolds et al. |
| 6,343,556 | B1 | 2/2002 | Lanphear |

(Continued)

FOREIGN PATENT DOCUMENTS

| | | |
|---|---|---|
| CN | 201840835 U | 5/2011 |
| CN | 203005496 U | 6/2013 |

(Continued)

OTHER PUBLICATIONS

"Statement Regarding Stryker Neptune 3 Waste Management System", Jan. 2021, 1 page.

(Continued)

*Primary Examiner* — Mark S Rushing
(74) *Attorney, Agent, or Firm* — Howard & Howard Attorneys PLLC

(57) ABSTRACT

A medical waste collection system includes a medical waste collection device for providing suction at a surgical site, and a manifold releasably couplable to the medical waste collection device. The manifold defines a pathway through which the medical waste collection device is configured to provide suction to the surgical site. The medical waste collection device is configured to control activation of suction based on a proper manifold being present.

20 Claims, 10 Drawing Sheets

(56) References Cited

U.S. PATENT DOCUMENTS

| | | |
|---|---|---|
| 6,378,816 B1 | 4/2002 | Pfister |
| 6,607,170 B1 | 8/2003 | Hoftman |
| 6,861,954 B2 | 3/2005 | Levin |
| 6,883,439 B1 | 4/2005 | Moore |
| 6,892,052 B2 | 5/2005 | Kotola et al. |
| 7,048,687 B1 | 5/2006 | Reuss et al. |
| 7,171,890 B2 | 2/2007 | Oudelaar |
| 7,362,228 B2 | 4/2008 | Nycz et al. |
| 7,420,468 B2 | 9/2008 | Fabian et al. |
| 7,483,729 B2 | 1/2009 | Al-Ali et al. |
| 7,492,261 B2 | 2/2009 | Cambre et al. |
| 7,496,521 B1 | 2/2009 | Louie et al. |
| 7,541,933 B2 | 6/2009 | Volpi et al. |
| 7,557,711 B2 | 7/2009 | Volpi et al. |
| 7,594,668 B2 | 9/2009 | Arceta et al. |
| 7,617,137 B2 | 11/2009 | Kreiner et al. |
| 7,632,079 B2 | 12/2009 | Hershberger et al. |
| 7,633,392 B2 | 12/2009 | Neuwirth |
| 7,643,798 B2 | 1/2010 | Ljung |
| 7,703,674 B2 | 4/2010 | Stewart et al. |
| 7,761,188 B2 | 7/2010 | Palmerton et al. |
| 8,035,487 B2 | 10/2011 | Malackowski |
| 8,063,760 B2 | 11/2011 | Volpi et al. |
| 8,074,815 B2 | 12/2011 | Gerstner |
| 8,172,255 B1 | 5/2012 | Martin |
| 8,215,650 B2 | 7/2012 | Arceta et al. |
| 8,245,652 B2 | 8/2012 | Hung |
| 8,279,069 B2 | 10/2012 | Sawyer |
| 8,284,059 B2 | 10/2012 | Ross |
| 8,296,852 B2 | 10/2012 | Friedrich |
| 8,361,070 B2 | 1/2013 | Hanlon et al. |
| 8,365,310 B2 | 1/2013 | Shamir |
| 8,399,822 B2 | 3/2013 | Al-Ali |
| 8,446,245 B2 | 5/2013 | Wang et al. |
| 8,448,907 B2 | 5/2013 | Witschen |
| 8,545,416 B1 | 10/2013 | Kayyali et al. |
| 8,662,605 B2 | 3/2014 | McRorie et al. |
| 8,689,704 B2 | 4/2014 | Hodges et al. |
| 8,692,140 B1 | 4/2014 | Pollock et al. |
| 8,750,796 B2 | 6/2014 | Claus et al. |
| 8,768,251 B2 | 7/2014 | Claus et al. |
| 8,774,713 B2 | 7/2014 | Rose et al. |
| 8,789,156 B2 | 7/2014 | Fisk et al. |
| 8,831,509 B2 | 9/2014 | Moosavi et al. |
| 8,896,420 B2 | 11/2014 | Chang et al. |
| 8,905,317 B1 | 12/2014 | Hsu et al. |
| 8,963,025 B2 | 2/2015 | Pollock et al. |
| 8,981,938 B2 | 3/2015 | H. Kazerouni |
| 8,996,393 B2 | 3/2015 | Sobie |
| 9,039,016 B2 | 5/2015 | Abernethy et al. |
| 9,072,474 B2 | 7/2015 | Al-Ali et al. |
| 9,226,686 B2 | 1/2016 | Blair |
| 9,347,817 B2 | 5/2016 | Pollock et al. |
| 9,355,350 B2 | 5/2016 | Hsu et al. |
| 9,366,746 B2 | 6/2016 | Kazerouni |
| 9,389,643 B1 | 7/2016 | Clark et al. |
| 9,418,249 B2 | 8/2016 | Thueringer et al. |
| 9,475,514 B2 | 10/2016 | Hardy et al. |
| 9,489,785 B2 | 11/2016 | Klammer et al. |
| 9,496,927 B1 | 11/2016 | Grinberg et al. |
| 9,507,981 B2 | 11/2016 | Dor et al. |
| 9,510,737 B2 | 12/2016 | Vayser et al. |
| 9,646,182 B2 | 5/2017 | Volpi et al. |
| 9,774,455 B2 | 9/2017 | Klammer et al. |
| 9,792,408 B2 | 10/2017 | Blair et al. |
| 9,814,540 B2 | 11/2017 | Blair et al. |
| 9,843,580 B2 | 12/2017 | Fairbanks et al. |
| 9,876,320 B2 | 1/2018 | Coverston et al. |
| 9,933,106 B2 | 4/2018 | Stark |
| 9,977,865 B1 | 5/2018 | LaBorde |
| 9,980,681 B1 | 5/2018 | LaBorde |
| 9,996,717 B2 | 6/2018 | Volpi et al. |
| 10,002,269 B2 | 6/2018 | Dor et al. |
| 10,043,592 B1 | 8/2018 | LaBorde |
| 10,070,912 B2 | 9/2018 | Bernard et al. |
| 10,076,284 B1 | 9/2018 | LaBorde |
| 10,117,722 B2 | 11/2018 | Sweeney |
| 10,187,742 B2 | 1/2019 | Dor et al. |
| 10,226,555 B2 | 3/2019 | Vayser et al. |
| 10,278,788 B2 | 5/2019 | Dunning |
| 10,292,661 B1 | 5/2019 | LaBorde |
| 10,298,403 B2 | 5/2019 | Klammer et al. |
| 10,417,465 B2 | 9/2019 | Volpi et al. |
| 10,460,837 B1 | 10/2019 | LaBorde |
| 10,471,188 B1 | 11/2019 | Zollinger et al. |
| 10,482,293 B2 | 11/2019 | Volpi |
| 10,482,377 B1 | 11/2019 | LaBorde |
| 10,499,974 B2 | 12/2019 | Heim et al. |
| 10,531,835 B2 | 1/2020 | Al-Ali et al. |
| 10,628,739 B1 | 4/2020 | LaBorde |
| 10,719,747 B2 | 7/2020 | Stewart et al. |
| 10,722,617 B2 | 7/2020 | Murray et al. |
| 10,758,310 B2 | 9/2020 | Shelton, IV et al. |
| 10,758,649 B2 | 9/2020 | Smith et al. |
| 10,783,991 B1 | 9/2020 | LaBorde |
| 10,804,081 B2 | 10/2020 | Chhatre et al. |
| 10,899,021 B2 | 1/2021 | Robinson et al. |
| 11,069,012 B2 | 7/2021 | Shelton, IV et al. |
| 11,090,516 B2 | 8/2021 | VanDerWoude et al. |
| 11,116,598 B1 | 9/2021 | Fleck et al. |
| 11,160,909 B2 | 11/2021 | Davie et al. |
| 11,234,787 B1 | 2/2022 | Staats et al. |
| 11,291,265 B2 | 4/2022 | Jefferis et al. |
| 11,317,936 B2 | 5/2022 | James et al. |
| 11,351,004 B2 | 6/2022 | Wayne et al. |
| 11,376,093 B2 | 7/2022 | Vayser et al. |
| 11,382,711 B2 | 7/2022 | Grey et al. |
| 2002/0143320 A1 | 10/2002 | Levin |
| 2003/0151511 A1 | 8/2003 | Duncan et al. |
| 2005/0171495 A1 | 8/2005 | Austin et al. |
| 2006/0187059 A1 | 8/2006 | Fabian et al. |
| 2007/0028549 A1 | 2/2007 | Henderson |
| 2008/0029416 A1 | 2/2008 | Paxton |
| 2008/0098212 A1 | 4/2008 | Helms et al. |
| 2008/0129463 A1* | 6/2008 | Tuttle ............ G06K 19/07318 340/10.5 |
| 2008/0252045 A1 | 10/2008 | Rossini et al. |
| 2008/0297326 A1 | 12/2008 | Chakraborty et al. |
| 2009/0015116 A1 | 1/2009 | Arceta et al. |
| 2009/0096574 A1 | 4/2009 | Oberle |
| 2009/0201133 A1 | 8/2009 | Bruns |
| 2009/0267765 A1 | 10/2009 | Greene et al. |
| 2009/0315673 A1* | 12/2009 | Huang ............ G06K 19/07309 340/5.61 |
| 2010/0022900 A1 | 1/2010 | Peterson et al. |
| 2010/0039220 A1 | 2/2010 | Davis |
| 2010/0057167 A1 | 3/2010 | Evers et al. |
| 2010/0303603 A1 | 12/2010 | Galante et al. |
| 2011/0004276 A1 | 1/2011 | Blair et al. |
| 2011/0148579 A1 | 6/2011 | Strzelczyk et al. |
| 2012/0024864 A1 | 2/2012 | Champ |
| 2013/0126682 A1 | 5/2013 | Tholkes et al. |
| 2014/0028444 A1 | 1/2014 | Volpi et al. |
| 2014/0077050 A1 | 3/2014 | Huang |
| 2014/0091910 A1 | 4/2014 | Volpi et al. |
| 2014/0148095 A1 | 5/2014 | Smith et al. |
| 2014/0360412 A1 | 12/2014 | Zaccai et al. |
| 2015/0162957 A1 | 6/2015 | Saghbini et al. |
| 2015/0297307 A1 | 10/2015 | Sweeney |
| 2015/0304478 A1 | 10/2015 | Kim et al. |
| 2016/0070942 A1 | 3/2016 | Dor et al. |
| 2016/0292980 A1 | 10/2016 | H. Kazerouni |
| 2017/0195308 A1 | 7/2017 | Marka et al. |
| 2017/0258547 A1 | 9/2017 | Karasina |
| 2018/0039753 A1 | 2/2018 | Blair et al. |
| 2018/0285704 A1 | 10/2018 | Stewart et al. |
| 2018/0333309 A1 | 11/2018 | Merritt et al. |
| 2018/0353256 A1 | 12/2018 | Stewart et al. |
| 2018/0361033 A1 | 12/2018 | Reasoner et al. |
| 2019/0217352 A1 | 7/2019 | Maness et al. |
| 2020/0222009 A1 | 7/2020 | Al-Ali et al. |

(56) References Cited

U.S. PATENT DOCUMENTS

2020/0405403 A1    12/2020    Shelton, IV et al.
2022/0317827 A1    10/2022    Paramasivan et al.

FOREIGN PATENT DOCUMENTS

| | | |
|---|---|---|
| CN | 105640093 A | 6/2016 |
| CN | 106102635 A | 11/2016 |
| CN | 106263557 A | 1/2017 |
| CN | 109179243 A | 1/2019 |
| CN | 109247989 A | 1/2019 |
| CN | 111741725 A | 10/2020 |
| EP | 0199079 A1 | 10/1986 |
| EP | 3363402 A1 | 8/2018 |
| WO | 2004047660 A1 | 6/2004 |
| WO | 2007070570 A2 | 6/2007 |
| WO | 2014066337 A2 | 5/2014 |
| WO | 2014182701 A1 | 11/2014 |
| WO | 2017112684 A1 | 6/2017 |
| WO | 2018014219 A1 | 1/2018 |
| WO | 2019222655 A2 | 11/2019 |

OTHER PUBLICATIONS

Akgun, Mete et al., "Attacks and Improvements to Chaotic Map-Based RFID Authentication Protocol", Security and Communication Networks, vol. 8, 2015, pp. 4028-4040.

Burmester, Mike et al., "RFID Security: Attacks, Countermeasures and Challenges", Computer Science Department, Florida State University, 2007, 10 pages.

Duc, Dang Nguyen et al., "Enhancing Security of EPCglobal Gen-2 RFID Tag Against Traceablity and Cloning", The 2006 Symposium on Cryptography and Information Security, Japan, Jan. 17-20, 2006, The Institute of Electronics, Information and Communication Engineers, 6 pages.

English language abstract and machine-assisted English translation for CN 105640093 A extracted from espacenet.com database on Feb. 18, 2021, 8 pages.

English language abstract and machine-assisted English translation for CN 106263557 A extracted from espacenet.com database on Feb. 18, 2021, 6 pages.

English language abstract and machine-assisted English translation for CN 109179243 A extracted from espacenet.com database on Feb. 18, 2021, 9 pages.

English language abstract and machine-assisted English translation for CN 109247989 A extracted from espacenet.com database on Feb. 18, 2021, 17 pages.

English language abstract and machine-assisted English translation for CN 201840835 U extracted from espacenet.com database on Feb. 18, 2021, 6 pages.

English language abstract and machine-assisted English translation for WO 2018/014219 A1 extracted from espacenet.com database on Feb. 18, 2021, 6 pages.

English language abstract for CN 106102635 A extracted from espacenet.com database on Feb. 18, 2021, 2 pages.

English language abstract for CN 111741725 A extracted from espacenet.com database on Sep. 29, 2021, 2 pages.

English language abstract for CN 203005496 U extracted from espacenet.com database on Feb. 18, 2021, 1 page.

English language abstract for EP 0 199 079 A1 extracted from espacenet.com database on Feb. 18, 2021, 1 page.

Fujitsu, Specification of 1KBytes UHF Band RFID Chip, Document No. 20130531-01F, Rev. 001, May 31, 2013, 37 pages.

GS1 EPCGLOBAL, "Specification for EPC HF RFID Air Interface", Version 2.0.3, Sep. 5, 2011, 131 pages.

Hutter, Michael et al., "On the Security of RFID Devices Against Implementation Attacks", Int. J. Security and Networks, vol. 5, Nos. 2/3, 2010, pp. 106-118.

Hutter, Michael et al., "RFID and Its Vulnerability to Faults", Institute for Applied Information Processing and Communications, 2008, pp. 363-379.

International Patent Application No. PCT/US2022/041636, filed on Aug. 26, 2022.

Kashfi, Hamid, "Evaluation of Practical Attacks Against RFID Technology", Linnaeus Univeristy, Sweden, Oct. 21, 2014, 89 pages.

Lehtonen, Mikko et al., "Securing RFID Systems by Detecting Tag Cloning", Conference Paper, DBLP, May 2009, 19 pages.

Mitrokotsa, Aikaterini et al., "Classifying RFID Attacks and Defenses", Inf. Syst. Front, 2010, vol. 12, pp. 491-505.

Mitton, Nathalie et al., "RFID Middleware: Concepts and Architecture", 2010, 578 pages.

NXP, "SL2S1412; SL2S1512; SL2S1612 Product Data Sheet", ICODE ILT-M, Rev. 3.0—167730, May 2, 2012, 26 pages.

Song, Boyeon et al., "Scalable RFID Security Protocols Supporting Tag Ownership Transfer", Dec. 26, 2009, 27 pages.

Song, Boyeon, "Server Impersonation Attacks on RFID Protocols", Universit of London, Information Security Group, Conference: Mobile Ubiquitous Computing, Systems, Services and Technologies, 2008, 6 pages.

U.S. Appl. No. 17/100,373, filed Nov. 20, 2020.
U.S. Appl. No. 17/100,377, filed Nov. 20, 2020.
U.S. Appl. No. 17/145,223, filed Jan. 8, 2021.
U.S. Appl. No. 17/194,771, filed Mar. 8, 2021.
U.S. Appl. No. 18/103,942, filed Jan. 31, 2023.
U.S. Appl. No. 63/323,677, filed Mar. 25, 2022.

Verdult, Roel et al., "A Toolbox for RFID Protocol Analysis", Institute for Computing and Information Sciences, Radboud University, The Netherlands, Fourth International EUROSIP Workshop on RFID Technology, 2012, 9 pages.

Xiao, Qingham et al., "Chapter 19, RFID Technology, Security Vulnerabilities, and Countermeasures", Supply Chain, the Way to Flat Organisation, Book edited by Yangang Huo, I-Tech, Vienna, Austria, Dec. 2008, pp. 357-382.

\* cited by examiner

MEDICAL WASTE COLLECTION SYSTEMS, MANIFOLDS, AND RELATED METHODS

RELATED APPLICATIONS

The present application is a continuation of U.S. patent application Ser. No. 18/103,942, filed Jan. 31, 2023, which claims priority to and all the benefits of U.S. Provisional Patent Application No. 63/305,267, filed Jan. 31, 2022, the contents of each which are hereby incorporated by reference herein in their entirety.

BACKGROUND

A byproduct of some surgical procedures is the generation of liquid, semisolid, and/or solid waste material. The liquid waste material may include bodily fluids and irrigating solution(s) at the surgical site, and the solid and semisolid waste material may include bits of tissue and pieces of surgical material(s). The medical waste, regardless of its phase, is preferably collected so it neither fouls the surgical site nor becomes a biohazard in the medical suite in which the procedure is being performed.

The medical waste may be removed from the surgical site through a suction tube under the influence of a vacuum provided by a medical waste collection system. One exemplary medical waste collection system is sold under the tradename NEPTUNE by Stryker Corporation (Kalamazoo, Mich.), with certain versions of the medical waste collection system disclosed in commonly owned United States Patent Publication No. 2005/0171495, published Aug. 4, 2005, International Publication No. WO 2007/070570, published Jun. 21, 2007, and International Publication No. WO 2014/066337, published May 1, 2014, the entire contents of each of which are incorporated herein by reference.

SUMMARY

In one aspect, a medical waste collection system includes a medical waste collection device for providing suction at a surgical site, and a manifold releasably couplable to the medical waste collection device. The manifold defines a pathway through which the medical waste collection device is configured to provide suction to the surgical site, and may include an intricate set of features configured to provide optimized operation of the medical waste collection device, and to avoid clogging or compromise of components of the medical waste collection device. The medical waste collection device is configured to control activation of suction based on a proper manifold being present.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
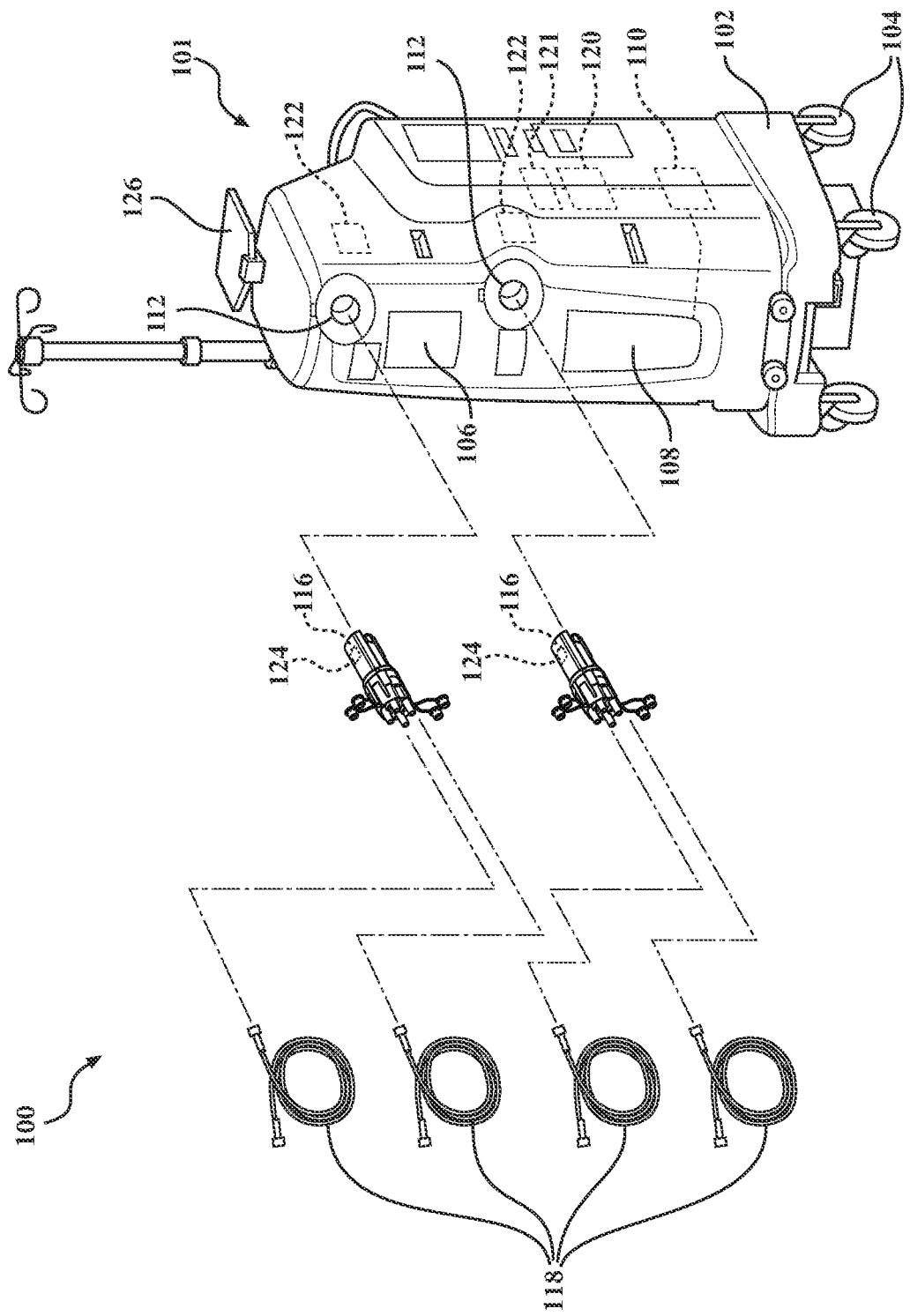
FIG. 1 is a perspective view of a medical waste collection system including a medical waste collection device and two manifolds each configured to be removably inserted into a different receiver of the medical waste collection device.

FIG. 1 illustrates a medical waste collection system 100, such as a surgical waste collection system, for collecting the waste material generated during medical procedures, or more particularly, surgical procedures. The medical waste collection system 100 may collect the waste material and/or store the waste material until it is necessary or desired to off-load and dispose of the waste material. More particularly, the medical waste collection system 100 may include a medical waste collection device 101 (also referred to herein as a "rover") for collecting and storing the waste material, and which may be transported to and operably coupled with a docking station through which the waste material is emptied.

The medical waste collection device 101 may include a base 102 and wheels 104 for moving the medical waste collection device 101 along a floor surface within a medical facility. The medical waste collection device 101 may also include at least one waste container 106, 108 defining a waste volume for collecting and storing the waste material. FIG. 1 shows a first waste container 106 arranged above a second waste container 108 having a relatively greater or larger volume than the first waste container 106. A vacuum pump 110 (shown in phantom) may be supported on the base 102 and configured to draw suction on one or both of the first and second waste containers 106, 108 through one or more vacuum lines. At least one vacuum regulator may also be supported on the base 102 and in fluid communication with the vacuum pump 110 and the waste container(s) 106, 108. The vacuum regulator(s) may be configured to regulate a level of the suction drawn on the waste container(s) 106, 108. Suitable construction and operation of several subsystems of the medical waste collection device 101 may be disclosed in the aforementioned, commonly owned United States Patent Publication No. 2005/0171495, International Publication No. WO 2007/070570, and International Publication No. WO 2014/066337. Suitable construction and operation of several subsystems of the medical waste collection device 101 may also be disclosed in commonly owned International Publication No. WO 2017/112684, published Jun. 29, 2017, the entire contents of which are hereby incorporated herein by reference.

The medical waste collection device 101 may further include at least one receiver 112 supported on the base 102. In a general sense, the receiver(s) 112 may define an opening 114 (see FIG. 2) dimensioned to removably receive at least a portion of a manifold 116, such as a surgical waste collection manifold, in a manner to be described throughout the present disclosure. FIG. 1 shows two receivers 112 with each of the receivers 112 associated with a respective one of the first and second waste containers 106, 108. Alternatively, a single receiver 112 and/or a single manifold 116 may be provided. The receiver(s) 112 may include a suction inlet configured to be arranged in fluid communication with the respective one of the waste containers 106, 108. A suction path may be established from suction tube(s) 118 to the waste containers 106, 108 through the manifold(s) 116 removably inserted into the receiver(s) 112. The vacuum generated by the vacuum pump 110 may be drawn on the suction tube(s) 118, and the waste material at the surgical site may be drawn through the manifold(s) 116, through the suction inlet of the receiver 112, and into the waste container(s) 106, 108.

The medical waste collection device 101 may additionally include a rover controller 120. The rover controller 120 may be configured to control actuation of the medical waste collection device 101. To this end, the rover controller 120 may be in communication with the vacuum pump 110, and may provide for overall control of the medical waste collection device 101. For instance, the rover controller 120 may regulate the on/off operation of the vacuum pump 110, and may also regulate the vacuum flow through the manifold(s) 116. The rover controller 120 may be in communication with a memory device 121 of the medical waste collection device 101. The memory device 121 may store data and computer-executable instructions for authenticating an inserted manifold 116, as described in more detail below.

The medical waste collection device 101 may further include a user interface 126 in operable communication with the rover controller 120. The user interface 126 may be configured to present operational data, accept user inputs, and provide audible tones to a user. For instance, the user interface 126 may include a touchscreen display and a speaker. Surgical personnel may enter commands to regulate the medical waste collection device 101 through the user interface 126, such as by pressing button images presented on the user interface 126.

The medical waste collection device 101 may also include a reader 122 positioned adjacent each receiver 112. The reader 122 may be configured to communicate with an RFID tag 124 of the manifold 116 when the manifold 116 is inserted into the receiver 112. The RFID tag 124 may be coupled to a surface, such as an internal or external surface, of the manifold 116. The rover controller 120 may be in communication with each reader 122, such as through a reader controller 123 (see FIG. 3).

The rover controller 120 (or reader controller 123) may be configured to instruct the reader 122 to repetitively emit a basic interrogation signal for the RFID tag 124. If a manifold 116 is not seated in the receiver 112, the manifold 116, or more particularly the RFID tag 124, may not emit a response to the basic interrogation signal. The rover controller 120 and reader 122 may cooperate to continually interrogate for a manifold 116.

The rover controller 120 may be configured to inhibit activation of the vacuum pump 110 until a manifold 116 has been seated into the receiver 112 and authenticated by the rover controller 120. An authentic manifold 116 may be designed with a specific set of features and subject to stringent manufacturing and quality standards so as to provide optimized operation of the medical waste collection system 100. Such a manifold 116 may also have a limited lifespan. Use of a manifold with the medical waste collection device 101 that lacks such features or is of lesser quality, or use of a manifold beyond its limited lifespan, may adversely affect the performance of the medical waste collection system 100. For instance, such use may result in clogging or other compromise of the components of the medical waste collection system 100, potentially causing reduced suction and/or contamination. The rover controller 120 may thus serve as a master override that prohibits the vacuum pump 110 from being actuated unless, as described below, an appropriate manifold 116 is fitted to the medical waste collection device 101. If the user tries to actuate the vacuum pump 110 without such a manifold 116 being inserted, the rover controller 120 may be configured to prevent activation of the vacuum pump 110. The rover controller 120 may also be configured to cause a warning message to be presented on the user interface 126.

The manifold 116 and receiver 112 may be configured such that, when the manifold 116 is seated in the receiver 112, the reader 122 is within communication range of the RFID tag 124. Once this event occurs and the reader 122 sends an interrogation signal, the RFID tag 124 may send a basic response to the reader 122, which may be forwarded to the rover controller 120 as an indication that a manifold 116 has been inserted. The rover controller 120 may then be configured to proceed to read certain data in a memory device 128 of the RFID tag 124 through the reader 122 (and potentially through the reader controller 123). The rover controller 120 may thereafter be configured to perform an authentication procedure based on the received data.

Figure 2:
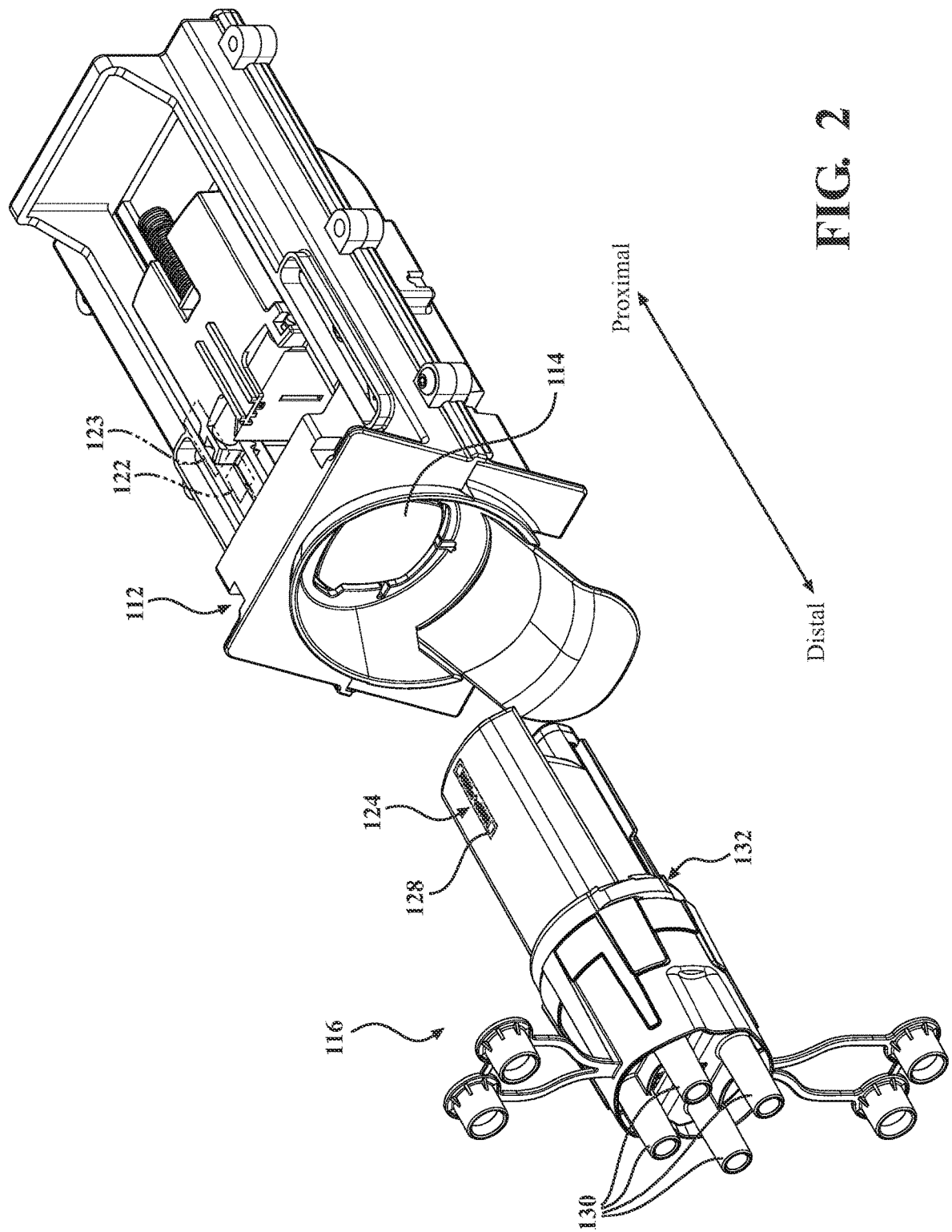
FIG. 2 is a perspective view of the manifold and receiver with the manifold oriented for insertion into an opening of the receiver.
Figure 3:
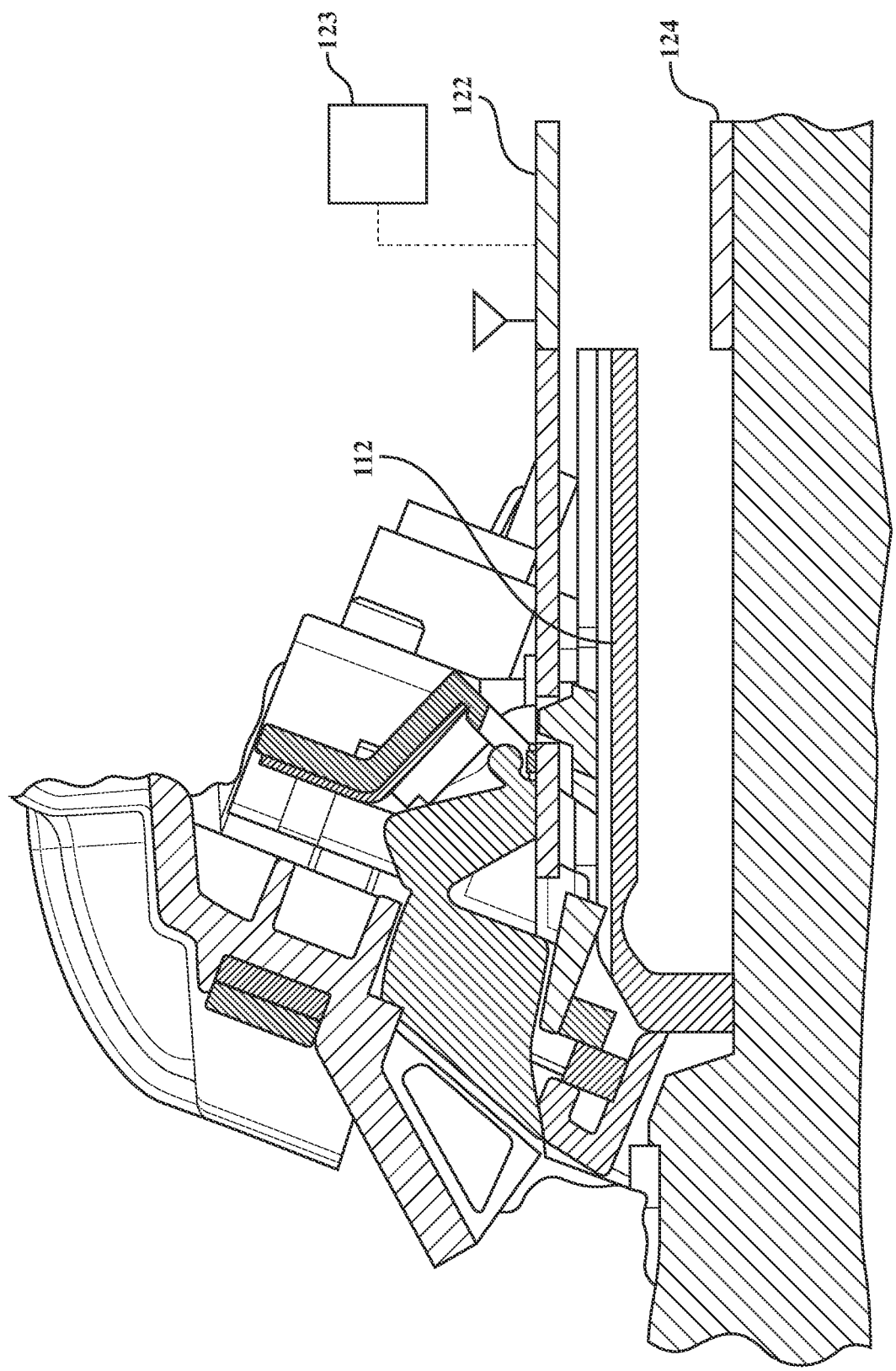
FIG. 3 is a schematic cross-sectional view of the manifold inserted into the receiver with a reader proximate the manifold.

FIG. 2 illustrates the manifold 116 in a decoupled operative position in which the manifold 116 is separate or spaced apart from the receiver 112. FIG. 2 may be representative of the manifold 116 prior to insertion into the receiver 112 and/or after removal of the manifold 116 from the receiver 112. The manifold 116 may be configured to be inserted into the receiver 112 through the opening 114, and the suction tube(s) 118 may be configured to be removably coupled to inlet fitting(s) 130 of the manifold 116. The resulting arrangement is schematically reflected in FIG. 1, in which two suction tubes 118 are coupled to two of four inlet fittings 130 of each of the manifolds 116. Any number of inlet fitting(s) 130 are contemplated, and it is further contemplated that the suction tube(s) 118 may be integral with a housing 132 of the manifold. The aforementioned suction path may thus be established, and an instrument (not shown) coupled to an end of the suction tube(s) 118 opposite the manifold(s) 116 may be directed to the surgical site to collect the waste material under the influence of the vacuum provided by the vacuum pump 110. In FIG. 3, the manifold 116 is shown in a coupled position with the RFID tag 124 within communication range of the reader 122.

Figure 4:
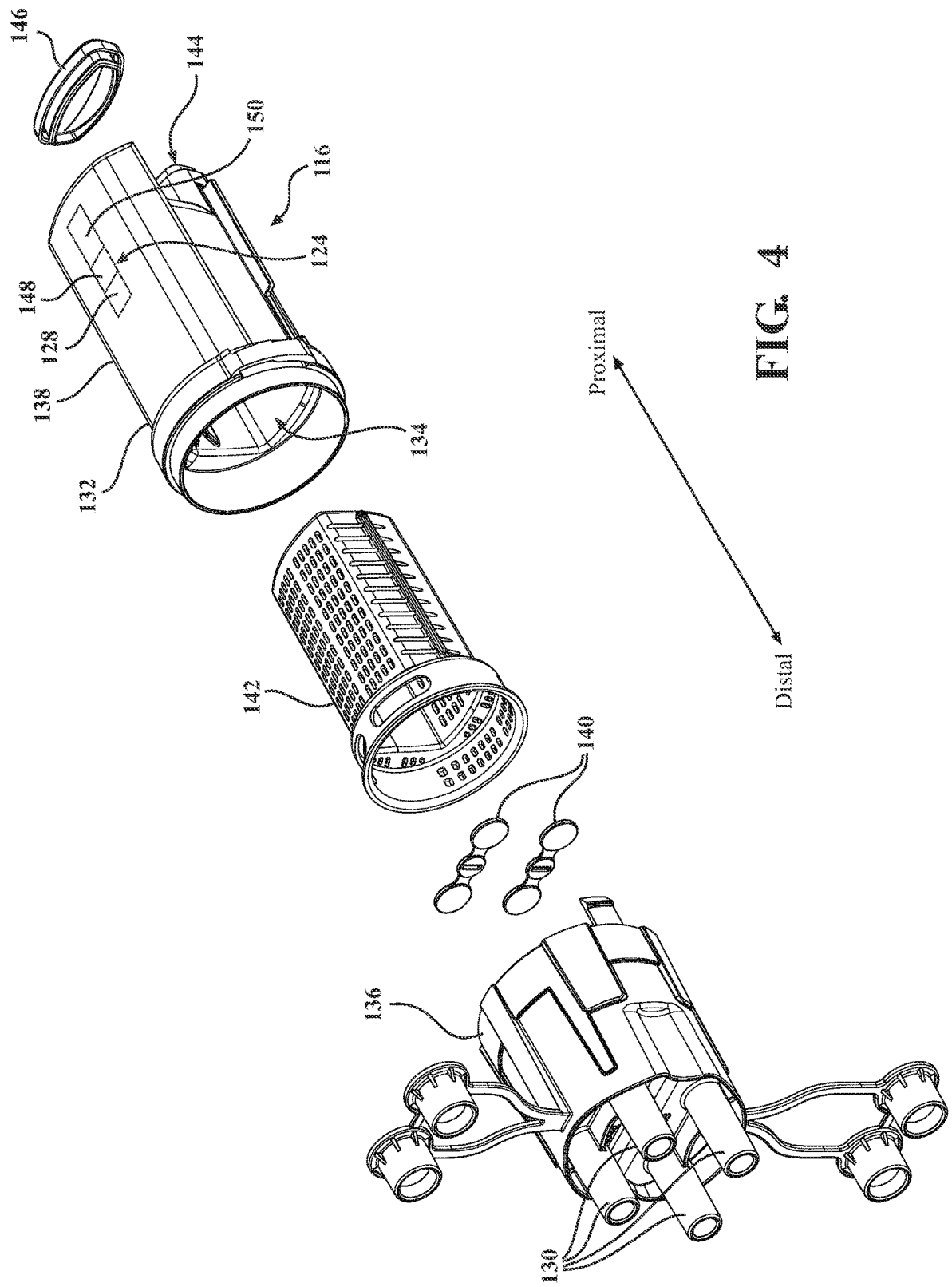
FIG. 4 is an exploded view of the manifold.
Figure 5:
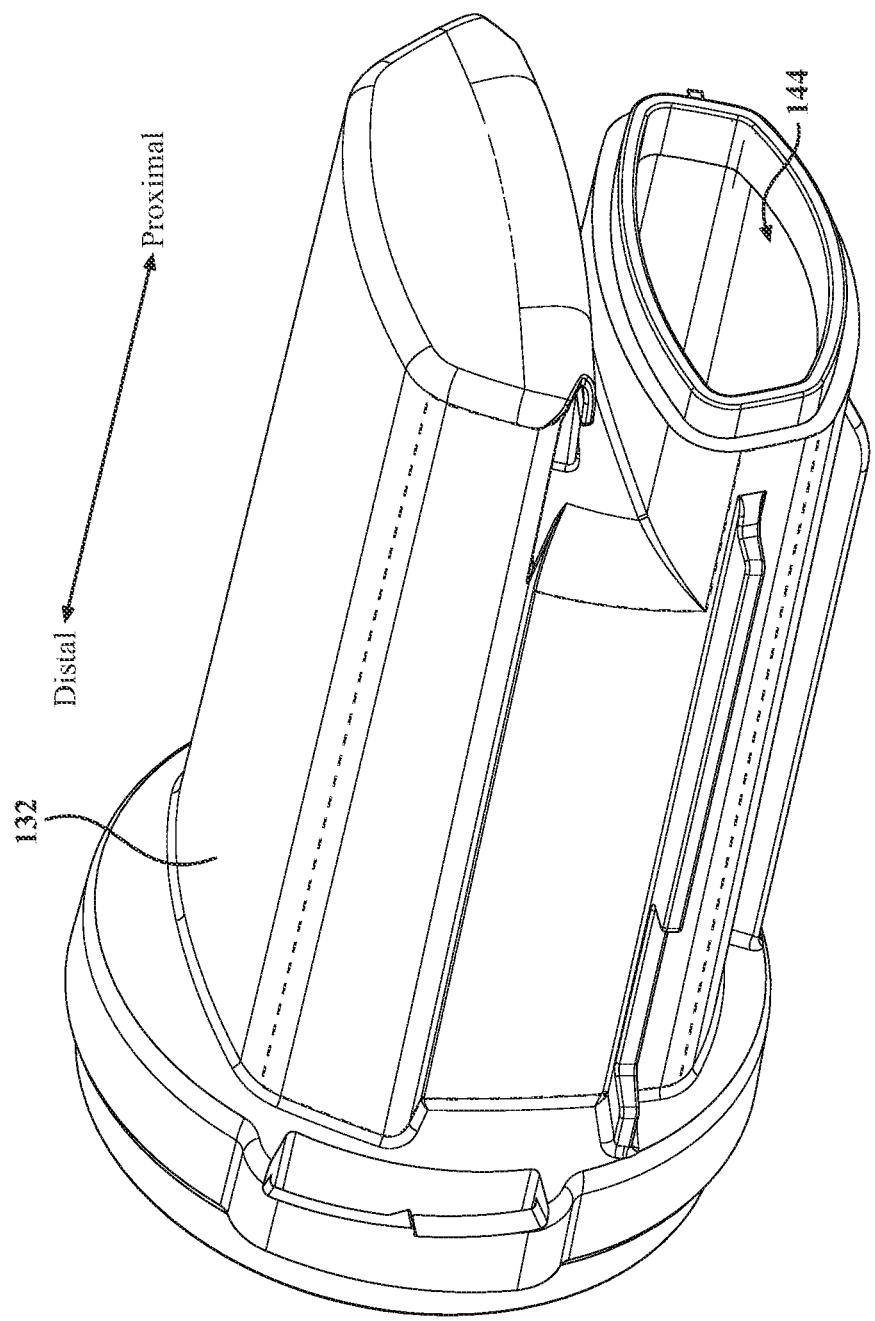
FIG. 5 is a perspective view of the proximal end of the manifold housing.

Referring now to FIGS. 4 and 5, the manifold 116 may include a housing 132 having a proximal region and a distal region and defining an internal fluid pathway between the proximal and distal regions. The housing 132 may define a manifold volume 134 in certain configurations. The housing 132 may be considered any external structure or component of the manifold 116, and more particularly any structure or component that at least partially defines the manifold volume 134. FIG. 4 shows the manifold 116 including a head 136 coupleable to a trunk 138 of the manifold 116 to at least partially form the housing 132. The head 136 may be positioned distal to the trunk 138 when the manifold 116 is oriented for insertion into the opening 114 of the receiver 112, as shown in FIG. 2. Alternatively to a multi-piece construction including the head 136 and the trunk 138, the housing 132 of the manifold 116 may be of unitary or monolithic construction.

The head 136 (or any other portion of the housing 132) may include inlet fitting(s) 130. The inlet fitting(s) 130 may define a distal region of the manifold 116. Alternatively, the inlet fitting(s) 130 may be coupled to a different structure separate from the housing 132 (i.e., not directly coupled to the head 136) with the inlet fitting(s) 130 being in fluid communication with an outlet opening 144 of the manifold 116 to establish the suction path. It is further contemplated that any features described as being a part of the head 136 may alternatively be a part of the trunk 138, and any features described as being a part of the trunk 138 may alternatively be a part of the head 136.

Suitable materials for forming the housing 132 may include polymers, composites, metals, ceramics, and combinations thereof. Such materials include sufficient anticorrosive properties to avoid degradation when exposed to the waste material and sufficient mechanical properties to maintain integrity under the vacuum levels to be provided by the medical waste collection device 101. The polymers of polyethylene, polypropylene, polyvinyl chloride, polyethylene terephthalate (PET, PETE), polystyrene, polycarbonate, and poly(methyl methacrylate) may be particularly well suited for the manifold 116 in low-cost and disposable implementations. The manifold 116 may be formed using an injection-molding process.

The manifold 116 may include at least one valve 140 configured to prevent backflow from the manifold volume 134 through the inlet fittings 130. During assembly of the manifold 116, the valve(s) 140 may be coupled to the housing 132, and more particularly to the head 136. The sealing of the proximal end of the inlet fittings 130 may prevent backflow from the manifold volume 134 through the inlet fittings 130, and may thus prevent possible egress of the waste material through the inlet fittings 130.

The manifold 116 may further include a filter element 142 disposed within the manifold volume 134. The filter element 142, in a broad sense, may include structures configured to capture or collect the semisolid or solid waste material entrained within the liquid waste material being drawn through the manifold 116 under the influence of the vacuum provided by the medical waste collection device 101.

The manifold 116 may define an outlet opening 144 at a proximal region of the housing 132 that is in fluid communication with the manifold volume 134. During operation of the medical waste collection system 100, medical waste fluid may flow through the inlet fittings 130 into the manifold volume 134 and out through the outlet opening 144 into one or more of the first waste container 106 and the second waste container 108.

A drip seal 146 may be in sealing communication with the outlet opening 144 of the manifold 116. The drip seal 146 may function to seal with a complementary sealing surface of an inlet mechanism including the suction inlet integral with the medical waste collection device 101. The drip seal 146 may be of unitary or monolithic construction or be a multi-piece component. The drip seal 146 may be formed of a polymeric material with suitable hardness and resiliency, for example, a rubber or plastic having a Shore A Hardness within the range of approximately 20 to 90 durometers, and more particularly within the range of approximately 35 to 75 durometers, and even more particularly within the range of approximately 50 to 60 durometers.

Various other features of the manifold 116 and the medical waste collection device 101 are contemplated. To that end, the disclosures of International Publication No. WO 2019/222655, published Nov. 21, 2019, and U.S. Pat. No. 10,471,188, issued Nov. 12, 2019, are each hereby incorporated by reference herein in their entirety.

The RFID tag 124, including the memory device 128, may be coupled to an internal or external surface of the housing 132 of the manifold 116, and may be positioned to be detected by the reader 122 of the medical waste collection device 101 when the manifold 116 is seated in the receiver 112. As illustrated in the example of FIG. 4, the RFID tag 124 may be disposed on the upper wall of the housing 132. The upper wall may be generally horizontally-oriented when the manifold 116 is oriented for insertion into the receiver 112.

The RFID tag 124 may be configured such that the RFID tag 124 is detectable by the reader 122 when the manifold 116 is in the fully inserted operative position within the receiver 112. More specifically, the RFID tag 124 and reader 122 may be positioned such that the RFID tag 124 is only detectable when the manifold 116 is in the fully inserted operative position within the receiver 112 (e.g., is in fluid communication with the first waste container 106 and/or the second waste container 108). Should an article be incapable of being inserted into the fully inserted operative position, such as because such article does not conform to the shape of the opening 114 of the receiver 112, no data communication may be established between the RFID tag 124 and the reader 122, and the rover controller 120 may prevent operation of the medical waste collection device 101.

Figure 6:
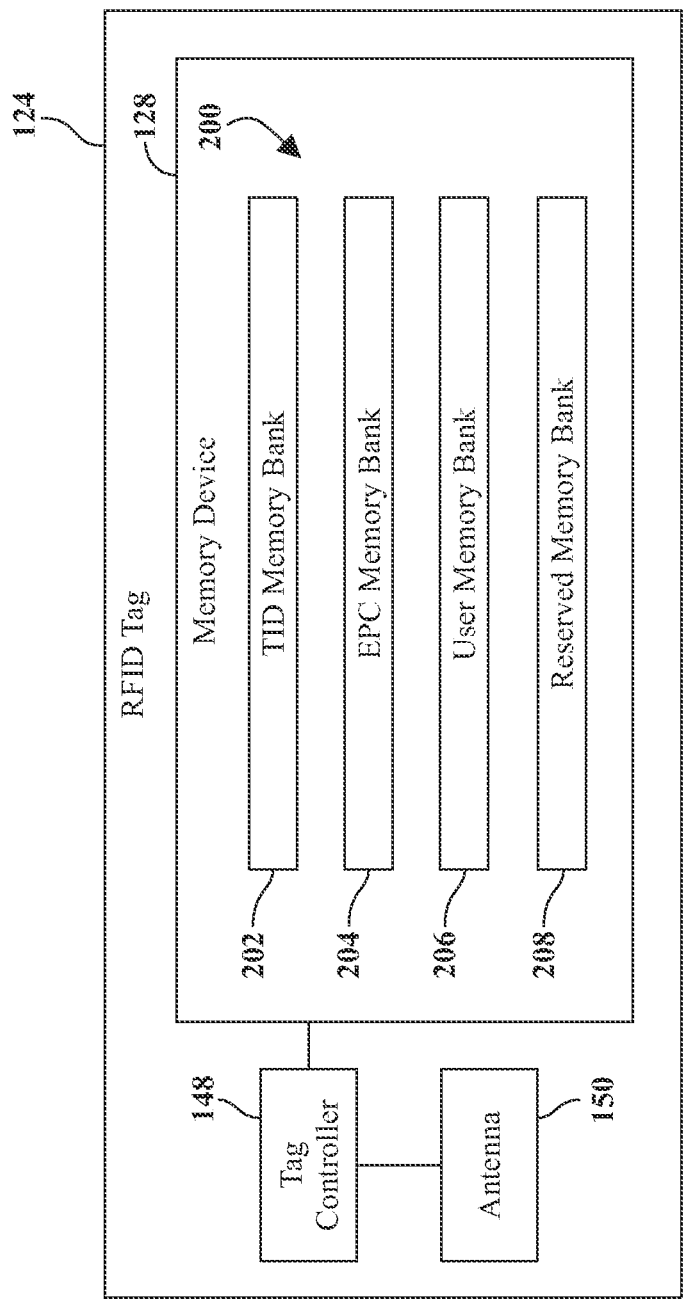
FIG. 6 is a schematic view of an RFID tag that may be coupled to the manifold housing for authenticating the manifold.

Referring now to FIG. 6, the RFID tag 124 may include a tag controller 148 in communication with the memory device 128. The RFID tag 124 may further include an antenna 150 coupled to the tag controller 148, such as to allow communication between the rover controller 120 and the tag controller 148 via the reader 122.

Generally, the memory device 128 may store data for determining whether the manifold 116 is usable with the medical waste collection device 101, including data indicating whether the manifold 116 is authentic. The memory device 128 may be NOVRAM or EEPROM. Alternatively, the memory device 128 may be any form of computer-readable storage media. Computer-readable storage media as used herein may refer to a solid-state storage, or any available storage media that can be accessed by the tag controller 148. That is, computer readable storage media includes non-transitory, volatile and non-volatile, removable and nonremovable media implemented in any method or technology for storage of information such as computer-readable instructions, data structures, program modules or other data. For example, computer-readable storage media may include RAM, ROM, EPROM, EEPROM, flash memory, other solid state memory technology, or any other medium which can be used to store the desired information, and which can be accessed by tag controller 148. The memory device 121 of the medical waste collection device 101 may similarly be any form of computer-readable storage media as described above.

The tag controller 148 may generally be configured to implement the functions, features, and processes of the RFID tag 124 described herein. For instance, the tag controller 148 may be configured to respond to interrogation signals received from the rover controller 120 of the medical waste collection device 101, such as via the reader 122 and antenna 150. The tag controller 148 may also be configured to execute commands received from the rover controller 120 relating to the memory device 128, such as read and write commands, lock and unlock commands, lock status inquiry commands, and recommission commands, each of which is described in more detail below.

In some implementations, each of the rover controller 120 and the tag controller 148 may include a processor programmed to implement the functions, features, and processes of the controller described herein. More specifically, the processor may be configured to operate under control of computer-executable instructions residing in a non-volatile storage of the controller, such as by being configured to read into volatile storage (e.g., RAM) and execute such computer-executable instructions. The computer-executable instructions may embody software programs, and may be compiled or interpreted from a variety of programming languages and/or technologies, including, without limitation, and either alone or in combination, Java, C, C++, C#, Objective C, Fortran, Pascal, Java Script, Python, Perl, and PL/SQL. As some examples, the processor may include one or more devices selected from microprocessors, microcontrollers, digital signal processors, microcomputers, central processing units, field programmable gate arrays, programmable logic devices, state machines, logic circuits, analog circuits, digital circuits, or any other devices that manipulate signals (analog or digital) based on operational instructions read from the non-volatile storage of the controller.

The memory device 128 of the RFID tag 124 may include one or more memory banks 200 for storing data to be read by the medical waste collection device 101, or more particularly the rover controller 120, when the manifold 116 is seated in the receiver 112. More particularly, the RFID tag 124 may include at least two memory banks 200, or even more specifically may include four memory banks 200. Each memory bank 200 may be a distinct structural or logical unit of storage within the memory device 128. The RFID tag 124 may be configured such that only one memory bank 200 is accessed in a given read or write operation executed by the tag controller 148. Each read or write operation received by the RFID tag 124, such as from the rover controller 120, may thus implicate the bits of only one of the memory banks 200.

For example, the memory banks 200 may include at least one of a tag identification (TID) memory bank 202 for storing manufacture data relating to the RFID tag 124, such as an identifier unique to the RFID tag 124; an electronic product code (EPC) memory bank 204 for storing electronic identification data relating to the manifold 116 to which the RFID tag 124 is affixed; a user memory bank 206 for storing use history data relating to the manifold 116 to which the RFID tag 124 is affixed; and a reserved memory bank 208 for storing passwords for the RFID tag 124. Each of these memory banks 200 may be of a limited size to minimize the footprint of the RFID tag 124. For example, the TID memory bank 202 may have a capacity of 96 bits, the EPC memory bank 204 may have a capacity of 304 bits, the user memory bank 206 may have a capacity of 512 bits, and the reserved memory bank 208 may have a capacity of 64 bits. As described in more detail below, the rover controller 120 may be configured to authenticate the manifold 116 to which the RFID tag 124 is affixed based on authentication data stored across two or more of the above memory banks 200, with the data being stored in a specific manner that enables multiple levels of authentication while also providing capacity for storage of other data related to operation of the manifold 116 and RFID tag 124. For instance, as one level of authentication, the RFID tag 124 may include an originality signature unique to the manifold 116 that is generated using an authentication algorithm, split into multiple portions, and stored across at least two of the memory banks 200.

The memory device 128 may also store data indicative of whether the RFID tag 124 has been previously recommissioned. As described in more detail below, one or more of the memory banks 200, such as the TID memory bank 202, the EPC memory bank 204, and/or the user memory bank 206, may be locked in non-permanent read-only state. The status of a memory bank 200 as being locked in such a state may be indicated in the EPC memory bank 204 and enforced by the tag controller 48. When a memory bank 200 is in such a locked state, the tag controller 148 may be configured to execute read commands against the memory bank 200, but not write commands. In other words, write commands received from the rover controller 120 against such a memory bank 200 may fail.

Recommissioning the RFID tag 124 may function to unlock a memory bank 200 locked in a non-permanent read-only state, and may be performed by providing a recommission command to the tag controller 148. Responsive to receiving the recommission command, the tag controller 148 may be configured to store data in the memory device 128 indicating that the RFID tag 124 has been recommissioned, and to transition the memory banks 200 locked in a non-permanent read-only state to an unlocked writeable state. As noted below, in some implementations, the data indicative of an executed recommission may be stored in one or more of the memory banks 200, such as the EPC memory bank 204.

Figure 7:
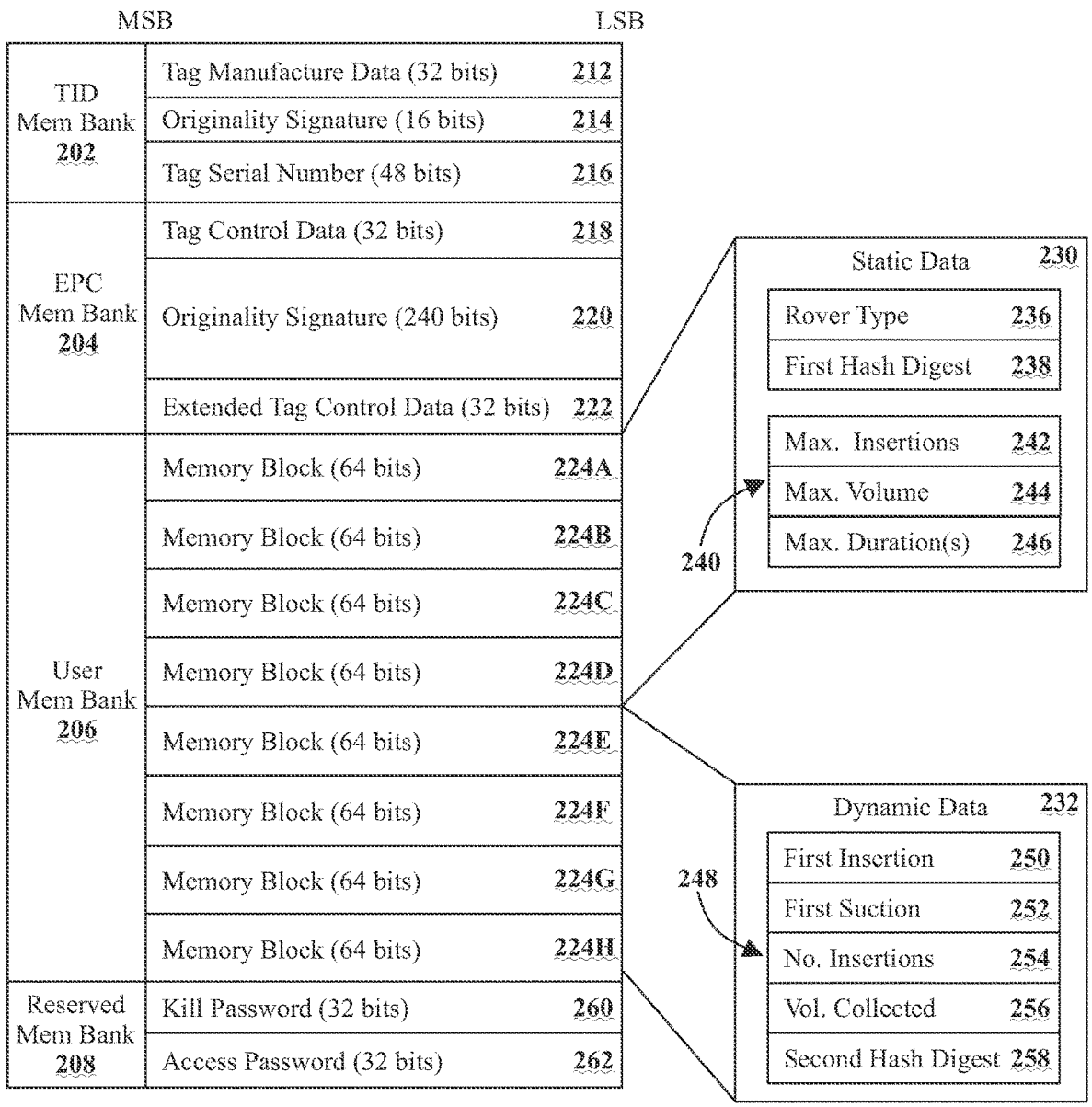
FIG. 7 is a schematic view of data that may be stored in the RFID tag for authenticating the manifold.

FIG. 7 illustrates data that may be stored in each of the memory banks 200 of the RFID tag 124. As shown in the illustrated example, the TID memory bank 202 may store tag manufacture data 212, a portion of an originality signature 214, and a tag serial number 216. The tag manufacture data 212 may include data relating to manufacture of the RFID tag 124, such as one or more of an allocation class identifier, a mask designer identifier, a tag model number, and other datums indicating whether the RFID tag 124 implements certain features. The tag manufacture data 212 may be 32 bits in length, and may be located in bits $00_h$ to $1f_h$ of the TID memory bank 202.

The portion of the originality signature 214 stored in the TID memory bank 202 may in combination with other data stored in the memory banks 200 form an originality signature unique to the manifold 116 to which the RFID tag 124 is affixed. The originality signature, described in more detail below, may be used by the rover controller 120 to authenticate the manifold 116. The portion of the originality signature 214 stored in the TID memory bank 202 may have a character length of 16 bits, and may be stored in bits $20_h$ to $2F_h$ of the TID memory bank 202.

The tag serial number 216 may be unique to the RFID tag 124, and may be generated and assigned to the RFID tag 124 by the tag manufacturer. The tag serial number 216 may be 48 bits in length, and may be stored in bits $30_h$ to $5F_h$ of the TID memory bank 202. Taken together, the above components of the TID memory bank 202 may form a unique sequence of bits specific to the manifold 116.

The EPC memory bank 204 may store tag control data 218, another portion of the originality signature 220, and extended tag control data 222. The tag control data 218 may include data relating to characteristics of the RFID tag 124 and that facilitates interaction with the RFID tag 124, such as at least one of a cyclic redundancy check code, the length of the EPC memory bank 204, an indicator designating whether the RFID tag 124 includes user memory, an indicator designating whether the RFID tag 124 has been recommissioned, and a tag application indicator. The tag controller 148 may be configured to populate the bits of the tag control data 218 automatically upon operation of the RFID tag 124, such as based on other data stored in the RFID tag 124 and/or commands received by the tag controller 148. The tag control data 218 may be 32 bits in length, and may be stored in bits $00_h$ to $1f_h$ of the EPC memory bank 204.

The portion of the originality signature 220 stored in the EPC memory bank 204 may in combination with the portion of the originality signature 214 stored in the TID memory bank 202 form the originality signature unique to the manifold 116 to which the RFID tag 124 is affixed as described above. The portion of the originality signature 220 stored in the EPC memory bank 204 may have a character length of 240 bits, and may be stored in bits $20_h$ to $10f_h$ of the EPC memory bank 204.

The extended tag control data 222 may include further control data supplementing that of the tag control data 218, such as data indicative of whether the tag has been recommissioned and/or data indicative of the effect of a previously executed recommission on the RFID tag 124. The extended tag control data 222 may be 32 bits in length, and may be stored in bits $110_h$ to $12F_h$ of the EPC memory bank 204.

The user memory bank 206 may store user data read by the rover controller 120 to determine whether the manifold 116 is compatible with the medical waste collection device 101, and also to check that the manifold 116 is not being operated past its functional lifespan. The user memory bank 206 may include multiple memory blocks 224 across which such data is stored. Each memory block 224 may be 64 bits in length, or eight bytes.

In some implementations, the user data stored in the user memory bank 206 may include static data 230 and dynamic data 232. The static data 230 may include data that is programmed to the RFID tag 124 prior to use of the manifold 116 with a medical waste collection device 101, and may not be changed as a function of use of the manifold 116 with a medical waste collection device 101.

For instance, the static data 230 may include a rover type datum 236 (also referred to herein as a "medical waste collection device type datum") and a first hash digest 238 generated based on the rover type datum 236 and/or a first randomized data set, which may also be stored in the user memory bank 206. The rover type datum 236 may designate the type of medical waste collection device 101 for which the manifold 116 is suited. As an example, it is contemplated that certain manifold designs may only be usable with certain configurations of the medical waste collection device 101, such as an obstetrics waste collection device, an endoscopic waste collection device, or a general surgery waste collection device. Additionally or alternatively, the rover type datum 236 may designate a capacity for a medical waste collection device 101 usable with the manifold 116, such as 20 liters, 30 liters, etc.

Additionally or alternatively, the static data 230 may include threshold data 240. The threshold data 240 may include one or more non-zero threshold datums corresponding to an expected functional lifespan of the manifold 116. For instance, the threshold data 240 may include a maximum insertions datum 242, a maximum volume datum 244, and a maximum duration(s) datum 246. The maximum insertions datum 242 may indicate a number of times that the manifold 116 can be inserted into a receiver 112 before the rover controller 120 triggers a certain response, such as preventing the vacuum pump 110 from operating with the manifold 116 and/or causing the user interface 126 to indicate that the number of actual insertions exceeds the number of insertions permitted. The maximum volume datum 244 may designate an amount of fluid than can be channeled through the manifold 116 in question into the one or more waste containers 106, 108 before the rover controller 120 triggers a response, such as that described above. The maximum duration(s) datum 246 may indicate at least one of an expiration date of the manifold 116, a duration from a first insertion of the manifold 116, and a duration from a first suction of the manifold 116 before the rover controller 120 triggers a response, such as that described above.

The dynamic data 232 stored in the user memory bank 206 may include data that is updated as a function of use of the manifold 116 with the medical waste collection device 101. For instance, the dynamic data 232 may include use history data 248 that may be written by the rover controller 120 to track use of the manifold 116. The use history data 248 may include one or more of a first insertion datum 250 indicating a date and/or time in which the manifold 116 is first inserted into the medical waste collection device 101; a first suction datum 252 indicating a date and/or time in which suction is first applied through the manifold 116; a number of insertions datum 254 tracking the number of times that the manifold 116 has been inserted into a receiver 112; and a volume collected datum 256 indicating the amount of fluid that has been channeled through the manifold 116 into one or more of the waste containers 106, 108. Each of these datums may operate to ensure that the manifold 116 is not used beyond its expected functionality due to deterioration in the performance of one or more of the seals and/or valves of the manifold 116, which correspondingly ensures that the manifold 116 and the medical waste collection device 101 each performs as expected during the surgical/medical procedures. Prior to a first use of the manifold 116, each of these datums may be provided with a default value, such as zero. The dynamic data 232 may further include a second hash digest 258 generated based on the use history data 248 and/or a second randomized data set, which may also be stored in the user memory bank 206.

Prior to operating the vacuum pump 110 to draw suction through the manifold 116, the rover controller 120 may be configured to read and compare the threshold data 240 with the use history data 248 to determine whether the manifold 116 has reached or exceeded its expected lifespan. For instance, the rover controller 120 may be configured to read and compare the maximum volume datum 244 with the volume collected datum 256, may be configured to read and compare the maximum duration(s) datum 246 with one or more of a current date, the first insertion datum 250, and the first suction datum 252, and/or may be configured to read and compare the maximum insertions datum 242 with the number of insertions datum 254. To the extent any one of these comparisons indicates that the value of a datum of the use history data 248 is equal to or exceeds the value of a corresponding datum of the threshold data 240, the rover controller 120 may be configured to trigger a response, such as that described above.

In some implementations, the static data 230 and the dynamic data 232 may be stored in distinct memory blocks 224, such as to enable the memory blocks 224 including static data 230 to be locked in a permanent read-only state, as described in more detail below. For instance, the static data 230 may be stored among memory blocks 224A, 224B, 224C, 224D, and the dynamic data 232 may be stored among memory blocks 224E, 224F, 224G, 224H.

The reserved memory bank 208 may store a non-zero kill password 260 and/or a non-zero access password 262 programmed to the RFID tag 124. The kill password 260 may be used to execute various actions, such as recommissioning the RFID tag 124 and rendering the RFID tag 124 permanently nonresponse. In particular, to effect a recommission of the RFID tag 124, the kill password 260 may be submitted along with the recommission command to the RFID tag 124, which may be configured to verify the submitted kill password 260 against the data in the reserved memory bank 208 as a condition of executing the recommission command. Similarly, to effect rendering the RFID tag 124 as permanently responsive, the kill password 260 may be submitted along with the kill command to the RFID tag 124, which may be configured to verify the kill password 260 against the data in the reserved memory bank 208 as a condition of executing the kill command. The kill password 260 may be 32 bits in length, and may be stored in bits $00_h$ to $1f_h$ of the reserved memory bank 208. If no kill password 260 is programmed for the RFID tag 124, then these bits of the reserved memory bank 208 may be set to a default value such as zero, and the RFID tag 124 may be configured to execute the recommission and kill commands without the submission of a password.

The access password 262 may enable the RFID tag 124 to be selectively transitioned between an open state and a secured state, the latter state offering additional permissions and/or commands that are not available in the former state. As an example, in the open state, memory banks 200 locked in one type of non-permanent read-only state, referred to herein as the reversible read-only state, may be read-only. In the secured state, these memory banks 200 may be writeable, and further may be able to be transitioned to an unlocked writeable state effective in both the open and secured states. Conversely, memory banks 200 locked in another type of non-permanent read-only state, referred to herein as the semi-permanent read-only state, may be read-only in both the open and secured states. The access password 262 may be 32 bits in length, and may be stored in bits $20_h$ to $3f_h$ of the reserved memory bank 208. If a non-zero access password 262 is not programmed into the reserved memory bank 208, then the RFID tag 124 may be configured to default to the secured state upon being initiated by interrogation, and these bits of the reserved memory bank 208 may be set to a default value such as zero. Conversely, if a non-zero access password 262 is programmed to the reserved memory bank 208, then the RFID tag 124 may be configured to default to the open state upon being initiated by interrogation.

The above-described structure of the memory device 128 may enable the rover controller 120 to perform multiple interrelated layers of authentication of the manifold 116. For instance, the originality signature may be generated by applying data stored in the RFID tag 124 to various authentication algorithms, such as an Elliptic Curve Digital Signature Algorithm (ECDSA). As one example, the originality signature may be generated by applying the sequence of bits of the TID memory bank 202, with the bits corresponding to the portion of the originality signature 214 masked to a default value (e.g., zero), and a private key to a signature generator function of an authentication algorithm. Even in the absence of the portion of the originality signature 214, the bits of the TID memory bank 202 of a given RFID tag 124 may be unique to that RFID tag 124. Accordingly, the originality signature generated for each manifold 116 based on such bits may be unique to that manifold 116. In other words, given a set of manifolds 116 for use with the medical waste collection device 101, the originality signature stored in the RFID tag 124 of each manifold 116 may differ from that stored in the other manifold(s) 116 of the set.

Once generated, the originality signature for a given manifold 116 may be split into multiple portions and stored in the TID memory bank 202 and EPC memory bank 204 as the portion of the originality signature 214 and the portion of the originality signature 220 respectively. Hence, as one layer of authentication, responsive to the manifold 116 being seated in the receiver 112, the rover controller 120 may be configured to read the portions of the originality signature 214 and 220 from the TID memory bank 202 and EPC memory bank 204 respectively, compile the originality signature based on the read data, and to verify the originality signature with the verification function of the authentication algorithm used to generate the originality signature. If the originality signature passes verification, then the rover controller 120 may be configured to determine that the manifold 116 passes one level of authentication.

As a further layer of authentication, the rover controller 120 may be configured to verify the user data stored in the user memory bank 206. As previously described, the user memory bank 206 may include a first hash digest 238 generated based on the rover type datum 236, and may include a second hash digest 258 generated based on one or more datums of the use history data 248 stored in the user memory bank 206. Thus, responsive to the manifold 116 being seated in the receiver 112, the rover controller 120 may be configured to read this data from the user memory bank 206, and to hash the rover type datum 236 and one or more datums of the use history data 248 to generate first and second hash digests respectively. The rover controller 120 may then be configured to compare the same with the first and second hash digests 238, 258 read from the user memory bank 206 respectively, and to determine that the manifold 116 passes a further level of authentication if the comparison indicates a match.

As yet another layer of authentication, the rover controller 120 may be configured to check the lock status of the memory banks 200 and/or the memory blocks 224 of the memory device 128 against a predefined lock pattern, which may be stored in the memory device 121 of the medical waste collection device 101. The predefined lock pattern, an example of which is described below, may indicate which memory banks 200 and/or memory blocks 224 should and should not be locked in a read-only state, and also the type of read-only locked state that the memory banks 200 and/or memory blocks 224 should be locked in. For instance, the predefined lock pattern may designate one or more of the memory blocks 224 as being locked in a permanent read-only state that is not affected by recommissioning of the RFID tag 124, may designate one or more of the memory banks 200 as being locked in a reversible read-only state that is effective in the open but not secured states of the RFID tag 124, and one or more of the memory banks 200 being locked in a semi-permanent read-only state that is effective in both the open and secured states of the RFID tag 124. Memory banks 200 locked in the reversible and semi-permanent states may both be transitioned to an unlocked writable state through execution of the recommission command by the RFID tag 124. Thus, as a further level of authentication, the rover controller 120 may be configured to verify that the memory banks 200 and/or memory blocks 224 are locked according to the predetermined locked pattern. If so, then the rover controller 120 may be configured to determine that the manifold 116 passes another level of authentication.

Figure 8:
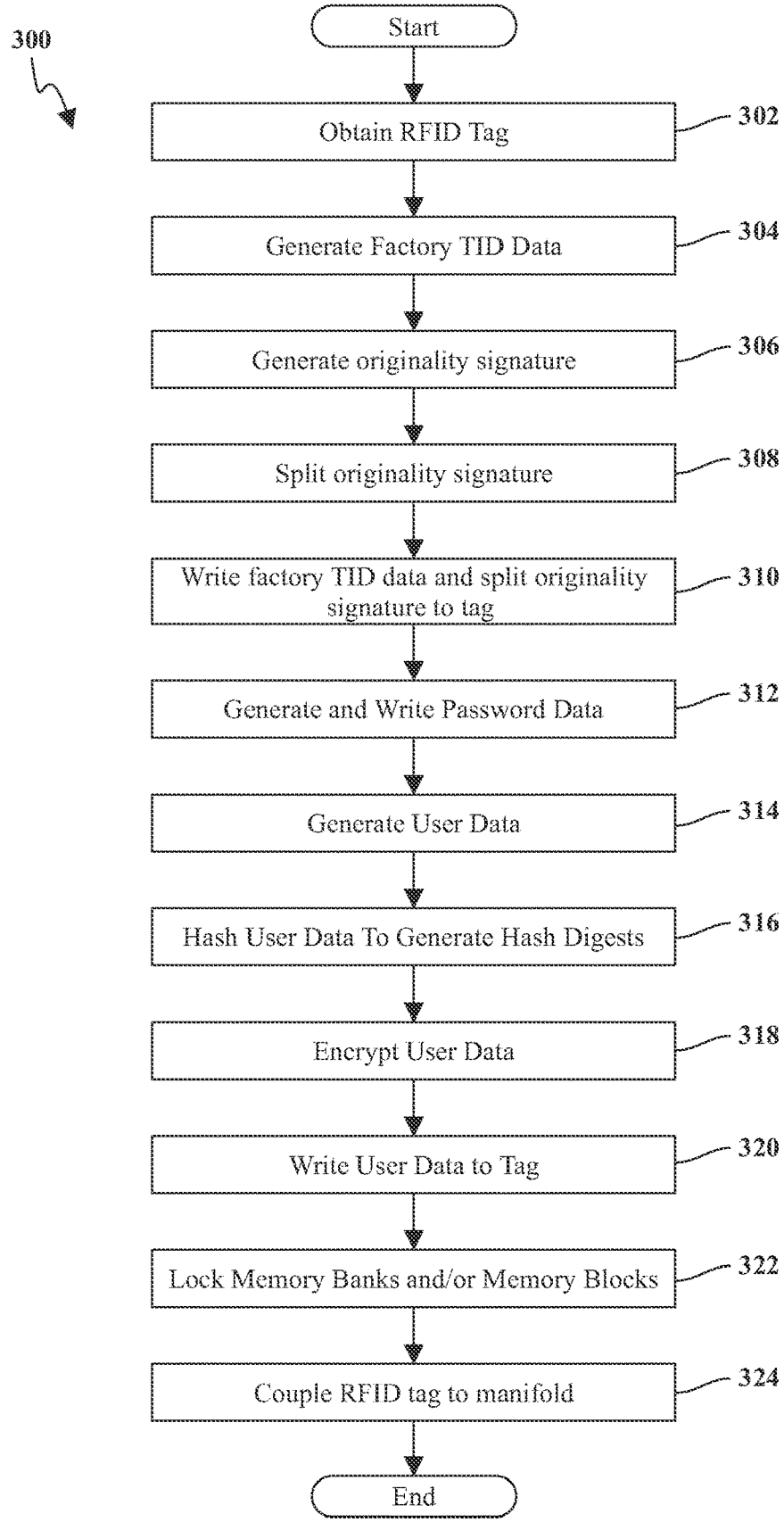
FIG. 8 is a flow chart illustrating a method for programming the RFID tag for authenticating the manifold.

FIG. 8 illustrates a method 300 for programming an RFID tag 124 for a manifold 116. As described above, the manifold 116 may be configured to be coupled to a vacuum inlet integral with a medical waste collection device 101 to provide suction at a surgical site through the manifold 116.

In block 302, an RFID tag 124 may be obtained. The RFID tag 124 may include the structure described above in reference to FIG. 6, and may thus include a memory device 128 containing one or more memory banks 200. At this stage, the memory banks 200 may be empty.

In block 304, factory data for the TID memory bank 202 may be generated. The factory data may generally include data that may be generated by the manufacturer of the RFID tag 124, and may be unrelated to the object to which the RFID tag 124 is to be affixed. For instance, the factory data may include one or more of the tag manufacture data 212 and the tag serial number 216. Alternatively, this data may already have been generated and written to the RFID tag 124 when the RFID tag 124 is obtained, such as by the tag manufacturer.

In block 306, an originality signature may be generated, such as in the manner described above. The originality signature may be unique to the manifold 116 to which the RFID tag 124 is to be affixed, and may be configured to be used by the medical waste collection device 101 to authenticate the manifold 116, such as upon the manifold 116 being proximate the medical waste collection device 101, or more particularly upon insertion of the manifold 116 into the receiver 112 of the medical waste collection device 101. In some examples, the originality signature may be 256 bits. The originality signature may be generated by any suitable authentication algorithm, such as the Elliptic Curve Digital Signature Algorithm (ECDSA).

In block 308, the originality signature may be split into multiple portions (e.g., a first portion and a second portion) for storage in the memory banks 200 of the RFID tag 124. Each of the portions may include a sequence of non-zero characters. For instance, the originality signature may include a sequence of bits identified as the first portion of the originality signature, and may include another sequence of bits identified as the second portion of the originality signature. The sequence of bits identified as the first portion may start at the most significant bit of the originality signature, and the sequence of bits identified as the second portion of the originality signature may follow the sequence of bits identified as the first portion and end at the least significant bit of the originality signature. As an example, the originality signature may be formed by the sequence of bits identified as the second portion being appended to a least significant bit of the sequence of bits identified as the first portion. Alternatively, the originally signature may be formed in reverse, namely, by the sequence of bits identified as the first portion being subsequent to and/or appended to a least significant bit of the sequence of bits identified as the second portion.

Assuming the originality signature is 256 bits in length, in some examples, the sequence of bits identified as the first portion of the originality signature may be 16 bits in length, and the sequence of bits identified as the second portion of the originality signature may be 240 bits in length.

In block 310, the factory TID data and split originality signature may be written to the memory banks 200 of the RFID tag 124. In particular, the factory TID data may be written to the TID memory bank 202 in the bits described above, the first portion of the originality signature may be written to the TID memory bank 202 as the portion of the originality signature 214, and the second portion of the originality signature may be written to the EPC memory bank 204 as the portion of the originality signature 220.

In block 312, password data may be generated and written to the RFID tag 124, or more particularly to the reserved memory bank 208. In particular, a non-zero kill password 260 and non-zero access password 262 may be generated and stored in the reserved memory bank 208. As previously described, the kill password 260 may be submitted along with the recommission command to effect recommissioning of the RFID tag 124, and may be submitted with the kill command to effect rendering the RFID tag 124 permanently nonresponsive.

The access password 262 may be used to selectively transition the RFID tag 124 between an open state and a secured state. The presence of the non-zero access password 262 in the reserved memory bank 208 may cause the RFID tag 124 to upon initiation default to an open state in which both reversible and semi-permanent read-only bank locks are enforced. Responsive to receiving the access password 262 and a command to transition to the secured state, the tag controller 148 may be configured to transition the RFID tag 124 to the secured state in which semi-permanent read-only bank locks continue to be enforced but the reversible read-only bank locks are not. When the RFID tag 124 is in the secured state, the tag controller 148 may also be configured to execute received commands to set memory banks 200 locked in the reversible read-only state to an unlocked writeable state effective in both the open and secured states of the RFID tag 24, but not do the same for memory banks 200 locked in the semi-permanent read-only state. Following the password data being written to the reserved memory bank 208, the reserved memory bank 208 may be locked in a permanent or semi-permanent read-only state, or in a permanent or semi-permanent no read no write state.

The password data may likewise be stored in the memory device 121 of the medical waste collection device 101 so as to enable the rover controller 120 to selectively transition the RFID tag 124 from the open to secured states using the access password 262, and to recommission the RFID tag 124 using the kill password 260. As described in more detail below, these functions may also be used to assist in authenticating the manifold 116.

In block 314, user data for storage in the user memory bank 206 may be generated. As previously described, the user data may include static data 230 and/or dynamic data 232. The static data 230 may include a rover type datum 236 and threshold data 240. The dynamic data 232 may include use history data 248. In block 316, the rover type datum 236 may be applied to a hash function to generate a first hash digest 238, and the use history data 248 may be applied to a hash function to generate a second hash digest 258. In block 316, the user data, including the generated hash digests 238, 258, may be encrypted, such as using private key encryption. Corresponding data for decrypting the user data may be stored in the memory device 121 of the medical waste collection device 101.

Thereafter, in block 320, the encrypted user data may be written to the RFID tag 124, or more particularly to the user memory bank 206. In some examples, the encrypted static data 230 may be stored in memory blocks 224A, 224B, 224C, 224D of the user memory bank 206, and the encrypted dynamic data 232 may be stored in memory blocks 224E, 224F, 224G, 224H of the user memory bank 206.

In block 322, one or more of the memory banks 200 and/or one or more of the memory blocks 224 of the user memory bank 206 may be locked in a read-only state, such as according to the above-described predefined lock pattern for verifying the RFID tag 124 by the medical waste collection device 101. For instance, one or more of the memory blocks 224 may be locked in a read-only state such that one or more of the memory blocks 224 are not locked in a read-only state according to the predefined lock pattern so that, upon insertion of the manifold 116 into the receiver 112, the rover controller 120 may be configured to authenticate the manifold 116 at least in part by confirming that the memory blocks 224 that are locked and those that are not locked in the read-only state match the predefined lock pattern, which may be stored in the memory device 121 of the medical waste collection device 101 and thus be known to the rover controller 120. In some implementations, the one or more locked memory blocks 224 may be limited to memory blocks 224 that store static data 230, such as the memory blocks 224A, 224B, 224C, 224D.

The one or more locked memory blocks 224 may additionally or alternatively be arranged such that multiple memory blocks 224 are locked in the read-only state, with at least one of the memory blocks 224 not locked in the read-only state interspacing the locked memory blocks 224 within the user memory bank 206. For instance, according to one exemplary predefined lock pattern, the memory blocks 224A, 224B, and 224D may be locked in a read-only state, and the memory block 224C may not be locked in such a state.

The read-only locks placed on the memory blocks 224 may be permanent. In other words, one or more memory blocks 224 of the user memory bank 206 may be locked in a permanent read-only state. According to this type of locked state, the one or more memory blocks 224 may remain locked in the read-only state notwithstanding the RFID tag 124 being recommissioned. In other words, responsive to execution of a recommission command by the tag controller 148, the one or more locked memory blocks 224 of the user memory bank 206 may remain locked in the permanent read-only state. The rover controller 120 may be configured to check for such behavior relative to the one or more locked memory blocks 224 to at least in part authenticate the manifold 116 to which the RFID tag 124 is coupled.

Following the one or more memory blocks 224 being locked, one or more of the memory banks 200 may be locked in a read-only state, such as according to the above-described predefined lock pattern. As examples, the predefined lock pattern may designate that each of the TID memory bank 202, EPC memory bank 204, and user memory bank 206 be locked in a read-only state. The rover controller 120 may thus be configured to check that these memory banks are locked in a read-only state when authenticating the manifold 116. Unlike the one or more memory blocks 224 that may be locked in a permanent read-only state, the one or more memory banks 200 may be locked in a non-permanent read-only state, such as the reversible or semi-permanent read-only state. In other words, it may be possible to transition the locked memory banks 200 to an unlocked writeable state. For instance, responsive to receiving a recommission command, the tag controller 148 may be configured to transition each of the locked memory banks 200 from the read-only state to an unlocked writeable state. In addition, those memory banks 200 locked in the reversible read-only state may be writeable in the secured state of the RFID tag 124, as described above.

In some examples, the predefined lock pattern may designate that different memory banks 200 be locked in different types of non-permanent read-only states to provide a further point of authentication of the manifold 116. As previously described, the semi-permanent read-only state may be effective in both the secured and open states of the RFID tag 124, while the reversible read-only state may be effective in the open state but not the secured state. As one example, the predefined lock pattern may designate that the TID memory bank 202 and/or EPC memory bank 204 be locked in the semi-permanent read-only state effective in both the secured state and the open state, and that the user memory bank 206 be locked in the reversible read-only state effective in the open state but not the secured state. Such an arrangement may provide further points of authentication for the rover controller 120, and may also enable the rover controller 120 to write user data to the user memory bank 206, such as the use history data 248 described above, by transitioning the RFID tag 124 to the secured state and without recommissioning the RFID tag 124.

Both of the above-described non-permanent read-only states may be reversible via recommission. In other words, responsive to receiving a recommission command, the tag controller 148 may be configured to transition each of the TID memory bank 202, EPC memory bank 204, and user memory bank 206 to an unlocked writeable state.

In block 324, the RFID tag 124 may be coupled to the manifold 116. More specifically, the RFID tag 124, including the memory device 128, may be coupled to an internal or external surface of the housing 132 of the manifold 116, such as using an adhesive.

It will be appreciated that one or more of the blocks/datums described above in reference to the method 300 may be performed/written at substantially the same time, and/or during a same programming session, and/or at a same geographic location, and/or one or more of the blocks/datums may be performed/written at different times, and/or during different non-contiguous programming sessions, and/or at different geographic locations. As an example, the TID data and/or originality signature may be written to the memory device 128 at one time and/or geographic location, and the user data may be written at a subsequent time and/or geographic location.

Figure 9A:
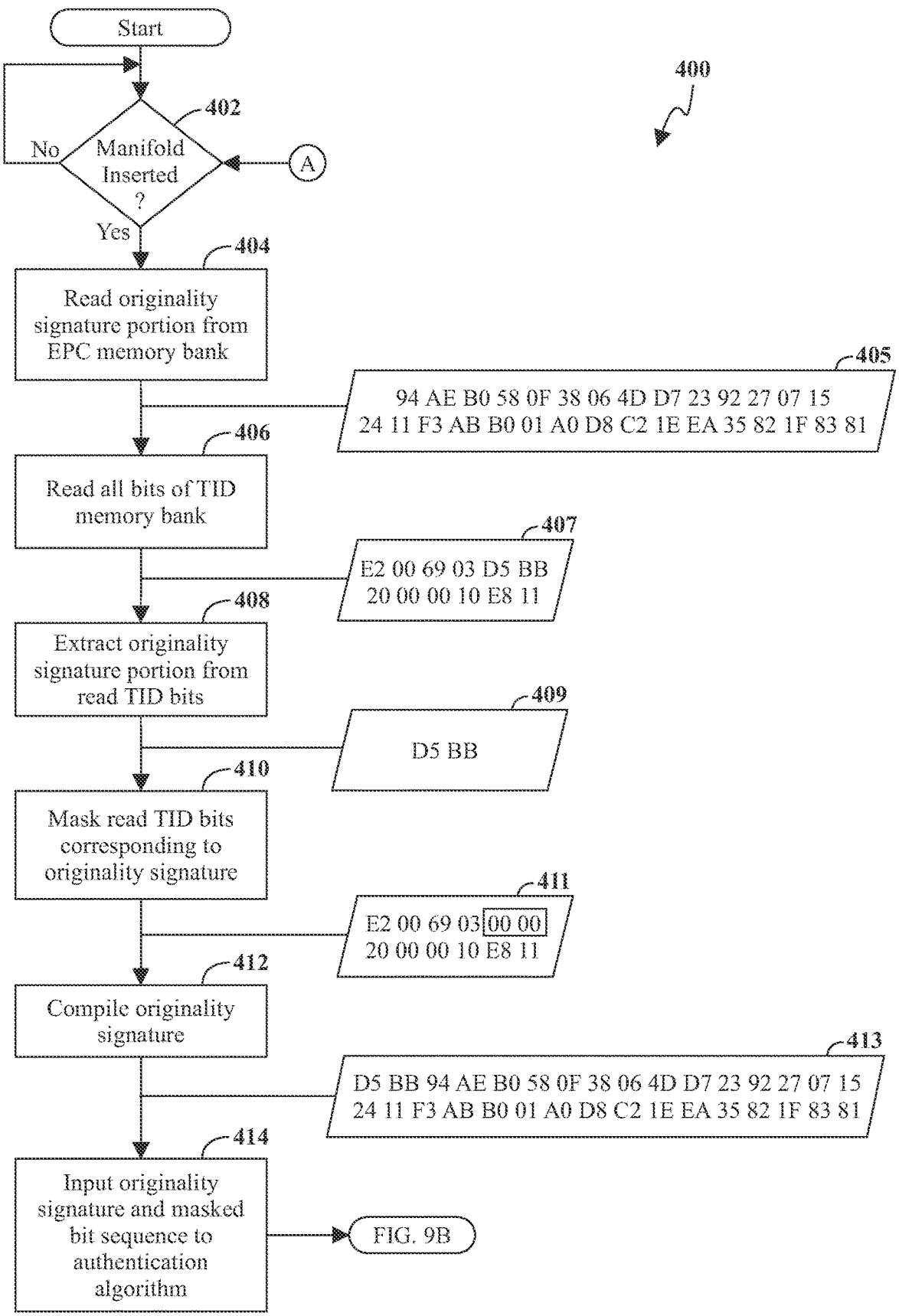
FIGS. 9A and 9B are flow charts illustrating a method for authenticating the manifold by the medical waste collection device.
Figure 9B:
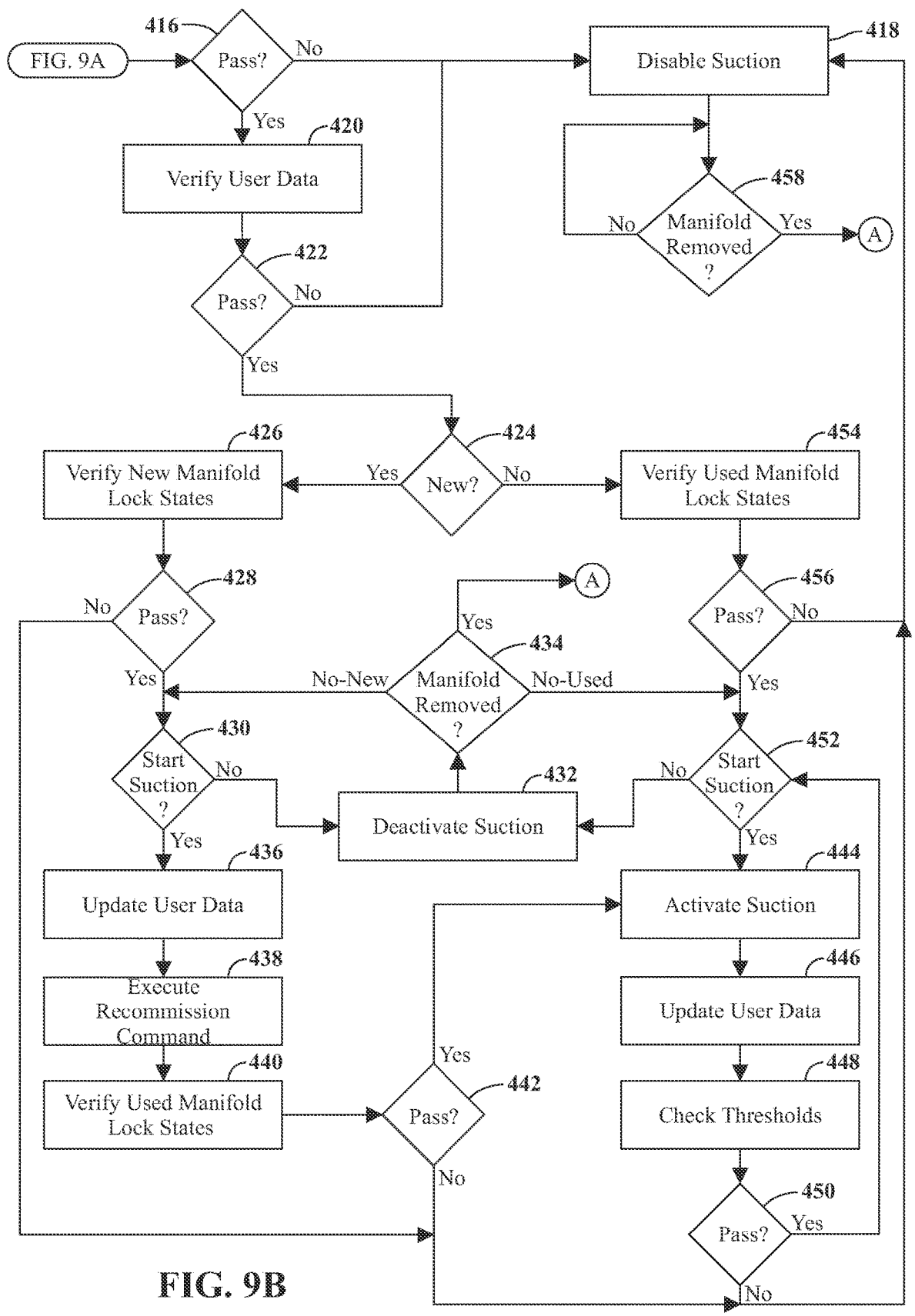

FIG. 9 illustrates a method 400 for authenticating a manifold 116 with a programmed RFID tag 124. The method 400 may generally be implemented by communications between the rover controller 120 and the tag controller 148.

In block 402, a determination may be made of whether a manifold 116 has been coupled to the medical waste collection device 101, or more particularly seated in a receiver 112 of the medical waste collection device 101. The rover controller 120 may be configured to monitor for such insertion by instructing the reader 122 to repetitively emit a basic interrogation signal for the RFID tag 124 of the manifold 116. The manifold 116 and receiver 112 may be configured such that, when the manifold 116 is seated in the receiver 112, the reader 122 is within communication range of the RFID tag 124. Once this event occurs and the reader 122 sends an interrogation signal, the RFID tag 124, or more particularly the tag controller 148, may be configured to send a basic response to the reader 122, which may be forwarded to the rover controller 120 as an indication that a manifold 116 has been inserted in the medical waste collection device 101.

Responsive to determining that a manifold 116 has been coupled to the medical waste collection device 101 ("Yes" branch of block 402), in block 404, the portion of the originality signature 220 stored in the EPC memory bank 204 may be read from the RFID tag 124, such as by the rover controller 120. As previously described, the portion of the originality signature 220 may be 240 bits. Block 405 of FIG. 9 illustrates an example of a portion of an originality signature 220 that may be read in block 404. In some implementations, further in response to determining that the manifold 116 has been coupled to the medical waste collection device 101, one or more datums of the use history data 248 stored in the user memory bank 206 may be updated. For instance, the rover controller 120 may be configured to generate and upload user data to the RFID tag 124 that effectively increments the number of insertions datum 254.

In block 406, the bits of the TID memory bank 202 may be read, such as by the rover controller 120. More specifically, the TID memory bank 202 may include a sequence of at least 96 bits, and the rover controller 120 may be configured to read this entire sequence of bits from the TID memory bank 202, including the tag manufacture data 212, the portion of the originality signature 214, and the tag serial number 216. When reading the sequence of bits, the rover controller 120 may be configured to maintain the order of the bits as in the TID memory bank 202. Block 407 of FIG. 9 illustrates an example of a sequence of bits of the TID memory bank 202 that may be read in block 406.

In block 408, the portion of the originality signature 214 may be extracted from the sequence of bits read from the TID memory bank 202. More specifically, the rover controller 120 may be configured to extract the bits corresponding to the location of the portion of the originality signature 214 from the read sequence of bits. Block 409 of FIG. 9 illustrates bits that may be extracted from the read sequence of bits in block 408. Thereafter, in block 410, the bits of the read sequence of bits corresponding to the portion of the originality signature 214 may be masked. More specifically, the rover controller 120 may be configured to set those to bits to default value such as zero, which is illustrated in block 411 of FIG. 9, to form a modified sequence of bits that includes the masked bits and the remaining bits that were read from the TID memory bank 202.

In block 412, the originality signature may be compiled based on the read portions of the originality signature 214, 220. For instance, the rover controller 120 may be configured to append the portion of the originality signature 220 stored in and extracted from the EPC memory bank 204 to the least significant bit of the portion of the originality signature 214 stored in and extracted from the TID memory bank 202 to form the originality signature. Block 413 of FIG. 9 illustrates an originality signature that may be compiled in this manner in block 412. In alternative implementations, the originality signature may be formed by appending the portion of the originality signatured 214 stored in and extracted from the TID memory bank 202 to the least significant bit of the portion of the originality signature 220 stored in and extracted from the EPC memory bank 204.

Following compilation of the originality signature, the rover controller 120 may be configured to enable operation of the medical waste collection device 101 to provide suction at the surgical site based on the originality signature and/or the modified sequence of TID bits. More specifically, in block 414, the originality signature and/or modified sequence of TID bits, the latter of which may correspond to the bits of the TID memory bank 202 of the RFID tag 124 without the originality signature, may be input into a verification function corresponding to the authentication algorithm used to generate the originality signature, potentially along with a public key determined by the rover controller 120. The verification function may then be configured to determine whether the compiled originality signature, and correspondingly the manifold 116, is authentic based on such input(s). In one example, the rover controller 120 may be configured to implement an Elliptic Curve Digital Signature Algorithm (ECDSA) to verify the originality signature. It is contemplated that other authentication algorithms may be used.

In block 416, a determination may be made of whether the originality signature passes authentication. More specifically, the rover controller 120 may be configured to determine whether the verification function indicated that the originality signature is authentic, and thus passes this layer of authentication. If not ("No" branch of block 416), then suction from the medical waste collection device 101 may be disabled in block 418. In particular, the rover controller 120 may prevent activation of the vacuum pump 110 to provide suction through the manifold 116. Additionally or alternatively, the rover controller 120 may be configured to present a notification that the inserted manifold 116 cannot be used with the medical waste collection device 101, such as via the user interface 126.

Conversely, responsive to determining that the originality signature is authentic ("Yes" branch of block 416), one or more additional layers of authentication may be performed to ensure that the manifold 116 is authentic. For instance, in block 420, the user data stored in the user memory bank 206 may be verified for authenticity. As previously described, the user memory bank 206 may store a rover type datum 236 and a first hash digest 238 generated from the rover type datum 236, and may store use history data 248 including one or more use history datums and a second hash digest 258 generated from the use history data 248. During performance of block 420, the rover controller 120 may be configured to read such user data from the RFID tag 124, and to verify the read data by hashing each of the rover type datum 236 and the one or more datums of the use history data 248 according to the hash function(s) used to generate the first hash digest 238 and second hash digest 258 respectively, and comparing the results of such hashing with the first hash digest 238 and the second hash digest 258 respectively. The rover controller 120 may be configured to determine that the user data is valid if the comparison indicates a match.

Additionally or alternatively, block 420 may include determining whether the manifold 116 has reached or exceeded its expected functional lifespan based on the user data stored in the user memory bank 206. More specifically, the rover controller 120 may be configured to read the use history data 248 and the threshold data 240 from the user memory bank 206, and may be configured to compare the one or more datums of such data to determine whether the manifold 116 to which the RFID tag 124 is affixed has reached or exceeded its expected lifespan. For instance, the rover controller 120 be configured to compare the maximum insertions datum 242 with the number of insertions datum 254, and/or compare the maximum volume datum 244 with the volume collection datum 256, and/or compare the maximum duration(s) datum 246 with a current date, the first insertion datum 250 and/or the first suction datum 252. If the number of insertions datum 254 indicates a value that is greater than or equal to a threshold value defined by the maximum insertions datum 242, or if the volume collected datum 256 indicates a value that is greater than or equal to a threshold value defined by the maximum volume datum 244, or if the duration between the current date and/or time and that indicated by the first insertion datum 250 is greater than or equal to a corresponding threshold duration defined by the maximum duration(s) datum 246, or if the duration between the current date and/or time and that indicated by the first suction datum 252 is greater than or equal a corresponding threshold duration defined by the maximum duration(s) datum 246, and/or if the current date and/or time is greater than or equal to an expiration date defined by the maximum duration(s) datum 246, then the rover controller 120 may be configured to determine that the manifold 116 has reached or exceeded its expected lifespan. Consequently, the rover controller 120 may be configured to determine that the user data fails to pass verification.

Additionally or alternatively, block 420 may include determining whether the RFID tag 124 has previously executed a recommission command, and comparing this determination with the use history data 248 to verify that the use history data 248 is consistent with the determination. As described in more detail below, contemporaneously with suction being applied through the manifold 116 for the first time, the rover controller 120 may be configured to update the one or more datums of the use history data 248 to reflect usage of the manifold 116, and to instruct the RFID tag 124 to execute a recommission command. As part of executing the recommission command, the tag controller 148 may be configured to store data in the memory device 128, such as in the EPC memory bank 204, indicative that the that RFID tag 128 has been recommissioned. Under this configuration, if the RFID tag 124 includes data indicating a previous recommission, then at least one of the datums of the use history data 248 should be altered from its default value. Alternatively, if the RFID tag 124 does not include data indicating a previous recommission, then the datums of the use history data 248 should each be set to its default value.

The rover controller 120 may thus be configured to verify the user data of the user memory bank 206 at least in part by determining whether the values of the datums of the use history data 248 are consistent with the determination of the RFID tag 124 has been recommissioned. If not, then the rover controller 120 may be configured to determine that the user data fails to pass verification.

Additionally or alternatively, block 420 may include comparing the rover type datum 236 stored in the user memory bank 206 with the type and/or capabilities of the medical waste collection device 101. If the rover controller 120 determines that the compatibility of the manifold 116 as indicated by the rover type datum 236 is inconsistent with the type and/or capabilities of the medical waste collection device 101, which may be indicated by data stored in the memory device 121 of the medical waste collection device 101, then the rover controller 120 may be configured to determine that the user data fails to pass verification.

As previously described, the user data stored in the user memory bank 206 may be encrypted. In this case, the rover controller 120 may also be configured to decrypt the user data prior to performing the above analyses. In particular, the memory device 121 of the medical waste collection device 101 may store data, such as a secret key, used by the rover controller 120 to decrypt the read user data. The rover controller 120 may similarly be configured to encrypt updated user data prior to communicating the same to the RFID tag 124.

In block 422, a determination may be made of whether the user data passed verification based on one or more of the above analyses. If not ("No" branch of block 426), then suction from the medical waste collection device 101 may be disabled in block 418. In particular, the rover controller 120 may prevent activation of the vacuum pump 110 to provide suction through the manifold 116. Additionally or alternatively, the rover controller 120 may be configured to present a notification that the inserted manifold cannot be used with the medical waste collection device 101 and/or has reached or exceeded its expected lifespan if appropriate, such as via the user interface 126.

Alternatively, responsive to determining that the user data passed verification ("Yes" branch of block 422), a further layer of authentication may be implemented, such based on the predefined lock pattern defined for the RFID tag 124. As previously described, the predefined lock pattern may designate which memory banks 200 and/or memory blocks 224 should be and/or should not be locked in a read-only state, and may also indicate a type of read-only state for each of the locked memory banks 200 and/or memory blocks 224 (e.g., permanent, semi-permanent, reversible). The rover controller 120 may be configured to verify the lock states of the memory banks 200 and/or memory blocks 224 against the predefined lock pattern, such as by verifying that each object of the predefined lock pattern (e.g., memory bank 200, memory block 224) exhibits one or more behavioral characteristics consistent with the lock state designated for the object by the predefined lock pattern.

To this end, in block 424, a determination may be made of whether the RFID tag 124 is new or used, which may affect the lock states of the RFID tag 124. As described above, contemporaneously with suction being applied to the manifold 116 for the first time, the rover controller 120 may be configured to submit a recommission command to the RFID tag 124 of the manifold 116. Execution of the recommission command by the RFID tag 124 may function to unlock objects locked in a non-permanent read-only state, but not those locked in a permanent read-only state. In this way, the predefined pattern may be considered as defining one or more behavioral characteristics for the object both before and after the RFID tag 124 is recommissioned, which may be the same or vary depending on the designated lock state.

Upon being recommissioned, the RFID tag 124 may also be configured to store data in the memory device 128, such as the EPC memory bank 204, indicative that the RFID tag 124 has been recommissioned. The rover controller 120 may thus be configured to determine whether the manifold 116 is new or used by determining whether the RFID tag 124 includes data indicative of a previous recommission. In other words, responsive to the RFID tag 124 not including data indicative of a previous recommission, the rover controller 120 may be configured to determine that the manifold 116 is in a new condition, and responsive to the RFID tag 124 including data indicative of a previous recommission, the rover controller 120 may be configured to determine that the manifold 116 is in a used condition. Because the behavioral characteristics of an object designated as being locked in a non-permanent read-only state may differ depending on whether the RFID tag 124 has been recommissioned, the rover controller 120 may be configured to use this information when verifying the RFID tag 124 against the predefined lock pattern for the RFID tag 124.

Responsive to determining that the manifold 116 is in the new condition ("New" branch" of block 424), in block 426, the lock states of one or more of the memory banks 200 and/or one or more of the memory blocks 224 of the user memory bank 206 may be verified against the predefined lock pattern taking into consideration that the manifold 116 is in a new condition. In other words, the rover controller 120 may be configured to check whether each object includes one or more behavioral characteristics consistent with the lock state designated for the object by the predefined lock pattern when the RFID tag 124 has not yet been recommissioned. As an example, to determine whether or not a given object is locked in a read-only state, the rover controller 120 may be configured to determine whether the object exhibits a behavioral characteristic consistent with being locked in a read-only state, such as by trying to write data to the object. Responsive to determining a write error, such as by receiving a write error communication from the tag controller 148 and/or performing a subsequent read operation on the object and determining that the data was not written, the rover controller 120 may be configured to determine that the object exhibits a behavioral characteristic consistent with being locked in a read-only state, and is thus locked in a read-only state. Alternatively, responsive to determining that the write operation was successful, such as by reading the written data back from the object following execution of the write operation, the rover controller 120 may be configured to determine that the object does not exhibit a behavioral characteristic consistent with being locked in a read-only state, and is thus not locked in a read-only state. The rover controller 120 may further be configured to roll back the successful write operation in this case.

As described above, if a given memory bank 200 is locked in the semi-permanent read-only state, then the memory bank 200 may be read-only in both the open and secured states of the RFID tag 124, and may be transitioned to an unlocked writeable state following recommission of the RFID tag 124. Thus, to at least partially verify that a given memory bank 200 is locked in the semi-permanent read-only state when the manifold 116 is in the new condition, the rover controller 120 may be configured to initially determine whether the given memory block 224 is in a read-only state as described above when the RFID tag 124 is in the open state. Responsive to determining that the memory bank 200 is in a read-only state when the RFID tag 124 is in the open state, the rover controller 120 may be configured to transition the RFID tag 124 to the secured state using the stored access password 262, and to again attempt to write data to the memory bank 200 as described above. Responsive to determining that the memory bank 200 is still in a read-only state, the rover controller 120 may be configured to determine that the memory bank 200 exhibits a behavioral characteristic consistent with being locked in the semi-permanent read-only state. Based on this determination, the rover controller 120 may be configured to determine by assumption that the memory bank 200 is locked in the semi-permanent read-only state. Alternatively, the rover controller 120 may be configured to determine that the memory bank 200 may be locked in the semi-permanent read-only state, subject to further verification following recommission of the RFID tag 124.

As described above, if a given memory bank 200 is locked in the reversible read-only state, then the memory bank 200 may be read-only in the open state but not the secured state of the RFID tag 124, and may be unlocked following recommission of the RFID tag 124. Thus, to at least partially verify that a given memory bank 200 is locked in the reversible read-only state when the manifold 116 is in the new condition, the rover controller 120 may be configured to initially determine whether the given memory block 224 is in a read-only state as described above when the RFID tag 124 is in the open state. Responsive to determining that the memory bank 200 is in a read-only state when the RFID tag 124 is in the open state, the rover controller 120 may be configured to transition the RFID tag 124 to the secured state using the stored access password 262, and to again attempt to write data to the memory bank 200 as described above. Responsive to determining that the write was successful, the rover controller 120 may be configured to roll back the successful write operation, and may be configured to determine that the memory bank 200 exhibits a behavioral characteristic consistent with being locked in the reversible read-only state. Based on this determination, the rover controller 120 may be configured by assumption to determine that the memory bank 200 is locked in the reversible read-only state. Alternatively, the rover controller 120 may be configured to determine that the memory bank 200 may be locked in the in the reversible read-only state, subject to further verification following recommission of the RFID tag 124.

As described above, if a given memory block 224 is locked in the permanent read-only state, then the memory block 224 may be read-only both before and after recommission of the RFID tag 124, notwithstanding whether the RFID tag 124 is in the open or secured state. Thus, to at least partially verify that a given memory block 224 is locked in a permanent read-only state when the manifold 116 is in the new condition, the rover controller 120 may be configured to determine whether the given memory block 224 is in a read-only state as described above. Responsive to determining that the given memory block 224 is in the read-only state, the rover controller 120 may be configured to determine that the memory block 224 exhibits a behavioral characteristic consistent with being locked in the permanent read-only state. Based on this determining, the rover controller 120 may be configured by assumption to determine that the memory block 224 is locked in the permanent read-only state. Alternatively, the rover controller 120 may be configured to determine that the memory block 224 may be locked in the permanent read-only state, subject to further verification following recommission of the RFID tag 124.

In some instances, the rover controller 120 may be configured to rely on status inquiry commands for verifying the lock state of some types of objects, such as the memory blocks 224, and to rely on data write operations as described above to verify the lock states of other types of objects, such as the memory banks 200. In other words, to determine whether a given memory block 224 is locked in a permanent read-only state, the rover controller 12 may be configured to communicate a status inquiry command for the memory block 224 to the tag controller 148, which may communicate a reply message indicative of the lock state of the memory block 224. The rover controller 12 may then be configured to determine whether the memory blocks 224 satisfies the predefined lock pattern based on the reply messages.

In some instances, the predefined lock pattern may designate both that one or more of the memory blocks 224 are locked in a permanent read-only state and that the user memory bank 206 is locked in the reversible read-only state. To verify the predefined lock pattern in this case and when the manifold 116 is determined in the new condition, when the RFID tag 124 is in the open state, the rover controller 120 may be configured to first try writing data to one or more of the memory blocks 224 of the user memory bank 206 that are not designated to be in a read-only state by the predefined lock pattern as described above. Responsive to determining that the write operation fails, the rover controller 120 may be configured to transition the RFID tag 124 to the secured state using the access password 262. Thereafter, when the RFID tag 124 is in the secured state, the rover controller 120 may be configured to verify that one or more of the memory blocks 224 are in a read-only state and one or more of the memory blocks 224 are in an unlocked writable state according to the predefined lock pattern, such as using write data operations or lock status inquires as described above.

In block 428, based on the above-described analysis, a determination may be made of whether the memory banks 200 and/or memory blocks 224 of the RFID tag 124 satisfy the predefined lock pattern and thus pass a lock status verification when the manifold 116 is determined to be in the new condition. If not ("No" branch of block 428), then suction from the medical waste collection device 101 may be disabled in block 418. In particular, the rover controller 120 may prevent activation of the vacuum pump 110 to provide suction through the manifold 116. The rover controller 120 may also be configured to present a notification that the inserted manifold 116 cannot be used with the medical waste collection device 101, such as via the user interface 126.

Alternatively, responsive to determining that the memory banks 200 and/or memory blocks 224 satisfy the predefined lock pattern when the manifold 116 is determined to be in the new condition ("Yes" branch of block 428), the rover controller 120 may be configured to provide a user indication that suction may be activated, such as via the user interface 126. Thereafter, in block 430, a determination may be made of whether suction has been activated by the user, such as by the user submitting a command instructing the rover controller 120 to start suction. More specifically, the rover controller 120 may be configured to monitor for such a command. Responsive to determining that no such command has been received ("No" branch of block 430), in block 432, suction may remain in a deactivated state.

In block 434, a determination may be made of whether the manifold 116 has been removed from the medical waste collection device 101. For example, the rover controller 120 may be configured to monitor for such removal by instructing the reader 122 to periodically emit a basic interrogation signal for the RFID tag 124 of the manifold 116. While the manifold 116 is seated in the receiver 112, the RFID tag 124, or more particularly the tag controller 148, may be configured to send a basic response to the reader 122, which may be forwarded to the rover controller 120 as an indication that a manifold 116 is still inserted in the medical waste collection device 101. In this case ("No-New" branch of block 434), monitoring for receipt of the run command may continue in block 430, which may be performed in parallel with or in between the determinations of block 434. Alternatively, if no response is received from the RFID tag 124, a determination may be made, such as by the rover controller 120, that the manifold 116 has been removed ("Yes" branch of block 434). Responsively, the method 400 may transition back to block 402 to determine whether a manifold 116 is again inserted in the medical waste collection device 101, and so on.

Referring again to block 430, responsive to determining receipt of a start command from the user ("Yes" branch of block 430), in block 436, the user data of the user memory bank 206 may be updated. In particular, the rover controller 120 may be configured to update the datums of the use history data 248 as appropriate. For instance, the rover controller 120 may be configured to generate updated user data indicating a current date and/or time for the first suction datum 252. Based on the updated user data, the rover controller 120 may also be configured to generate a new second hash digest 258. The rover controller 120 may then be configured to encrypt the updated user data and communicate the same to the RFID tag 124 for storage in the user memory bank 206.

As previously described, in some instances, the user memory bank 206 may be locked in the reversible read-only state. In this case, the rover controller 120 may be configured to transition the RFID tag 124 to the secured state prior to writing the updated user data to the user memory bank 206.

In block 438, following update of the user data, a recommission command may be executed communicated to and executed by the RFID tag 124. In particular, the rover controller 120 may be configured to communicate the recommission command to the tag controller 148 of the RFID tag 124. Responsive to receiving the recommission command, the tag controller 148 may be configured to store data indicative that the RFID tag 124 is recommissioned, such as in the EPC memory bank 204. Execution of the recommission command may also function to transition objects locked in a non-permanent state to an unlocked writeable state. To this end, the tag controller 148 may be configured to transition each of the memory banks 200 locked in the reversible or semi-permanent read-only state into and an unlocked writeable state. Each of the memory blocks 224 locked in the permanent read-only state may remain locked in the permanent read-only state responsive to execution of the recommission command by the tag controller 148.

In block 440, responsive to the RFID tag 124 executing the recommission command, the memory banks 200 and/or memory blocks 224 may be verified against the predefined lock pattern taking now into consideration that the manifold 116 is in the used condition. In particular, following receipt of the start command in block 430 and the RFID tag 124 being recommissioned in block 438, the manifold 116 may be considered as used. Accordingly, the rover controller 120 may be configured to verify the lock states of the memory banks 200 and/or memory blocks 224 when the manifold 116 is considered in the used condition, such as by checking that each of the objects exhibit a behavioral characteristic consistent with the lock state designated for the object in the predefined lock pattern when the RFID tag 124 has been recommissioned. To this end, the rover controller 120 may be configured to verify that each object designated by the predefined lock pattern as being locked in a non-permanent read-only state is now in an unlocked writeable state, and that each object designated in the predefined lock pattern as being locked a permanent read-only state continues to be locked in the read-only state, such as using the writing data method described above.

In block 442, based on the above analysis, a determination may be made of whether the RFID tag 124 satisfies the predefined lock pattern when the RFID tag 124 is considered in the used condition, and thus passes lock state verification for the used condition. If not ("No" branch of block 442), then suction from the medical waste collection device 101 may be disabled in block 418. In particular, the rover controller 120 may prevent activation of the vacuum pump 110 to provide suction through the manifold 116. The rover controller 120 may also be configured to present a notification that the inserted manifold 116 cannot be used with the medical waste collection device 101, such as via the user interface 126.

Alternatively, responsive to determining that the RFID tag 124 does pass the lock state verification for the used condition ("Yes" branch of block 442), in block 444, the manifold 116 may be considered fully authenticated, and suction may be activated. In particular, the rover controller 120 may be configured to instruct the vacuum pump 110 to turn on and draw suction through the manifold 116 into the waste container(s) 106, 108. A user may then apply the suction tube(s) 118 coupled to the manifold 116 to surgical site during a procedure to collect medical waste with the confidence that the manifold 116 is an authentic, quality manifold.

In some implementations, as the medical waste collection device 101 is operated to provide suction through the manifold 116, the rover controller 120 may be configured update the user data stored in the user memory bank 206 in accordance with the extent to which the manifold 116 is used. To this end, in block 446, following suction being activated, the user data stored in the user memory bank 206 may be updated. More specifically, the rover controller 120 may be configured to periodically update the use history data 248 stored in the user memory bank 206, such as the volume collected datum 256, with operation of the medical waste collection device 101.

Thereafter, in block 448, the threshold data 240 may be checked against the updated use history data 248. For example, the rover controller 120 may be configured to compare the value of the volume collected datum 256 with the threshold value of the maximum volume datum 244, and/or may be configured to compare a duration between the value of the first suction datum 252 and a current date and/or time with a corresponding threshold duration indicated by the maximum duration(s) datum 246, and/or may be configured to compare a duration between the value of the first insertion datum 250 and a current date and/or time with a corresponding threshold duration indicated by the maximum duration(s) datum 246, and/or may be configured to compare a current date and/or time with an expiration date indicated by the maximum duration(s) datum 246. Responsive to any of these comparisons indicating that the value of a use history datum is greater than or equal to the value of a corresponding threshold datum, the rover controller 120 may be configured to determine that the manifold 116 has reached or is past its expected lifespan, and thus did not pass the threshold check.

In block 450, based on the above, a determination may be made of whether the manifold 116 passed the threshold check of block 448. If not ("No" branch of block 450), then suction from the medical waste collection device 101 may be disabled in block 418. In particular, the rover controller 120 may prevent activation of the vacuum pump 110 to provide suction through the manifold 116. The rover controller 120 may also be configured to present a notification that the inserted manifold 116 cannot be used with the medical waste collection device 101, such as via the user interface 126. Alternatively, responsive to determining that the manifold 116 has passed the threshold check ("Yes" branch of block 450), in block 452, a determination may be made of whether to continue running suction. For instance, the rover controller 120 may be configured to monitor for a further input from the user indicating an instruction to deactivate suction. Responsive to determining not to continue suction, such as upon receipt of such user input ("No" branch of block 452), in block 432, suction may be deactivated. Whether the manifold 116 is removed may then be monitored in block 434 as described above, and whether to resume suction may be determined in block 452 as described above through the "No-Used" branch of block 434.

Referring back to block 424 of the method 400, responsive to determining that the manifold 116 is in the used condition, such as based on data stored in the RFID tag 124 indicative of a previous recommission, in block 454, the lock state of the RFID tag 124 may be verified in block 454 for the used condition, and a determination of whether the locked state passes such verification for the used condition may be determined in block 456. Blocks 454 and blocks 456 may operate similarly to blocks 440 and 442 described above. Thus, responsive to determining the RFID tag 124 satisfies the predefined lock pattern when the RFID tag 124 is considered in the used condition, and thus passes lock state verification for the used condition ("Yes" branch of block 456), a determination may be made of whether to activate suction in block 452, such as by monitoring for user input indicating as such. The method 400 may then proceed as described above.

Alternatively, responsive to determining that the RFID tag 124 does not pass the lock state verification for the used condition ("No" branch of block 456), then suction from the medical waste collection device 101 may be disabled in block 418. In particular, the rover controller 120 may prevent activation of the vacuum pump 110 to provide suction through the manifold 116. The rover controller 120 may also be configured to present a notification that the inserted manifold 116 cannot be used with the medical waste collection device 101, such as via the user interface 126.

Responsive to suction being disabled in block 418, in block 458, a determination may be made of whether the manifold 116 has been removed from the medical waste collection device 101. Block 458 may operate similar to block 434 described above. Responsive to determining that the manifold 116 has been removed ("Yes" branch of block 458), the method 400 may transition back to block 402 to determine whether a manifold 116 is again inserted in the medical waste collection device 101, and so on.

It is contemplated that in some implementations, not all the layers of authentication illustrated in FIG. 9 may be performed by the rover controller 120 to authenticate an inserted manifold 116. For instance, the lock status verifications and/or the user data verifications may be omitted, such that the rover controller 120 may be configured to authenticate the manifold 116 based on the remaining verifications only (e.g., based on the originality signature, based on the on the originality signature and the lock status verifications, based on the originality signature and user data verifications). Alternatively, the originality signature verification and/or user data verifications may be omitted. It is also contemplated that verifications and/or other processes of the method 400 may be performed in a different order. As examples, the rover controller 120 may be configured to verify the user data and/or lock states prior to verifying the originality signature, and may be configured to communicate a recommission command to the RFID tag 124 to perform the lock state verification for the used condition prior to receiving user input to start suction. It is additionally contemplated that the rover controller 120 may be configured to verify the lock state of the RFID tag 124 under the new condition, but not under the used condition.

It is also contemplated that at least a portion of FIG. 9, such as one or more of the authentication layers, may be performed by a processing system remote from the medical waste collection device 101, such as a cloud server or hub. More particularly, the rover controller 120 may be configured to communicate data read from the RFID tag 124 of an inserted manifold 116 to such remote processing system, such as over one or more private and/or public networks including the internet, and over one or more wired and/or wireless connections, for implementation of one or more of the authentication layers as described above. To this end, the medical waste collection device 101 may further include a communications transceiver for establishing connections with such remote processing system. In some examples, the layers of authentication illustrated in FIG. 9 may be split between the rover controller 120 and the remote processing system. For instance, the remote processing system may be configured to perform authentication of the originality signature, and the rover controller 120 may be configured to perform authentication of the predefined lock pattern. In some examples, different manifolds 116 may have different predefined lock patterns, which may be tracked by the remote processing system. In this case, responsive to a given manifold 116 being received by the medical waste collection device 101, and/or to the remote processing system authenticating the originality signature for the manifold 116 as described above, the remote processing system may be configured to forward the predefined lock pattern associated with the given manifold 116 to the medical waste collection device 101 for further authentication by the rover controller 120.

In some implementations, the remote processing system may be a hub, such as a locally located hub (e.g., located in same facility as connected surgical devices), in communication with one or several surgical devices, such as several medical waste collection devices 101, and such as via a local network (e.g., WiFi, Bluetooth). The hub may thus be configured to perform the authentication processes for each surgical device paired to the hub, such as based on data received from the surgical device (e.g., data read from a received manifold 116). In some instances, the hub may also be configured to pull data from a remote server to facilitate the authentication processes, such as updated keys, updated predefined lock patterns, and updated authentication algorithms corresponding to a given received manifold 116. As one example, the hub may be similar to that described in U.S. Patent Publication No. 2022/0317827, published Oct. 6, 2022, which is hereby incorporated by reference herein in its entirety. In some implementations, the hub may also be configured to forward such updates to the medical waste collection device(s) 101 to enable local authentication by the medical waste collection devices 101 based thereon.

In some instances, the above-described hub may be incorporated into a docking station for the medical waste collection device 101. The docking station may be configured to receive the medical waste collection device 101 for emptying and cleaning the canisters 106, 108. As one example, the docking station may be similar to that described in International Publication No. WO 2007/070570, published Jun. 21, 2007, which is hereby incorporated by reference herein in its entirety.

In some instances, such as when the rover controller 120 is configured to perform the aforementioned authentication locally, communication between the docking station and medical waste collection device 101 may be limited to proximity- or line of site-based connections (e.g., infrared, NFC, or RFID), which may be established when the medical waste collection device 101 is docked with the docking station. In this case, the docking station may be configured to periodically receive any updated keys, predefined lock patterns, and authentications algorithms from a remote server, and communicate such updated information to the medical waste collection 101 for the authentication of manifolds 116 when the medical waste collection 101 is next docked to the docking station.

It is contemplated that the above-described RFID tag 124 may be replaced with a suitable alternative device, such as an alternative type of tag, memory device, or a controller including a memory device, that is communicatively coupled with the rover controller 120 upon the manifold 116 being received in the medical waste collection device 101 for the exchange of data and/or authentication as described above. For instance, the manifold 116 may include a controller and/or memory device configured to establish a wired data connection, or alternatively an IR data connection, with the rover controller 120 upon the manifold 116 being received. As a further example, manifold 116 may include a barcode encoded with the above-described data, with the rover controller 120 being coupled to a barcode reader such that the rover controller 120 is able to read the barcode upon the manifold 116 being received by the medical waste collection device 101.

Although described above in the context of a manifold 116 for a waste collection device 101, a controller and/or memory device and/or tag described above may be used with a variety of medical/surgical devices and/or systems. For example, the following devices are contemplated: 1) Lighting devices comprising a controller and/or memory device and/or tag, such as the lighting device described in U.S. Pat. No. 10,226,555, which is hereby incorporated by reference herein in its entirety; 2) Suction devices comprising a controller and/or memory device and/or tag, such as the suction devices described in U.S. Pat. Nos. 11,376,093 9,510,737 and/or 10,499,974, which are hereby incorporated by reference herein in their entirety; 3) Surgical garments comprising a controller and/or memory device and/or tag, such as the surgical garments described in U.S. Pat. Nos. 11,090,516 and/or 11,291,265, which are hereby incorporated by reference herein in their entirety; 4) Electrosurgical devices, such as electrosurgical pencils or forceps, comprising a controller and/or memory device and/or tag, such as the electrosurgical devices described in U.S. Pat. Nos. 10,070,912 and/or 8,361,070, which are hereby incorporated by reference herein in their entirety; 5) Retractors comprising a controller and/or memory device and/or tag, such as the retractors described in U.S. Pat. Nos. 11,351,004 and/or 11,382,711, which are hereby incorporated by reference herein in their entirety; 6) Smoke filters comprising a controller and/or memory device and/or tag, such as the smoke filters described in U.S. Pat. Nos. 11,160,909 and/or 7,761,188, which are hereby incorporated by reference herein in their entirety; 7) Irrigation sleeves for ultrasonic devices comprising a controller and/or memory device and/or tag, such as the irrigation sleeve described in U.S. Pat. No. 11,317,936, which is hereby incorporated by reference herein in its entirety; and 8) Irrigation cassettes for surgical consoles comprising a controller and/or memory device and/or tag, such as the cassettes described in U.S. Pat. Nos. 7,632,079 and/or 8,035,487, which are hereby incorporated by reference herein in their entirety; 9) Intrauterine devices comprising a controller and/or memory device and/or tag, such as the intrauterine devices described in U.S. Provisional App. No. 63/323,677 and/or PCT/US22/41636, which are hereby incorporated by reference herein in their entirety; 10) Surgical sponges or other surgical objects comprising a controller and/or memory device and/or tag, such as the surgical sponges described in U.S. Pat. Nos. 7,703,674 and/or 11,116,598, which are hereby incorporated by reference herein in their entirety; and 11) Sterilization trays comprising a controller and/or memory device and/or tag, such as the sterilization tray described in U.S. Pat. No. 5,540,901, which is hereby incorporated by reference herein in its entirety.

In addition, it is contemplated that the described methods of programming an RFID tag 124 for a manifold 116 may be applied to controllers and/or memory devices and/or tags for these alternative devices. Furthermore, it is contemplated that medical waste collection device 101 may be replaced by an appropriate alternative device, such as a surgical console, a surgical handpiece, a surgical helmet, a smoke filtration console, a sponge scanner, etc., and hence, these devices could perform the methods described herein with respect to the medical waste collection device 101 and/or rover controller 120. It is also contemplated that a controller and/or memory device and/or tag described above may be incorporated into a cord or connector of a surgical device or instrument, such as an electrical cord or connector of a handheld surgical device or instrument (e.g., the cord connector of an electrosurgical or ultrasonic surgical instrument). In this way, a data connection may be formed between the controller and/or memory device and/or tag upon the connector of the surgical device or instrument being coupled to a receiving device, such as a surgical console, which may in turn be configured to perform the authentication routine(s) described above.

In general, the routines executed to implement aspects of the invention, whether implemented as part of an operating system or a specific application, component, program, object, module or sequence of instructions, or even a subset thereof, may be referred to herein as "computer program code," or simply "program code." Program code may comprise computer readable instructions that are resident at various times in various memory and storage devices in a computer and that, when read and executed by one or more processors in a computer, cause that computer to perform the operations necessary to execute operations and/or elements embodying the various aspects of the invention. Computer readable program instructions for carrying out operations of the various aspects of the invention may be, for example, assembly language or either source code or object code written in any combination of one or more programming languages.

The program code embodied in any of the applications/modules described herein may be capable of being individually or collectively distributed as a program product in a variety of different forms. In particular, the program code may be distributed using a computer readable storage medium having computer readable program instructions thereon for causing a processor to carry out aspects of the embodiments of the invention.

Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include random access memory (RAM), read-only memory (ROM), erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. A computer readable storage medium should not be construed as transitory signals per se (e.g., radio waves or other propagating electromagnetic waves, electromagnetic waves propagating through a transmission media such as a waveguide, or electrical signals transmitted through a wire). Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions/acts specified in the flowcharts, sequence diagrams, and/or block diagrams. The computer program instructions may be provided to one or more processors such that the instructions, which execute via the one or more processors, cause a series of computations to be performed to implement the functions and/or acts specified in the flowcharts, sequence diagrams, and/or block diagrams described herein.

In certain alternatives, the functions and/or acts specified in the flowcharts, sequence diagrams, and/or block diagrams may be re-ordered, processed serially, and/or processed concurrently without departing from the scope of the invention. Moreover, any of the flowcharts, sequence diagrams, and/or block diagrams may include more or fewer blocks than those illustrated herein.

The terminology used herein is for the purpose of describing particular examples only and is not intended to be limiting. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes," "having," "has," "with," "comprised of," or variants thereof are used in either the detailed description or the claims, such terms are intended to be inclusive in a manner similar to the term "comprising."

While all of the invention has been illustrated by a description of various examples and while these examples have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

Some examples are described with reference to the following numbered clauses, with specific features laid out in dependent clauses:

1. An RFID tag for a manifold configured to be coupled to a vacuum inlet integral with a medical waste collection device to provide suction at a surgical site through the manifold, the RFID tag comprising:
   a memory device storing an originality signature for the manifold, the originality signature for being read by the medical waste collection device when the manifold is proximate the medical waste collection device to control actuation of the medical waste collection device, the memory device comprising:
      a first memory bank storing an identifier for the RFID tag and a first portion of the originality signature, the first portion having a character length of at least 16 bits;
      a second memory bank for storing electronic identification data for the manifold, the second memory bank storing a second portion of the originality signature, the second portion having a character length of at least 240 bits; and
      a third memory bank storing a rover type datum corresponding to the medical waste collection device, a first hash digest generated based on the rover type datum, use history data for the manifold, and a second hash digest generated based on the use history data for the manifold.

2. The RFID tag of clause 1, wherein the first portion of the originality signature is 16 bits in length, and the second portion of the originality signature is 240 bits in length.

3. The RFID tag of clause 1 or 2, wherein the first memory bank has a capacity of 96 bits, and the second memory bank has a capacity of at least 304 bits.

4. The RFID tag of any one of clauses 1 to 3, wherein the memory device comprises four memory banks.

5. The RFID tag of any one of clauses 1 to 4, wherein each of the first portion and the second portion of the originality signature includes a sequence of non-zero characters,
   wherein, optionally, each of the first portion and second portion further includes one or more zeros.

6. The RFID tag of any one of clauses 1 to 5, wherein the first memory bank further stores a mask designer identifier for the RFID tag and a model number of the RFID tag.

7. The RFID tag of any one of clauses 1 to 6, wherein the second memory bank is locked in a read-only state.

8. The RFID tag of any one of clauses 1 to 7, wherein the third memory bank comprises a plurality of memory blocks with one or more of the memory blocks ("first memory blocks") being locked in a permanent read-only state and one or more of the memory blocks ("second memory blocks") not being locked in the permanent read-only state according to a predefined lock pattern for verifying the RFID tag by the medical waste collection device.

9. The RFID tag of clause 8, wherein the one or more first memory blocks comprises a plurality of first memory blocks, the plurality of first memory blocks being interspaced by at least one of the one or more second memory blocks within the third memory bank.

10. The RFID tag of clause 8 or 9, wherein each of the memory blocks is eight bytes.

11. The RFID tag of any one of clauses 8 to 10, wherein the one or more first memory blocks comprises two first memory blocks and the one or more second memory blocks comprises four second memory blocks.

12. The RFID tag of clause 11, wherein the one or more first memory blocks comprises three first memory blocks and the one or more second memory blocks comprises five second memory blocks,
    wherein, optionally, the one or more first memory blocks consists of three first memory blocks and the one or more second memory blocks consists of five second memory blocks.

13. The RFID tag of any one of clauses 8 to 12, further comprising a controller coupled to the memory device and configured to:
    receive a lock status inquiry for one of the one or more first memory blocks and for one of the one or more second memory blocks;
    responsive to receiving the lock status inquiry for the one of the one or more first memory blocks, indicate that the one of the one or more first memory blocks is locked in the permanent read-only state; and
    responsive to receiving the lock status inquiry for the one of the one or more second memory blocks, indicate that the one of the one or more second memory blocks is not locked in the permanent read-only state.

14. The RFID tag of any one of clauses 8 to 13, wherein the first memory bank is locked in a non-permanent read-only state and/or the second memory bank is locked in the non-permanent read-only state, and further comprising a controller coupled to the memory device and configured to:
    receive a recommission command for the RFID tag; and
    responsive to receiving the recommission command:
        store data indicative that the RFID tag has been recommissioned in the RFID tag; and
        transition the first memory bank and/or the second memory bank from the non-permanent read-only state to an unlocked writeable state,
    wherein each of the one or more first memory blocks remains locked in the permanent read-only state responsive to execution of the recommission command by the controller.

15. The RFID tag of any one of clauses 8 to 14, wherein the third memory bank is locked in a non-permanent read-only state, and further comprising a controller coupled to the memory device and configured to:
    receive a recommission command for the RFID tag; and
    responsive to receiving the recommission command:
        store data indicative that the RFID tag has been recommissioned in the RFID tag; and
        transition the third memory bank from the non-permanent read-only state to an unlocked writeable state,
    wherein each of the one or more first memory blocks remains locked in the permanent read-only state responsive to execution of the recommission command by the controller.

16. The RFID tag of any one of clauses 1 to 13, wherein the first memory bank is locked in a non-permanent read-only state and/or the second memory bank is locked in the non-permanent read-only state, and further comprising a controller coupled to the memory device and configured to:
    receive a recommission command for the RFID tag; and
    responsive to receiving the recommission command:
        store data indicative that the RFID tag has been recommissioned in the RFID tag; and
        transition the first memory bank and/or the second memory bank from the non-permanent read-only state to an unlocked writeable state.

17. The RFID tag of any one of clauses 1 to 13 and 16, wherein the third memory bank is locked in a non-permanent read-only state, and further comprising a controller coupled to the memory device and configured to:
    receive a recommission command for the RFID tag; and
    responsive to receiving the recommission command:
        store data indicative that the RFID tag has been recommissioned in the RFID tag; and
        transition the third memory bank from the non-permanent read-only state to an unlocked writeable state.

18. The RFID tag of any one of clauses 1 to 17, further comprising a fourth memory bank storing an access password for selectively transitioning the RFID tag between a secured state and an open state, wherein the third memory bank is locked in a first non-permanent read-only state effective in the open state and not the secured state.

19. The RFID tag of any one of clauses 1 to 17, further comprising a fourth memory bank storing an access password for selectively transitioning the RFID tag between a secured state and an open state, wherein the first memory bank is locked in a second non-permanent read-only state effective in both the open state and the secured state and/or the second memory bank is locked in the second non-permanent read-only state effective in both the open state and the secured state.

20. A manifold configured to be coupled to a vacuum inlet integral with a medical waste collection device to provide suction at a surgical site through the manifold, the manifold including the RFID tag of any one of clauses 1 to 19.

21. A method for preparing an RFID tag for a manifold configured to be coupled to a vacuum inlet integral with a medical waste collection device to provide suction at a surgical site through the manifold, the method comprising:
  obtaining a memory device for the RFID tag, the memory device comprising a first memory bank storing an identifier for the RFID tag, a second memory bank for storing electronic identification data for the manifold, and a third memory bank for storing user data;
  writing to the third memory bank a rover type datum corresponding to the medical waste collection device, a first hash digest generated based on the rover type datum, use history data for the manifold, and a second hash digest generated based on the use history data for the manifold;
  writing a first portion of an originality signature for the manifold to the first memory bank, the originality signature for being read by the medical waste collection device when the manifold is proximate the medical waste collection device to control actuation of the medical waste collection device; and
  writing a second portion of the originality signature for the manifold to the second memory bank; and
  optionally, coupling the RFID tag to the manifold.

22. The method of clause 21, wherein the originality signature comprises a first sequence of bits and a second sequence of bits, and splitting the originality signature into a first portion and a second portion comprises:
  identifying as the first portion of the originality signature the first sequence of bits of the originality signature; and
  identifying as the second portion of the originality signature the second sequence of bits of the originality signature.

23. The method of clause 22, wherein the originality signature comprises the second sequence of bits appended to a least significant bit of the first sequence of bits.

24. The method of any one of clauses 21 to 23, wherein the first portion of the originality signature includes 16 bits, and the second portion of the originality signature includes 240 bits.

25. The method of any one of clauses 21 to 24, wherein the originality signature comprises 256 bits.

26. The method of any one of clauses 21 to 25, wherein the originality signature consists of 256 bits, the first portion of the originality signature consists of 16 bits, and the second portion of the originality signature consists of 240 bits.

27. The method of any one of clauses 21 to 26, further comprising locking the second memory bank in a read-only state with the second portion of the originality signature stored in the second memory bank.

28. The method of any one of clauses 21 to 27, wherein the third memory bank comprises a plurality of memory blocks, and further comprising locking one or more of the memory blocks ("first memory blocks") in a permanent read-only state such that one or more of the memory blocks ("second memory blocks") are not locked in the permanent read-only state according to a predefined lock pattern for verifying the RFID tag by the medical waste collection device.

29. The method of clause 28, wherein the first memory bank is locked in a non-permanent read-only state and/or the second memory bank is locked in the non-permanent read-only state, and further comprising obtaining a controller for the RFID tag that is coupled to the memory device and configured to:
  receive a recommission command for the RFID tag; and
  responsive to receiving the recommission command:
    store data indicative that the RFID tag has been recommissioned in the RFID tag; and
    transition the first memory bank and/or the second memory bank from the non-permanent read-only state to an unlocked writeable state,
    wherein each of the one or more first memory blocks remains locked in the permanent read-only state responsive to execution of the recommission command by the controller.

30. The method of clause 28 or 29, wherein the third memory bank is locked in a non-permanent read-only state, and further comprising obtaining a controller for the RFID tag that is coupled to the memory device and configured to:
  receive a recommission command for the RFID tag; and
  responsive to receiving the recommission command:
    store data indicative that the RFID tag has been recommissioned in the RFID tag; and
    transition the third memory bank from the non-permanent read-only state to an unlocked writeable state,
    wherein each of the one or more first memory blocks remains locked in the permanent read-only state responsive to execution of the recommission command by the controller.

31. The method of any one of clauses 21 to 28, wherein the first memory bank is locked in a non-permanent read-only state and/or the second memory bank is locked in the non-permanent read-only state, and further comprising obtaining a controller for the RFID tag that is coupled to the memory device and configured to:
  receive a recommission command for the RFID tag; and
  responsive to receiving the recommission command:
    store data indicative that the RFID tag has been recommissioned in the RFID tag; and
    transition the first memory bank and/or the second memory bank from the non-permanent read-only state to an unlocked writeable state.

32. The method of any one of clauses 21 to 28 and 31, wherein the third memory bank is locked in a non-permanent read-only state, and further comprising obtaining a controller for the RFID tag that is coupled to the memory device and configured to:
  receive a recommission command for the RFID tag; and
  responsive to receiving the recommission command:
    store data indicative that the RFID tag has been recommissioned in the RFID tag; and
    transition the third memory bank from the non-permanent read-only state to an unlocked writeable state.

33. The method of any one of clauses 21 to 32, wherein the memory device comprises a fourth memory bank, and further comprising:
  writing to the fourth memory bank an access password for selectively transitioning the RFID tag between a secured state and an open state; and
  locking the third memory bank in a first non-permanent read-only state that is effective in the open state and not the secured state.

34. The method of any one of clauses 21 to 33, wherein the memory device comprises a fourth memory bank, and further comprising:
  writing to the fourth memory bank an access password for selectively transitioning the RFID tag between a secured state and an open state; and
  locking the first memory bank and/or the second memory bank in a second non-permanent read-only state that is effective in both the secured state and the open state.

35. The method of any one of clauses 21 to 34, wherein writing to the third memory bank a rover type datum corresponding to the medical waste collection device, a first hash digest generated based on the rover type datum, use history data for the manifold, and a second hash digest generated based on the use history data for the manifold comprises:
   generating user data including the rover type datum corresponding to the medical waste collection device, the first hash digest generated based on the rover type datum, the use history data for the manifold, and the second hash digest generated based on the use history data for the manifold;
   encrypting the user data; and
   writing the encrypted user data to the third memory bank.

36. A set of manifolds each for connection with a medical waste collection device to provide suction at a surgical site through the manifold, the set of manifolds comprising:
   a first manifold and a second manifold, each of the first and second manifolds comprising:
      a manifold housing having a proximal region and a distal region and defining an internal fluid pathway between the proximal and distal regions;
      a plurality of inlet fittings disposed at the distal region of the manifold housing and each configured to be removably coupled with a suction tube;
      an outlet opening disposed at the proximal region of the manifold housing and configured to receive a suction inlet integral with the medical waste collection device for providing suction at the inlet fittings, wherein the outlet opening is in fluid communication with the inlet fittings through the internal fluid pathway defined by the manifold housing; and
      an RFID tag coupled to the manifold housing and storing an originality signature for the manifold for being read by the medical waste collection device when the manifold is proximate the medical waste collection device to control actuation of the medical waste collection device, wherein the originality signature for the first manifold differs from the originality signature for the second manifold, the RFID tag comprising:
         a first memory bank storing an identifier for the RFID tag and a first portion of the originality signature, the first portion of the originality signature being 16 bits in length;
         a second memory bank for storing electronic identification data for the manifold, the second memory bank storing a second portion of the originality signature, the second portion of the originality signature being 240 bits in length; and
         a third memory bank storing a rover type datum corresponding to the medical waste collection device, a first hash digest generated based on the rover type datum, use history data for the manifold, and a second hash digest generated based on the use history data for the manifold.

37. A medical waste collection system comprising:
   a medical waste collection device for providing suction at a surgical site;
   a manifold releasably couplable to the medical waste collection device and defining a pathway through which the medical waste collection device is configured to provide the suction to the surgical site, the manifold including an RFID tag including a first memory bank storing an identifier for the RFID tag and a first portion of an originality signature for the manifold, and a second memory bank for storing electronic identification data for the manifold, the second memory bank storing a second portion of the originality signature for the manifold; and
   a controller of the medical waste collection device that is configured to:
      responsive to the manifold being coupled to the medical waste collection device, read the first portion of the originality signature from the first memory bank and the second portion of the originality signature from the second memory bank;
      compile the originality signature based on the read first and second portions; and
      enable operation of the medical waste collection device to provide the suction at the surgical site based on the compiled originality signature.

38. The system of clause 37, wherein the first memory bank comprises a first sequence of bits at least 96 bits in length, the first sequence of bits including first bits storing the first portion of the originality signature and second bits storing the identifier for the RFID tag, and the controller is configured to:
   read the first sequence of bits of the first memory bank;
   extract the first portion of the originality signature from the read first sequence of bits;
   mask the first bits of the first sequence of bits to form a second sequence of bits including the masked bits and the second bits; and
   enable operation of the medical waste collection device to provide the suction at the surgical site based on the compiled originality signature and the second sequence of bits.

39. The system of clause 37 or 38, wherein the RFID tag further comprises a third memory bank for storing user data, the third memory bank including a plurality of memory blocks with one or more of the memory blocks ("first memory blocks") being locked in a permanent read-only state and one or more of the memory blocks ("second memory blocks") not being locked in the permanent read-only state according to a predefined lock pattern for verifying the RFID tag by the medical waste collection system, and the controller is configured to:
   determine that the first memory blocks are locked in the permanent read-only state and the second memory blocks are not locked in the permanent read-only state; and
   enable operation of the medical waste collection device to provide the suction at the surgical site responsive to determining that the first memory blocks are locked in the permanent read-only state and the second memory blocks are not locked in the permanent read-only state.

40. The system of clause 39, wherein the first memory bank is locked in a non-permanent read-only state and/or the second memory bank is locked in the non-permanent read-only state, and the controller is configured to:
   responsive to determining that the first memory blocks are locked in the permanent read-only state and the second memory blocks are not locked in the permanent read-only state, communicate a recommission command to the RFID tag, wherein responsive to receiving the recommission command, the RFID tag is configured to:
      store data indicative that the RFID tag has been recommissioned in the RFID tag; and
      transition the first memory bank and/or the second memory bank from the non-permanent read-only state to an unlocked writeable state,
   wherein each of the one or more first memory blocks remains locked in the permanent read-only state responsive to execution of the recommission command by the RFID tag.

41. The system of clause 39 or 40, wherein the third memory bank is locked in a non-permanent read-only state and the controller is configured to:
responsive to determining that the first memory blocks are locked in the permanent read-only state and the second memory blocks are not locked in the permanent read-only state, communicate a recommission command to the RFID tag, wherein responsive to receiving the recommission command, the RFID tag is configured to:
store data indicative that the RFID tag has been recommissioned in the RFID tag; and
transition the third memory bank from the non-permanent read-only state to an unlocked writeable state,
wherein each of the one or more first memory blocks remains locked in the permanent read-only state responsive to execution of the recommission command by the RFID tag.

42. The system of clause 40 or 41, wherein the controller is configured to, responsive to determining that the first memory blocks are locked in the permanent read-only state and the second memory blocks are not locked in the permanent read-only state:
instruct use history data for the manifold to be written to the third memory bank; and
after the use history data for the manifold is written to the third memory bank, communicate the recommission command to the RFID tag.

43. The system of any one of clauses 39 to 42, wherein the RFID tag comprises a fourth memory bank storing an access password for selectively transitioning the RFID tag between a secured state and an open state, the third memory bank is locked in a first non-permanent read-only state effective in the open state and not the secured state, and the controller is configured to:
determine that the third memory bank is locked in the first non-permanent read-only state using the access password; and
enable operation of the medical waste collection device to provide the suction at the surgical site responsive to determining that the first memory blocks are locked in the permanent read-only state, the second memory blocks are not locked in the permanent read-only state, and the third memory bank is locked in the first non-permanent read-only state.

44. The system of clause 43, wherein the controller is configured to, responsive to determining that the first memory blocks are locked in the permanent read-only state, the second memory blocks are not locked in the permanent read-only state, and the third memory bank is locked in the first non-permanent read-only state, communicate a recommission command to the RFID tag, wherein responsive to receiving the recommission command, the RFID tag is configured to:
store data indicative that the RFID tag has been recommissioned in the RFID tag; and
transition the third memory bank from the first non-permanent read-only state to an unlocked writeable state,
wherein each of the one or more first memory blocks remains locked in the permanent read-only state responsive to execution of the recommission command by the RFID tag.

45. The system of clause 44, wherein the controller is configured to, responsive to determining that the first memory blocks are locked in the permanent read-only state, the second memory blocks are not locked in the permanent read-only state, and the third memory bank is locked in the first non-permanent read-only state:
instruct use history data for the manifold to be written to the third memory bank when the RFID tag is in the secured state; and
after the use history data for the manifold is written to the third memory bank, communicate the recommission command to the RFID tag.

46. The system of any one of clauses 43 to 45, wherein the first memory bank is locked in a second non-permanent read-only state effective in both the secured state and the open state and/or the second memory bank is locked in the second non-permanent read-only state effective in both the secured state and the open state, and the controller is configured to:
determine that the first memory bank is locked in the second non-permanent read-only state and/or the second memory bank is locked in the second non-permanent read-only state using the access password; and
enable operation of the medical waste collection device to provide the suction at the surgical site responsive to determining that the first memory blocks are locked in the permanent read-only state, the second memory blocks are not locked in the permanent read-only state, the third memory bank is locked in the first non-permanent read-only state, and the first memory bank is locked in the second non-permanent read-only state and/or the second memory bank is locked in the second non-permanent read-only state.

47. The system of clause 46, wherein the controller is configured to, responsive to determining that the first memory blocks are locked in the permanent read-only state, the second memory blocks are not locked in the permanent read-only state, the third memory bank is locked in the first non-permanent read-only state, and the first memory bank is locked in the second non-permanent read-only state and/or the second memory bank is locked in a second non-permanent read-only state, communicate a recommission command to the RFID tag, wherein responsive to receiving the recommission command, the RFID tag is configured to:
store data indicative that the RFID tag has been recommissioned in the RFID tag;
transition the third memory bank from the first non-permanent read-only state to an unlocked writeable state; and
transition the first memory bank and/or the second memory bank from the second non-permanent read-only state to the unlocked writeable state.

48. The system of clause 47, wherein the controller is configured to, responsive to determining that the first memory blocks are locked in the permanent read-only state, the second memory blocks are not locked in the permanent read-only state, the third memory bank is locked in the first non-permanent read-only state, and the first memory bank is locked in the second non-permanent read-only state and/or the second memory bank is locked in the second non-permanent read-only state:
instruct use history data for the manifold to be written to the third memory bank; and
after the use history data for the manifold is written to the third memory bank, communicate the recommission command to the RFID tag.

49. The system of any one of clauses 37 to 49, wherein the RFID tag comprises a third memory bank for storing user data and a fourth memory bank storing an access password for selectively transitioning the RFID tag between a secured state and an open state, the third memory bank is locked in a first non-permanent read-only state effective in the open state and not the secured state, and the controller is configured to:
- determine that the third memory bank is locked in the first non-permanent read-only state using the access password; and
- enable operation of the medical waste collection device to provide the suction at the surgical site responsive to determining that the third memory bank is locked in the first non-permanent read-only state using the access password.

50. The system of clause 49, wherein the controller is configured to, responsive to determining that the third memory bank is locked in the first non-permanent read-only state, communicate a recommission command to the RFID tag, wherein responsive to receiving the recommission command, the RFID tag is configured to:
- store data indicative that the RFID tag has been recommissioned in the RFID tag; and
- transition the third memory bank from the first non-permanent read-only state to an unlocked writeable state.

51. The system of clause 50, wherein the controller is configured to, responsive to determining that the third memory bank is locked in the first non-permanent read-only state:
- instruct use history data for the manifold to be written to the third memory bank when the RFID tag is in the secured state; and
- after the use history data for the manifold is written to the third memory bank, communicate the recommission command to the RFID tag.

52. The system of any one of clauses 37 to 51, wherein the RFID tag comprises a fourth memory bank storing an access password for selectively transitioning the RFID tag between a secured state and an open state, the first memory bank is locked in a second non-permanent read-only state effective in both the secured state and the open state and/or the second memory bank is locked in the second non-permanent read-only state effective in both the secured state and the open state, and the controller is configured to:
- determine that the first memory bank is locked in the second non-permanent read-only state and/or the second memory bank is locked in the second non-permanent read-only state; and
- enable operation of the medical waste collection device to provide the suction at the surgical site responsive to determining that the first memory bank is locked in the second non-permanent read-only state and/or the second memory bank is locked in the second non-permanent read-only state.

53. The system of clause 52, wherein the controller is configured to, responsive to determining that the first memory bank is locked in the second non-permanent read-only state and/or the second memory bank is locked in the second non-permanent read-only state, communicate a recommission command to the RFID tag, wherein responsive to receiving the recommission command, the RFID tag is configured to:
- store data indicative that the RFID tag has been recommissioned in the RFID tag; and
- transition the first memory bank and/or the second memory bank from the second non-permanent read-only state to an unlocked writeable state.

54. The system of clause 53, wherein the RFID tag comprises a third memory bank for storing user data, and the controller is configured to, responsive to determining that the first memory bank is locked in the second non-permanent read-only state and/or the second memory bank is locked in the second non-permanent read-only state:
- instruct use history data for the manifold to be written to the third memory bank; and
- after the use history data for the manifold is written to the third memory bank, communicate the recommission command to the RFID tag.

55. A method for operating a medical waste collection system including a medical waste collection device for providing suction at a surgical site and a manifold releasably couplable to the medical waste collection device through which the medical waste collection device is configured to provide the suction to the surgical site, the manifold including an RFID tag including a first memory bank storing an identifier for the RFID tag and a first portion of an originality signature for the manifold, and a second memory bank for storing electronic identification data for the manifold, the second memory bank storing a second portion of the originality signature for the manifold, the method comprising:
- responsive to the manifold being coupled to the medical waste collection device, reading the first portion of the originality signature from the first memory bank and the second portion of the originality signature from the second memory bank;
- compiling the originality signature based on the read first and second portions; and
- enabling operation of the medical waste collection device to provide the suction at the surgical site based on the compiled originality signature.

56. The method of clause 55, wherein the first memory bank comprises a first sequence of bits at least 96 bits in length, the first sequence of bits including first bits storing the first portion of the originality signature and second bits storing the identifier for the RFID tag, and further comprising:
- reading the first sequence of bits from the first memory bank;
- extracting the first portion of the originality signature from the read first sequence of bits;
- masking the first bits of the first sequence of bits to form a second sequence of bits including the masked bits and the second bits; and
- enabling operation of the medical waste collection device to provide the suction at the surgical site based on the compiled originality signature and the second sequence of bits.

57. The method of clause 55 or 56, wherein the RFID tag further comprises a third memory bank for storing user data, the third memory bank including a plurality of memory blocks with one or more of the memory blocks ("first memory blocks") being locked in a permanent read-only state and one or more of the memory blocks ("second memory blocks") not being locked in the permanent read-only state according to a predefined lock pattern for verifying the RFID tag by the medical waste collection system, and further comprising:
- determining that the first memory blocks are locked in the permanent read-only state and the second memory blocks are not locked in the permanent read-only state; and
- enabling operation of the medical waste collection device to provide the suction at the surgical site responsive to determining that the first memory blocks are locked in the permanent read-only state and the second memory blocks are not locked in the permanent read-only state.

58. The method of clause 57, wherein the first memory bank is locked in a non-permanent read-only state and/or the second memory bank is locked in the non-permanent read-only state, and further comprising:
responsive to determining that the first memory blocks are locked in the permanent read-only state and the second memory blocks are not locked in the permanent read-only state, communicating a recommission command to the RFID tag, wherein responsive to receiving the recommission command, the RFID tag is configured to:
store data indicative that the RFID tag has been recommissioned in the RFID tag; and
transition the first memory bank and/or the second memory bank from the non-permanent read-only state to an unlocked writeable state,
wherein each of the one or more first memory blocks remains locked in the permanent read-only state responsive to execution of the recommission command by the RFID tag.

59. The method of clause 57 or 58, wherein the third memory bank is locked in a non-permanent read-only state, and further comprising:
responsive to determining that the first memory blocks are locked in the permanent read-only state and the second memory blocks are not locked in the permanent read-only state, communicating a recommission command to the RFID tag, wherein responsive to receiving the recommission command, the RFID tag is configured to:
store data indicative that the RFID tag has been recommissioned in the RFID tag; and
transition the third memory bank from the non-permanent read-only state to an unlocked writeable state,
wherein each of the one or more first memory blocks remains locked in the permanent read-only state responsive to execution of the recommission command by the RFID tag.

60. The method of clause 58 or 59, further comprising, responsive to determining that the first memory blocks are locked in the permanent read-only state and the second memory blocks are not locked in the permanent read-only state:
writing use history data for the manifold to the third memory bank; and
after the use history data for the manifold is written to the third memory bank, communicating the recommission command to the RFID tag.

61. The method of any one of clauses 57 to 60, wherein the RFID tag comprises a third memory bank for storing user data and a fourth memory bank storing an access password for selectively transitioning the RFID tag between a secured state and an open state, the third memory bank is locked in a first non-permanent read-only state effective in the open state and not the secured state, and further comprising:
determining that the third memory bank is locked in the first non-permanent read-only state using the access password; and
enabling operation of the medical waste collection device to provide the suction at the surgical site responsive to determining that the first memory blocks are locked in the permanent read-only state, the second memory blocks are not locked in the permanent read-only state, and the third memory bank is locked in the first non-permanent read-only state.

62. The method of clause 61, further comprising, responsive to determining that the first memory blocks are locked in the permanent read-only state, the second memory blocks are not locked in the permanent read-only state, and the third memory bank is locked in the first non-permanent read-only state, communicating a recommission command to the RFID tag, wherein responsive to receiving the recommission command, the RFID tag is configured to:
store data indicative that the RFID tag has been recommissioned in the RFID tag; and
transition the third memory bank from the first non-permanent read-only state to an unlocked writeable state,
wherein each of the one or more first memory blocks remains locked in the permanent read-only state responsive to execution of the recommission command by the RFID tag.

63. The method of clause 62, further comprising, responsive to determining that the first memory blocks are locked in the permanent read-only state, the second memory blocks are not locked in the permanent read-only state, and the third memory bank is locked in the first non-permanent read-only state:
writing use history data for the manifold to the third memory bank when the RFID tag is in the secured state; and
after the use history data for the manifold is written to the third memory bank, communicating the recommission command to the RFID tag.

64. The method of any one of clauses 61 to 63, wherein the first memory bank is locked in a second non-permanent read-only state effective in both the secured state and the open state and/or the second memory bank is locked in the second non-permanent read-only state effective in both the secured state and the open state, and further comprising:
determining that the first memory bank is locked in the second non-permanent read-only state and/or the second memory bank is locked in the second non-permanent read-only state; and
enabling operation of the medical waste collection device to provide the suction at the surgical site responsive to determining that the first memory blocks are locked in the permanent read-only state, the second memory blocks are not locked in the permanent read-only state, the third memory bank is locked in the first non-permanent read-only state, and the first memory bank is locked in the second non-permanent read-only state and/or the second memory bank is locked in the second non-permanent read-only state.

65. The method of clause 64, further comprising, responsive to determining that the first memory blocks are locked in the permanent read-only state, the second memory blocks are not locked in the permanent read-only state, the third memory bank is locked in the first non-permanent read-only state, and the first memory bank is locked in the second non-permanent read-only state and/or the second memory bank is locked in the second non-permanent read-only state, communicating a recommission command to the RFID tag, wherein responsive to receiving the recommission command, the RFID tag is configured to:
store data indicative that the RFID tag has been recommissioned in the RFID tag;
transition the third memory bank from the first non-permanent read-only state to an unlocked writeable state; and
transition the first memory bank and/or the second memory bank from the second non-permanent read-only state to the unlocked writeable state.

66. The method of clause 65, further comprising, responsive to determining that the first memory blocks are locked in the permanent read-only state, the second memory blocks are not locked in the permanent read-only state, the third memory bank is locked in the first non-permanent read-only state, and the first memory bank is locked in the second non-permanent read-only state and/or the second memory bank is locked in the second non-permanent read-only state:
  instructing use history data for the manifold to be written to the third memory bank; and
  after the use history data for the manifold is written to the third memory bank, communicating the recommission command to the RFID tag.

67. The method of any one of clauses 55 to 60, wherein the RFID tag comprises a third memory bank for storing user data and a fourth memory bank storing an access password for selectively transitioning the RFID tag between a secured state and an open state, the third memory bank is locked in a first non-permanent read-only state effective in the open state and not the secured state, and further comprising:
  determining that the third memory bank is locked in the first non-permanent read-only state using the access password; and
  enabling operation of the medical waste collection device to provide the suction at the surgical site responsive to determining that the third memory bank is locked in the first non-permanent read-only state using the access password.

68. The method of clause 67, further comprising, responsive to determining that the third memory bank is locked in the first non-permanent read-only state, communicating a recommission command to the RFID tag, wherein responsive to receiving the recommission command, the RFID tag is configured to:
  store data indicative that the RFID tag has been recommissioned in the RFID tag; and
  transition the third memory bank from the first non-permanent read-only state to an unlocked writeable state.

69. The method of clause 68, further comprising, responsive to determining that the third memory bank is locked in the first non-permanent read-only state:
  writing use history data for the manifold to the third memory bank when the RFID tag is in the secured state; and
  after the use history data for the manifold is written to the third memory bank, communicating the recommission command to the RFID tag.

70. The method of any one of clauses 55 to 69, wherein the RFID tag comprises a fourth memory bank storing an access password for selectively transitioning the RFID tag between a secured state and an open state, the first memory bank is locked in a second non-permanent read-only state effective in both the secured state and the open state and/or the second memory bank is locked in a second non-permanent read-only state effective in both the secured state and the open state, and further comprising:
  determining the first memory bank is locked in the second non-permanent read-only state and/or the second memory bank is locked in the second non-permanent read-only state; and
  enabling operation of the medical waste collection device to provide the suction at the surgical site responsive to determining that the first memory bank is locked in the second non-permanent read-only state and/or the second memory bank is locked in the second non-permanent read-only state.

71. The method of clause 70, further comprising, responsive to determining that the first memory bank is locked in the second non-permanent read-only state and/or the second memory bank is locked in the second non-permanent read-only state, communicating a recommission command to the RFID tag, wherein responsive to receiving the recommission command, the RFID tag is configured to:
  store data indicative that the RFID tag has been recommissioned in the RFID tag; and
  transition the first memory bank and/or the second memory bank from the second non-permanent read-only state to an unlocked writeable state.

72. The method of clause 71, wherein the RFID tag comprises a third memory bank for storing user data, and further comprising, responsive to determining that the first memory bank is locked in the second non-permanent read-only state and/or the second memory bank is locked in the second non-permanent read-only state:
  instructing use history data for the manifold to be written to the third memory bank; and
  after the use history data for the manifold is written to the third memory bank, communicating the recommission command to the RFID tag.

73. A memory device for a medical/surgical device or a medical/surgical device including the memory device or a controller for the medical/surgical device including the memory device, the memory device comprising:
  a first memory bank storing an identifier for the memory device;
  a second memory bank storing electronic identification data for the medical/surgical device; and
  a third memory bank comprising a plurality of memory blocks with one or more of the memory blocks ("first memory blocks") being locked in a permanent read-only state and one or more of the memory blocks ("second memory blocks") not being locked in the permanent read-only state according to a predefined lock pattern for verifying the memory device by a reader.

74. A memory device for a medical/surgical device or a medical/surgical device including the memory device or a controller for the medical/surgical device including the memory device, the memory device comprising:
  a non-transitory computer-readable storage medium storing an originality signature for the medical/surgical device, the originality signature for being read by a reader when the medical/surgical device is proximate the reader, the non-transitory computer-readable storage medium comprising:
    a first memory bank storing an identifier for the memory device and a first portion of the originality signature, the first portion having a character length of at least 16 bits;
    a second memory bank for storing electronic identification data for the medical/surgical device, the second memory bank storing a second portion of the originality signature, the second portion having a character length of at least 240 bits; and
    a third memory bank storing a compatibility datum for the medical/surgical device, a first hash digest generated based on the compatibility datum, use history data for the medical/surgical device, and a second hash digest generated based on the use history data for the medical/surgical device.

75. An RFID tag for a manifold configured to be coupled to a vacuum inlet integral with a medical waste collection device to provide suction at a surgical site through the manifold or a manifold including an RFID tag or a manifold including the RFID tag, the RFID tag comprising:
  a memory device storing data for being read by the medical waste collection device when the manifold is proximate the medical waste collection device to control actuation of the medical waste collection device, the memory device comprising:
- a first memory bank storing an identifier for the RFID tag;
- a second memory bank storing electronic identification data for the manifold; and
- a third memory bank comprising a plurality of memory blocks with one or more of the memory blocks ("first memory blocks") being locked in a permanent read-only state and one or more of the memory blocks ("second memory blocks") not being locked in the permanent read-only state according to a predefined lock pattern for verifying the RFID tag by the medical waste collection device,
- wherein the memory device further stores an originality signature for being read by the medical waste collection device when the manifold is proximate the medical waste collection device to control actuation of the medical waste collection device, the originality signature being split between at least two of the first, second, and third memory banks.

76. A method for preparing an RFID tag for a manifold configured to be coupled to a vacuum inlet integral with a medical waste collection device to provide suction at a surgical site through the manifold, the method comprising:
- obtaining a memory device for the RFID tag, the memory device comprising a first memory bank storing an identifier for the RFID tag, a second memory bank for storing electronic identification data for the manifold, and a third memory bank for storing user data, the third memory bank comprising a plurality of memory blocks;
- writing to the third memory bank a rover type datum corresponding to the medical waste collection device, a first hash digest generated based on the rover type datum, use history data for the manifold, and a second hash digest generated based on the use history data for the manifold;
- locking one or more of the memory blocks of the third memory bank ("first memory blocks") in a permanent read-only state such that one or more of the memory blocks ("second memory blocks") of the third memory bank are not locked in the permanent read-only state according to a predefined lock pattern for verifying the RFID tag by the medical waste collection device; and
- storing a split originality signature for manifold among at least two of the first, second, and third memory banks, the originality signature for being read by the medical waste collection device when the manifold is proximate the medical waste collection device to control actuation of the medical waste collection device; and
- optionally, coupling the RFID tag to the manifold.

77. A memory device for a medical/surgical device or a medical/surgical device including the memory device or a controller for the medical/surgical device including the memory device, the memory device comprising:
- a non-transitory computer readable storage medium storing data for being read by a reader when the medical/surgical device is proximate the reader, the non-transitory computer readable storage medium comprising:
  - a first memory bank storing an identifier for the memory device;
  - a second memory bank storing electronic identification data for the medical/surgical device; and
  - a third memory bank comprising a plurality of memory blocks with one or more of the memory blocks ("first memory blocks") being locked in a permanent read-only state and one or more of the memory blocks ("second memory blocks") not being locked in the permanent read-only state according to a predefined lock pattern for verifying the memory device,
- wherein the non-transitory computer readable storage medium further stores an originality signature for being read by the reader when the medical/surgical device is proximate the reader, the originality signature being split between at least two of the first, second, and third memory banks.

78. An RFID tag for a manifold configured to be coupled to a vacuum inlet integral with a medical waste collection device to provide suction at a surgical site through the manifold or a manifold including an RFID tag, the RFID tag comprising:
- a memory device storing data for being read by the medical waste collection device when the manifold is proximate the medical waste collection device to control actuation of the medical waste collection device, the memory device comprising:
  - a first memory bank storing an identifier for the RFID tag;
  - a second memory bank storing electronic identification data for the manifold; and
  - a third memory bank comprising a plurality of memory blocks with one or more of the memory blocks ("first memory blocks") being locked in a permanent read-only state and one or more of the memory blocks ("second memory blocks") not being locked in the permanent read-only state according to a predefined lock pattern for verifying the RFID tag by the medical waste collection device.

79. The RFID tag of clause 78, wherein the third memory bank stores first user data indicating a rover type datum corresponding to the medical waste collection device and a first hash digest generated based on the rover type datum, and stores second user data indicating use history data for the manifold and a second hash digest generated based on the use history data for the manifold.

80. The RFID tag of clause 79, wherein the second user data is stored in the one or more second memory blocks.

81. The RFID tag of clause 79 or 80, wherein at least a portion of the first user data is stored in the one or more first memory blocks.

82. The RFID tag of any one of clauses 78 to 81, wherein the first memory bank has a capacity of 96 bits, and the second memory bank has a capacity of at least 304 bits.

83. The RFID tag of any one of clauses 78 to 82, wherein the memory device comprises four memory banks.

84. The RFID tag of any one of clauses 78 to 83, wherein the first memory bank further stores a mask designer identifier for the RFID tag and a model number of the RFID tag.

85. The RFID tag of any one of clauses 78 to 84, wherein the one or more first memory blocks comprises a plurality of first memory blocks, the plurality of first memory blocks being interspaced by at least one of the one or more second memory blocks within the third memory bank.

86. The RFID tag of any one of clauses 78 to 85, wherein the one or more first memory blocks comprises two first memory blocks and the one or more second memory blocks comprises four second memory blocks.

87. The RFID tag of clause 86, wherein the one or more first memory blocks comprises three first memory blocks and the one or more second memory blocks comprises five second memory blocks, wherein, optionally, the one or more first memory blocks consists of three first memory blocks and the one or more second memory blocks consists of five second memory blocks.

88. The RFID tag of any one of clauses 78 to 87, wherein the third memory bank is locked in a non-permanent read-only state according to the predefined lock pattern for verifying the RFID tag by the medical waste collection device.

89. The RFID tag of clause 88, further comprising a controller coupled to the memory device and configured to:
  receive a recommission command for the RFID tag; and
  responsive to receiving the recommission command:
    store data indicative that the RFID tag has been recommissioned in the RFID tag, and
    transition the third memory bank from the non-permanent read-only state to an unlocked writeable state,
  wherein each of the one or more first memory blocks remains locked in the permanent read-only state responsive to execution of the recommission command by the controller.

90. The RFID tag of any one of clauses 78 to 13, further comprising a fourth memory bank storing an access password for selectively transitioning the RFID tag between a secured state and an open state, wherein the third memory bank is locked in a first non-permanent read-only state effective in the open state and not the secured state according to the predefined lock pattern for verifying the RFID tag by the medical waste collection device.

91. The RFID tag of any one of clauses 78 to 14, further comprising a fourth memory bank storing an access password for selectively transitioning the RFID tag between a secured state and an open state, wherein the second memory bank is locked in a second non-permanent read-only state effective in the open state and the secured state according to the predefined lock pattern for verifying the RFID tag by the medical waste collection device.

92. A manifold configured to be coupled to a vacuum inlet integral with a medical waste collection device to provide suction at a surgical site through the manifold, the manifold including the RFID tag of any one of clauses 1 to 15.

93. A method for preparing an RFID tag for a manifold configured to be coupled to a vacuum inlet integral with a medical waste collection device to provide suction at a surgical site through the manifold, the method comprising:
  obtaining a memory device for the RFID tag, the memory device comprising a first memory bank storing an identifier for the RFID tag, a second memory bank for storing electronic identification data for the manifold, and a third memory bank for storing user data, the third memory bank comprising a plurality of memory blocks;
  writing to the third memory bank a rover type datum corresponding to the medical waste collection device, a first hash digest generated based on the rover type datum, use history data for the manifold, and a second hash digest generated based on the use history data for the manifold; and
  locking one or more of the memory blocks of the third memory bank ("first memory blocks") in a permanent read-only state such that one or more of the memory blocks ("second memory blocks") of the third memory bank are not locked in the permanent read-only state according to a predefined lock pattern for verifying the RFID tag by the medical waste collection device; and
  optionally, coupling the RFID tag to the manifold.

94. The method of clause 93, further comprising writing first user data indicating the rover type datum and the first hash digest to the third memory bank such that at least a portion of the first user data is stored in the one or more first memory blocks.

95. The method of clause 93 or 94, further comprising writing second user data indicating the use history data for the manifold and the second hash digest generated based on the use history data for the manifold to the one or more second memory blocks.

96. The method of any one of clauses 93 to 95, wherein the one or more first memory blocks comprises a plurality of first memory blocks, and further comprising locking the first memory blocks according to the predefined lock pattern for verifying the RFID tag by the medical waste collection device such that the plurality of first memory blocks are interspaced by at least one of the one or more second memory blocks within the third memory bank.

97. The method of any one of clauses 93 to 96, wherein locking the one or more first memory blocks of the third memory bank in a permanent read-only state such that the one or more second memory blocks of the third memory bank are not locked in the permanent read-only state according to a predefined lock pattern for verifying the RFID tag by the medical waste collection device comprises locking at least two of the memory blocks of the third memory bank in the permanent read-only state such that at least four of the memory blocks of the third memory bank are not locked in the permanent read-only state according to the predefined lock pattern for verifying the RFID tag by the medical waste collection device.

98. The method of any one of clauses 93 to 97, wherein locking the one or more first memory blocks of the third memory bank in a permanent read-only state such that the one or more second memory blocks of the third memory bank are not locked in the permanent read-only state according to a predefined lock pattern for verifying the RFID tag by the medical waste collection device comprises locking at least three of the memory blocks of the third memory bank in the permanent read-only state such that at least five of the memory blocks of the third memory bank are not locked in the permanent read-only state according to the predefined lock pattern for verifying the RFID tag by the medical waste collection device.

99. The method of any one of clauses 93 to 98, wherein locking the one or more first memory blocks of the third memory bank in a permanent read-only state such that the one or more second memory blocks of the third memory bank are not locked in the permanent read-only state according to a predefined lock pattern for verifying the RFID tag by the medical waste collection device consists of locking three of the memory blocks of the third memory bank in the permanent read-only state such that five of the memory blocks of the third memory bank are not locked in the permanent read-only state according to the predefined lock pattern for verifying the RFID tag by the medical waste collection device.

100. The method of any one of clauses 93 to 99, further comprising locking the third memory bank in a non-permanent read-only state according to the predefined lock pattern for verifying the RFID tag by the medical waste collection device.

101. The method of clause 100 further comprising obtaining a controller for the RFID tag that is coupled to the memory device and configured to:
  receive a recommission command for the RFID tag; and
  responsive to receiving the recommission command:
    store data indicative that the RFID tag has been recommissioned in the RFID tag; and transition the third memory bank from the non-permanent read-only state to an unlocked writeable state, wherein each of the one or more first memory blocks remains locked in the permanent read-only state responsive to execution of the recommission command by the controller.

102. The method of any one of clauses 93 to 101, wherein the memory device further comprises a fourth memory bank, and further comprising:
   writing to the fourth memory bank an access password for selectively transitioning the RFID tag between a secured state and an open state; and
   locking the third memory bank in a first non-permanent read-only state that is effective in the open state and not the secured state according to the predefined lock pattern for verifying the RFID tag by the medical waste collection device.

103. The method of any one of clauses 93 to 102, wherein the memory device further comprises a fourth memory bank, and further comprising:
   writing to the fourth memory bank an access password for selectively transitioning the RFID tag between a secured state and an open state; and
   locking the second memory bank in a second non-permanent read-only state that is effective in both the open state and the secured state according to the predefined lock pattern for verifying the RFID tag by the medical waste collection device.

104. The method of any one of clauses 93 to 103, wherein writing to the third memory bank a rover type datum corresponding to the medical waste collection device, a first hash digest generated based on the rover type datum, use history data for the manifold, and a second hash digest generated based on the use history data for the manifold comprises:
   generating user data including the rover type datum corresponding to the medical waste collection device, the first hash digest generated based on the rover type datum, the use history data for the manifold, and the second hash digest generated based on the use history data for the manifold;
   encrypting the user data; and
   writing the encrypted user data to the third memory bank.

105. A medical waste collection system comprising:
   a medical waste collection device for providing suction at a surgical site;
   a manifold releasably couplable to the medical waste collection device and defining a pathway through which the medical waste collection device is configured to provide the suction to the surgical site, the manifold including an RFID tag including a first memory bank storing an identifier for the RFID tag, a second memory bank for storing electronic identification data for the manifold, and a third memory bank for storing user data, the third memory bank including a plurality of memory blocks with one or more of the memory blocks ("first memory blocks") being locked in a permanent read-only state and one or more of the memory blocks ("second memory blocks") not being locked in the permanent read-only state according to a predefined lock pattern for verifying the RFID tag by the medical waste collection system; and
   a controller of the medical waste collection device that is configured to, responsive to the manifold being coupled to the medical waste collection device:
      determine that the first memory blocks each exhibits a behavioral characteristic consistent with the permanent read-only state and the second memory blocks each does not exhibit the behavioral characteristic of the permanent read-only state; and
      enable operation of the medical waste collection device to provide the suction at the surgical site responsive to determining that the first memory blocks each exhibits the behavioral characteristic consistent with the permanent read-only state and the second memory blocks each does not exhibit the behavioral characteristic of the permanent read-only state.

106. The system of clause 105, wherein the controller is configured to determine that the first memory blocks each exhibits a behavioral characteristic consistent with the permanent read-only state and the second memory blocks each does not exhibit the behavioral characteristic of the permanent read-only state by being configured to determine that the RFID tag is in a non-recommissioned state, and that the first memory blocks are each read-only and the second memory blocks are each not read-only when the RFID tag is in the non-recommissioned state.

107. The system of clause 105 or 106, wherein the behavioral characteristic is a first behavioral characteristic, and the controller is configured to, responsive to determining that the first memory blocks each exhibits the first behavioral characteristic consistent with the permanent read-only state:
   communicate a recommission command to the RFID tag;
   responsive to the RFID tag executing the recommission command, determine that the first memory blocks each exhibits a second behavioral characteristic consistent with the permanent read-only state; and
   enable operation of the medical waste collection device to provide the suction at the surgical site responsive to determining that each of the first memory blocks exhibits the second behavioral characteristic consistent with the permanent read-only state.

108. The system of clause 107, wherein the controller is configured to determine that the first memory blocks each exhibits the second behavioral characteristic consistent with the permanent read-only state by being configured to determine that the first memory blocks each is read-only following the execution of the recommission command by the RFID tag.

109. The system of clause 105, wherein the controller is configured to determine that the first memory blocks each exhibits a behavioral characteristic consistent with the permanent read-only state and the second memory blocks each does not exhibit the behavioral characteristic of the permanent read-only state by being configured to:
   communicate a lock status inquiry to the RFID tag for each of the memory blocks; and
   determine that the first memory blocks each exhibits the behavioral characteristic consistent with the permanent read-only state and the second memory blocks each does not exhibit the behavioral characteristic consistent with the permanent read-only state based on a reply received from the RFID tag for the lock status inquiry communicated for each of the memory blocks.

110. The system of any one of clauses 105 to 109, wherein the third memory bank is locked in a non-permanent read-only state, and the controller is configured to:
   determine that the third memory bank exhibits a behavioral characteristic consistent with the non-permanent read-only state; and
   enable operation of the medical waste collection device to provide the suction at the surgical site responsive to determining that the first memory blocks each exhibits the behavioral characteristic consistent with the permanent read-only state, the second memory blocks each does not exhibit the behavioral characteristic consistent with the permanent read-only state, and the third memory bank exhibits the behavioral characteristic consistent with the non-permanent read-only state.

111. The system of clause 110, wherein the controller is configured to determine that the third memory bank exhibits the behavioral characteristic consistent with the non-permanent read-only state by being configured to determine that the RFID tag is in a non-recommissioned state and the third memory bank is read-only when the RFID tag is in the non-recommissioned state.

112. The system of clause 110 or 111, wherein the controller is configured to, responsive to determining that the first memory blocks each exhibits the behavioral characteristic consistent with the permanent read-only state, the second memory blocks each does not exhibit the behavioral characteristic consistent with the permanent read-only state, and the third memory bank exhibits a behavioral characteristic consistent with the non-permanent read-only state, communicate a recommission command to the RFID tag, wherein responsive to receiving the recommission command, the RFID tag is configured to:
 store data indicative that the RFID tag has been recommissioned in the RFID tag; and
 transition the third memory bank from the non-permanent read-only state to an unlocked writeable state,
 wherein each of the one or more first memory blocks remains locked in the permanent read-only state responsive to execution of the recommission command by the RFID tag.

113. The system of clause 112, wherein the behavioral characteristic consistent with the non-permanent read-only state is a first behavioral characteristic consistent with the non-permanent read-only state, and the controller is configured to, responsive to the RFID tag executing the recommission command:
 determine that the third memory bank exhibits a second behavioral characteristic consistent with the non-permanent read-only state by determining that the third memory bank is in the unlocked writeable state; and
 enable operation of the medical waste collection device to provide the suction at the surgical site responsive to determining that the third memory bank exhibits the second behavioral characteristic consistent with the non-permanent read-only state.

114. The system of any one of clauses 105 to 113, wherein the RFID tag further comprises a fourth memory bank storing an access password for selectively transitioning the RFID tag between a secured state and an open state, the third memory bank is locked in a first non-permanent read-only state effective in the open state and not the secured state, and the controller is configured to:
 determine that the third memory bank exhibits a behavioral characteristic consistent with the first non-permanent read-only state using the access password; and
 enable operation of the medical waste collection device to provide the suction at the surgical site responsive to determining that the first memory blocks each exhibits the behavioral characteristic consistent with the permanent read-only state, the second memory blocks each does not exhibit the behavioral characteristic consistent with the permanent read-only state, and the third memory bank exhibits the behavioral characteristic consistent with the first non-permanent read-only state.

115. The system of clause 114, wherein the controller is configured to determine that the third memory bank exhibits a behavioral characteristic consistent with the first non-permanent read-only state using the access password by being configured to:
 communicate a first write command for the third memory bank to the RFID tag when the RFID tag is in the open state;
 determine that the first write command fails;
 responsive to determining that the first write command fails, transition the RFID tag to the secured state using the access password; and
 communicate a second write command for the third memory bank to the RFID tag when the RFID tag is in the secured state;
 determine that the second write command succeeds; and
 determine that the third memory bank exhibits the behavioral characteristic consistent with the first non-permanent read-only state responsive to determining that the second write command succeeds.

116. The system of clause 114 or 115, wherein the controller is configured to, responsive to determining that the first memory blocks each includes the characteristic consistent with the permanent read-only state, the second memory blocks each does not include the characteristic consistent with the permanent read-only state, and the third memory bank includes the characteristic consistent with the first non-permanent read-only state, communicate a recommission command to the RFID tag, wherein responsive to receiving the recommission command, the RFID tag is configured to:
 store data indicative that the RFID tag has been recommissioned in the RFID tag; and
 transition the third memory bank from the non-permanent read-only state to an unlocked writeable state,
 wherein each of the one or more first memory blocks remains locked in the permanent read-only state responsive to execution of the recommission command by the RFID tag.

117. The system of clause 116, wherein the behavioral characteristic consistent with the first non-permanent read-only state is a first behavioral characteristic of the first non-permanent read-only state, and the controller is configured to, responsive to the RFID tag executing the recommission command:
 determine that the third memory bank exhibits a second behavioral characteristic consistent with the first non-permanent read-only state by determining that the memory bank is in the unlocked writeable state; and
 enable operation of the medical waste collection device to provide the suction at the surgical site responsive to determining that the third memory bank exhibits the second behavioral characteristic consistent with the first non-permanent read-only state.

118. The system of any one of clauses 114 to 117, wherein the second memory bank is locked in a second non-permanent read-only state effective in both the open state and the secured state according to the predefined lock pattern for verifying the RFID tag by the medical waste collection system, and the controller is configured to:
 determine that the second memory bank exhibits a behavioral characteristic consistent with the second non-permanent read-only state using the access password; and
 enable operation of the medical waste collection device to provide the suction at the surgical site responsive to determining that the first memory blocks each includes the behavioral characteristic consistent with the permanent read-only state, the second memory blocks each does not include the behavioral characteristic consistent with the permanent read-only state, the third memory bank includes the behavioral characteristic consistent with the first non-permanent read-only state and the second memory bank includes the behavioral characteristic consistent with the second non-permanent read-only state.

119. The system of clause 118, wherein the controller configured is configured to determine that the second memory bank exhibits a behavioral characteristic consistent with the second non-permanent read-only state using the access password by being configured to:
   communicate a first write command for the second memory bank to the RFID tag when the RFID tag is in the open state;
   determine that the first write command fails;
   responsive to determining that the first write command fails, transition the RFID tag to the secured state using the access password; and
   communicate a second write command for the second memory bank to the RFID tag when the RFID tag is in the secured state;
   determine that the second write command fails; and
   determine that the second memory bank exhibits the behavioral characteristic consistent with the second non-permanent read-only state responsive to determining that the second write command fails.

120. The system of clause 118 or 119, wherein the controller is configured to, responsive to determining that the first memory blocks each includes the behavioral characteristic consistent with the permanent read-only state, the second memory blocks each does not include the behavioral characteristic consistent with the permanent read-only state, the third memory bank includes the behavioral characteristic consistent the first non-permanent read-only state, and the second memory bank includes the behavioral characteristic consistent with the second non-permanent read-only state, communicate a recommission command to the RFID tag, wherein responsive to receiving the recommission command, the RFID tag is configured to:
   store data indicative that the RFID tag has been recommissioned in the RFID tag; and
   transition the third memory bank from the first non-permanent read-only state and the second memory bank from the second non-permanent read-only state to an unlocked writeable state,
   wherein each of the one or more first memory blocks remains locked in the permanent read-only state responsive to execution of the recommission command by the RFID tag.

121. The system of clause 120, wherein the behavioral characteristic consistent with the second non-permanent read-only state is a first behavioral characteristic consistent with the second non-permanent read-only state, and the controller is configured to, responsive to the RFID tag executing the recommission command:
   determine that the second memory bank exhibits a second behavioral characteristic consistent with the second non-permanent read-only state by determining that the second memory bank is in an unlocked writeable state; and
   enable operation of the medical waste collection device to provide the suction at the surgical site responsive to determining that the second memory bank exhibits the second behavioral characteristic consistent with the second non-permanent read-only state.

122. The system of any one of clauses 114 to 121, wherein the controller is configured to, responsive to determining that the first memory blocks each includes the behavioral characteristic consistent with the permanent read-only state, the second memory blocks each does not include the behavioral characteristic consistent with the permanent read-only state, and the third memory bank includes the behavioral characteristic consistent the first non-permanent read-only state:
   communicate use history data for the manifold to the RFID tag to be written in the third memory bank when the RFID tag is in the secured state; and
   after the use history data for the manifold is written to the third memory bank, communicate the recommission command to the RFID tag.

123. A method for operating a medical waste collection system including a medical waste collection device for providing suction at a surgical site and a manifold releasably couplable to the medical waste collection device through which the medical waste collection device is configured to provide the suction to the surgical site, the manifold including an RFID tag including a first memory bank storing an identifier for the RFID tag, a second memory bank for storing electronic identification data for the manifold, and a third memory bank for storing user data, the third memory bank including a plurality of memory blocks with one or more of the memory blocks ("first memory blocks") being locked in a permanent read-only state and one or more of the memory blocks ("second memory blocks") not being locked in the permanent read-only state according to a predefined lock pattern for verifying the RFID tag by the medical waste collection system, the method comprising:
   responsive to the manifold being coupled to the medical waste collection device:
      determining that the first memory blocks each exhibits a behavioral characteristic consistent with the permanent read-only state and the second memory blocks each does not include the characteristic of the permanent read-only state; and
      enabling operation of the medical waste collection device to provide the suction at the surgical site responsive to determining that the first memory blocks each includes the characteristic of the permanent read-only state and the second memory blocks each does not include the characteristic of the permanent read-only state.

124. The method of clause 123, wherein determining that the first memory blocks each exhibits a behavioral characteristic consistent with the permanent read-only state and the second memory blocks each does not exhibit the behavioral characteristic of the permanent read-only state comprises determining that the RFID tag is in a non-recommissioned state, and that the first memory blocks are each read-only and the second memory blocks are each not read-only when the RFID tag is in the non-recommissioned state.

125. The method of clause 123 or 124, wherein the behavioral characteristic is a first behavioral characteristic, and further comprising, responsive to determining that the first memory blocks each exhibits the first behavioral characteristic consistent with the permanent read-only state:
   communicating a recommission command to the RFID tag;
   responsive to the RFID tag executing the recommission command, determining that the first memory blocks each exhibits a second behavioral characteristic consistent with the permanent read-only state; and enabling operation of the medical waste collection device to provide the suction at the surgical site responsive to determining that each of the first memory blocks exhibits the second behavioral characteristic consistent with the permanent read-only state.

126. The method of clause 125, further comprising determining that the first memory blocks each exhibits the second behavioral characteristic consistent with the permanent read-only state by determining that the first memory blocks each is read-only following the execution of the recommission command by the RFID tag.

127. The method of clause 123, wherein determining that the first memory blocks each exhibits a behavioral characteristic consistent with the permanent read-only state and the second memory blocks each does not exhibit the behavioral characteristic of the permanent read-only state comprises:
communicating a lock status inquiry to the RFID tag for each of the memory blocks; and
determining that the first memory blocks each exhibits the behavioral characteristic consistent with the permanent read-only state and the second memory blocks each does not exhibit the behavioral characteristic consistent with the permanent read-only state based on a reply received from the RFID tag for the lock status inquiry communicated for each of the memory blocks.

128. The method of any one of clauses 123 to 127, wherein the third memory bank is locked in a non-permanent read-only state, and further comprising:
determining that the third memory bank exhibits a behavioral characteristic consistent with the non-permanent read-only state; and
enabling operation of the medical waste collection device to provide the suction at the surgical site responsive to determining that the first memory blocks each exhibits the behavioral characteristic consistent with the permanent read-only state, the second memory blocks each does not exhibit the behavioral characteristic consistent with the permanent read-only state, and the third memory bank exhibits the behavioral characteristic consistent with the non-permanent read-only state.

129. The method of clause 128, wherein determining that the third memory bank exhibits the behavioral characteristic consistent with the non-permanent read-only state comprises determining that the RFID tag is in a non-recommissioned state and the third memory bank is read-only when the RFID tag is in the non-recommissioned state.

130. The method of clause 128 or 129, further comprising, responsive to determining that the first memory blocks each exhibits the behavioral characteristic consistent with the permanent read-only state, the second memory blocks each does not exhibit the behavioral characteristic consistent with the permanent read-only state, and the third memory bank exhibits a behavioral characteristic consistent with the non-permanent read-only state, communicating a recommission command to the RFID tag, wherein responsive to receiving the recommission command, the RFID tag is configured to:
store data indicative that the RFID tag has been recommissioned in the RFID tag; and
transition the third memory bank from the non-permanent read-only state to an unlocked writeable state,
wherein each of the one or more first memory blocks remains locked in the permanent read-only state responsive to execution of the recommission command by the RFID tag.

131. The method of clause 130, wherein the behavioral characteristic consistent with the non-permanent read-only state is a first behavioral characteristic consistent with the non-permanent read-only state, and further comprising, responsive to the RFID tag executing the recommission command:
determining that the third memory bank exhibits a second behavioral characteristic consistent with the non-permanent read-only state by determining that the third memory bank is in the unlocked writeable state; and
enabling operation of the medical waste collection device to provide the suction at the surgical site responsive to determining that the third memory bank exhibits the second behavioral characteristic consistent with the non-permanent read-only state.

132. The method of any one of clauses 123 to 131, wherein the RFID tag further comprises a fourth memory bank storing an access password for selectively transitioning the RFID tag between a secured state and an open state, the third memory bank is locked in a first non-permanent read-only state effective in the open state and not the secured state, and further comprising:
determining that the third memory bank exhibits a behavioral characteristic consistent with the first non-permanent read-only state using the access password; and
enabling operation of the medical waste collection device to provide the suction at the surgical site responsive to determining that the first memory blocks each exhibits the behavioral characteristic consistent with the permanent read-only state, the second memory blocks each does not exhibit the behavioral characteristic consistent with the permanent read-only state, and the third memory bank exhibits the behavioral characteristic consistent with the first non-permanent read-only state.

133. The method of clause 132, wherein determining that the third memory bank exhibits a behavioral characteristic consistent with the first non-permanent read-only state using the access password comprises:
communicating a first write command for the third memory bank to the RFID tag when the RFID tag is in the open state;
determining that the first write command fails;
responsive to determining that the first write command fails, transitioning the RFID tag to the secured state using the access password; and
communicating a second write command for the third memory bank to the RFID tag when the RFID tag is in the secured state;
determining that the second write command succeeds; and
determining that the third memory bank exhibits the behavioral characteristic consistent with the first non-permanent read-only state responsive to determining that the second write command succeeds.

134. The method of clause 132 or 133, further comprising, responsive to determining that the first memory blocks each includes the characteristic consistent with the permanent read-only state, the second memory blocks each does not include the characteristic consistent with the permanent read-only state, and the third memory bank includes the characteristic consistent with the first non-permanent read-only state, communicating a recommission command to the RFID tag, wherein responsive to receiving the recommission command, the RFID tag is configured to:
store data indicative that the RFID tag has been recommissioned in the RFID tag; and
transition the third memory bank from the non-permanent read-only state to an unlocked writeable state, wherein each of the one or more first memory blocks remains locked in the permanent read-only state responsive to execution of the recommission command by the RFID tag.

135. The method of clause 134, wherein the behavioral characteristic consistent with the first non-permanent read-only state is a first behavioral characteristic of the first non-permanent read-only state, and further comprising, responsive to the RFID tag executing the recommission command:
   determining that the third memory bank exhibits a second behavioral characteristic consistent with the first non-permanent read-only state by determining that the memory bank is in the unlocked writeable state; and
   enabling operation of the medical waste collection device to provide the suction at the surgical site responsive to determining that the third memory bank exhibits the second behavioral characteristic consistent with the first non-permanent read-only state.

136. The method of any one of clauses 132 to 135, wherein the second memory bank is locked in a second non-permanent read-only state effective in both the open state and he secured state, and further comprising:
   determining that the second memory bank exhibits a behavioral characteristic consistent with the second non-permanent read-only state using the access password; and
   enabling operation of the medical waste collection device to provide the suction at the surgical site responsive to determining that the first memory blocks each includes the behavioral characteristic consistent with the permanent read-only state, the second memory blocks each does not include the behavioral characteristic consistent with the permanent read-only state, the third memory bank includes the behavioral characteristic consistent with the first non-permanent read-only state and the second memory bank includes the behavioral characteristic consistent with the second non-permanent read-only state.

137. The method of clause 136, wherein determining that the second memory bank exhibits a behavioral characteristic consistent with the second non-permanent read-only state using the access password by being configured to:
   communicating a first write command for the second memory bank to the RFID tag when the RFID tag is in the open state;
   determining that the first write command fails;
   responsive to determining that the first write command fails, transitioning the RFID tag to the secured state using the access password; and
   communicating a second write command for the second memory bank to the RFID tag when the RFID tag is in the secured state;
   determining that the second write command fails; and
   determining that the second memory bank exhibits the behavioral characteristic consistent with the second non-permanent read-only state responsive to determining that the second write command fails.

138. The method of clause 136 or 137, further comprising, responsive to determining that the first memory blocks each includes the behavioral characteristic consistent with the permanent read-only state, the second memory blocks each does not include the behavioral characteristic consistent with the permanent read-only state, the third memory bank includes the behavioral characteristic consistent the first non-permanent read-only state, and the second memory bank includes the behavioral characteristic consistent with the second non-permanent read-only state, communicating a recommission command to the RFID tag, wherein responsive to receiving the recommission command, the RFID tag is configured to:
   store data indicative that the RFID tag has been recommissioned in the RFID tag; and
   transition the third memory bank from the first non-permanent read-only state and the second memory bank from the second non-permanent read-only state to an unlocked writeable state,
   wherein each of the one or more first memory blocks remains locked in the permanent read-only state responsive to execution of the recommission command by the RFID tag.

139. The method of clause 138, wherein the behavioral characteristic consistent with the second non-permanent read-only state is a first behavioral characteristic consistent with the second non-permanent read-only state, and further comprising, responsive to the RFID tag executing the recommission command:
   determining that the second memory bank exhibits a second behavioral characteristic consistent with the second non-permanent read-only state by determining that the second memory bank is in an unlocked writeable state; and
   enabling operation of the medical waste collection device to provide the suction at the surgical site responsive to determining that the second memory bank exhibits the second behavioral characteristic consistent with the second non-permanent read-only state.

140. The method of any one of clauses 128 to 139, further comprising, responsive to determining that the first memory blocks each includes the behavioral characteristic consistent with the permanent read-only state, the second memory blocks each does not include the behavioral characteristic consistent with the permanent read-only state, and the third memory bank includes the behavioral characteristic consistent the first non-permanent read-only state:
   communicating use history data for the manifold to the RFID tag to be written in the third memory bank when the RFID tag is in the secured state; and
   after the use history data for the manifold is written to the third memory bank, communicating the recommission command to the RFID tag.

What is claimed is:
1. A medical waste collection system comprising:
   a medical waste collection device for providing suction at a surgical site;
   a manifold releasably couplable to the medical waste collection device and defining a pathway through which the medical waste collection device is configured to provide the suction to the surgical site, the manifold including an RFID tag including a first memory bank storing an identifier for the RFID tag, a second memory bank for storing electronic identification data for the manifold, and a third memory bank for storing user data, the third memory bank including a plurality of memory blocks with one or more first memory blocks of the plurality of memory blocks being locked in a permanent read-only state and one or more second memory blocks of the plurality of memory blocks not being locked in the permanent read-only state according to a predefined lock pattern for verifying the RFID tag by the medical waste collection system; and
   a controller of the medical waste collection device that is configured to, responsive to the manifold being coupled to the medical waste collection device:

determine that the one or more first memory blocks each exhibits a behavioral characteristic consistent with the permanent read-only state and the one or more second memory blocks each does not exhibit the behavioral characteristic of the permanent read-only state; and enable operation of the medical waste collection device to provide the suction at the surgical site responsive to determining that the one or more first memory blocks each exhibits the behavioral characteristic consistent with the permanent read-only state and the one or more second memory blocks each does not exhibit the behavioral characteristic of the permanent read-only state.

2. The system of claim 1, wherein the controller is configured to determine that the one or more first memory blocks each exhibits a behavioral characteristic consistent with the permanent read-only state and the one or more second memory blocks each does not exhibit the behavioral characteristic of the permanent read-only state by being configured to determine that the RFID tag is in a non-recommissioned state, and that the one or more first memory blocks are each read-only and the one or more second memory blocks are each not read-only when the RFID tag is in the non-recommissioned state.

3. The system of claim 1, wherein the behavioral characteristic is a first behavioral characteristic, and the controller is configured to, responsive to determining that the one or more first memory blocks each exhibits the first behavioral characteristic consistent with the permanent read-only state:

communicate a recommission command to the RFID tag;

after the recommission command is communicated, determine that the one or more first memory blocks each exhibits a second behavioral characteristic consistent with the permanent read-only state; and enable operation of the medical waste collection device to provide the suction at the surgical site responsive to determining that each of the one or more first memory blocks exhibits the second behavioral characteristic consistent with the permanent read-only state.

4. The system of claim 3, wherein the controller is configured to determine that the one or more first memory blocks each exhibits the second behavioral characteristic consistent with the permanent read-only state by being configured to determine that the one or more first memory blocks each is read-only after the recommission command is communicated.

5. The system of claim 1, wherein the third memory bank is locked in a non-permanent read-only state, and the controller is configured to:

determine that the third memory bank exhibits a behavioral characteristic consistent with the non-permanent read-only state; and enable operation of the medical waste collection device to provide the suction at the surgical site responsive to determining that the one or more first memory blocks each exhibits the behavioral characteristic consistent with the permanent read-only state, the one or more second memory blocks each does not exhibit the behavioral characteristic consistent with the permanent read-only state, and the third memory bank exhibits the behavioral characteristic consistent with the non-permanent read-only state.

6. The system of claim 5, wherein the behavioral characteristic consistent with the non-permanent read-only state is a first behavioral characteristic consistent with the non-permanent read-only state, and the controller is configured to, responsive to determining that the one or more first memory blocks each exhibits the behavioral characteristic consistent with the permanent read-only state, the one or more second memory blocks each does not exhibit the behavioral characteristic consistent with the permanent read-only state, and the third memory bank exhibits the first behavioral characteristic consistent with the non-permanent read-only state:

communicate a recommission command to the RFID tag; and after the recommission command is communicated:

determine that the third memory bank exhibits a second behavioral characteristic consistent with the non-permanent read-only state by determining that the third memory bank is in an unlocked writeable state; and enable operation of the medical waste collection device to provide the suction at the surgical site responsive to determining that the third memory bank exhibits the second behavioral characteristic consistent with the non-permanent read-only state.

7. The system of claim 1, wherein the RFID tag further comprises a fourth memory bank storing an access password for selectively transitioning the RFID tag between a secured state and an open state, the third memory bank is locked in a first non-permanent read-only state effective in the open state and not the secured state, and the controller is configured to:

determine that the third memory bank exhibits a behavioral characteristic consistent with the first non-permanent read-only state using the access password; and enable operation of the medical waste collection device to provide the suction at the surgical site responsive to determining that the one or more first memory blocks each exhibits the behavioral characteristic consistent with the permanent read-only state, the one or more second memory blocks each does not exhibit the behavioral characteristic consistent with the permanent read-only state, and the third memory bank exhibits the behavioral characteristic consistent with the first non-permanent read-only state.

8. A method for preparing an RFID tag for a manifold configured to be coupled to a vacuum inlet integral with a medical waste collection device to provide suction at a surgical site through the manifold, the method comprising:

obtaining a memory device for the RFID tag, the memory device comprising a first memory bank storing an identifier for the RFID tag, a second memory bank for storing electronic identification data for the manifold, and a third memory bank for storing user data, the third memory bank comprising a plurality of memory blocks;

writing to the third memory bank a rover type datum corresponding to the medical waste collection device, a first hash digest generated based on the rover type datum, use history data for the manifold, and a second hash digest generated based on the use history data for the manifold; and locking one or more first memory blocks of the plurality of memory blocks of the third memory bank in a permanent read-only state such that one or more second memory blocks of the plurality of memory blocks of the third memory bank are not locked in the permanent read-only state according to a predefined lock pattern for verifying the RFID tag by the medical waste collection device.

9. The method of claim 8, further comprising writing first user data indicating the rover type datum and the first hash digest to the third memory bank such that at least a portion of the first user data is stored in the one or more first memory blocks, and writing second user data indicating the use history data for the manifold and the second hash digest generated based on the use history data for the manifold to the one or more second memory blocks.

10. The method of claim 8, wherein the one or more first memory blocks comprises a plurality of first memory blocks, and further comprising locking the first memory blocks according to the predefined lock pattern for verifying the RFID tag by the medical waste collection device such that the plurality of first memory blocks are interspaced by at least one of the one or more second memory blocks within the third memory bank.

11. The method of claim 8, wherein locking the one or more first memory blocks of the third memory bank in a permanent read-only state such that the one or more second memory blocks of the third memory bank are not locked in the permanent read-only state according to a predefined lock pattern for verifying the RFID tag by the medical waste collection device comprises locking at least two of the memory blocks of the third memory bank in the permanent read-only state such that at least four of the memory blocks of the third memory bank are not locked in the permanent read-only state according to the predefined lock pattern for verifying the RFID tag by the medical waste collection device.

12. The method of claim 8, further comprising locking the third memory bank in a non-permanent read-only state according to the predefined lock pattern for verifying the RFID tag by the medical waste collection device.

13. The method of claim 8, wherein the memory device further comprises a fourth memory bank, and further comprising:
 writing to the fourth memory bank an access password for selectively transitioning the RFID tag between a secured state and an open state; and
 locking the third memory bank in a first non-permanent read-only state that is effective in the open state and not the secured state according to the predefined lock pattern for verifying the RFID tag by the medical waste collection device.

14. An RFID tag for a manifold configured to be coupled to a vacuum inlet integral with a medical waste collection device to provide suction at a surgical site through the manifold or a manifold including an RFID tag, the RFID tag comprising:
 a memory device storing data for being read by the medical waste collection device when the manifold is proximate the medical waste collection device to control actuation of the medical waste collection device, the memory device comprising:
  a first memory bank storing an identifier for the RFID tag;
  a second memory bank storing electronic identification data for the manifold; and
  a third memory bank comprising a plurality of memory blocks with one or more first memory blocks of the plurality of memory blocks being locked in a permanent read-only state and one or more second memory blocks of the plurality of memory blocks not being locked in the permanent read-only state according to a predefined lock pattern for verifying the RFID tag by the medical waste collection device.

15. The RFID tag of claim 14, wherein the third memory bank stores first user data indicating a rover type datum corresponding to the medical waste collection device and a first hash digest generated based on the rover type datum, and stores second user data indicating use history data for the manifold and a second hash digest generated based on the use history data for the manifold, the second user data being stored in the one or more second memory blocks, and at least a portion of the first user data being stored in the one or more first memory blocks.

16. The RFID tag of claim 14, wherein the one or more first memory blocks comprises a plurality of first memory blocks, the plurality of first memory blocks being interspaced by at least one of the one or more second memory blocks within the third memory bank.

17. The RFID tag of claim 14, wherein the one or more first memory blocks comprises two first memory blocks and the one or more second memory blocks comprises four second memory blocks.

18. The RFID tag of claim 14, wherein the third memory bank is locked in a non-permanent read-only state according to the predefined lock pattern for verifying the RFID tag by the medical waste collection device.

19. The RFID tag of claim 14, further comprising a fourth memory bank storing an access password for selectively transitioning the RFID tag between a secured state and an open state, wherein the third memory bank is locked in a first non-permanent read-only state effective in the open state and not the secured state according to the predefined lock pattern for verifying the RFID tag by the medical waste collection device.

20. The RFID tag of claim 19, wherein the second memory bank is locked in a second non-permanent read-only state effective in the open state and the secured state according to the predefined lock pattern for verifying the RFID tag by the medical waste collection device.

* * * * *